US011917906B2

(12) United States Patent
Stoessel

(10) Patent No.: US 11,917,906 B2
(45) Date of Patent: Feb. 27, 2024

(54) COMPOUNDS THAT CAN BE USED IN AN ORGANIC ELECTRONIC DEVICE

(71) Applicant: Merck Patent GmbH, Darmstadt (DE)

(72) Inventor: Philipp Stoessel, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 456 days.

(21) Appl. No.: 17/291,352

(22) PCT Filed: Nov. 4, 2019

(86) PCT No.: PCT/EP2019/080036
§ 371 (c)(1),
(2) Date: May 5, 2021

(87) PCT Pub. No.: WO2020/094539
PCT Pub. Date: May 14, 2020

(65) Prior Publication Data
US 2021/0391538 A1 Dec. 16, 2021

(30) Foreign Application Priority Data

Nov. 5, 2018 (EP) .................. 18204339

(51) Int. Cl.
| H10K 85/60 | (2023.01) |
| H10K 50/11 | (2023.01) |
| H10K 50/15 | (2023.01) |
| H10K 50/16 | (2023.01) |
| H10K 101/10 | (2023.01) |

(52) U.S. Cl.
CPC ......... *H10K 85/633* (2023.02); *H10K 85/622* (2023.02); *H10K 85/624* (2023.02); *H10K 85/626* (2023.02); *H10K 85/654* (2023.02); *H10K 85/6572* (2023.02); *H10K 85/6574* (2023.02); *H10K 85/6576* (2023.02); *H10K 50/11* (2023.02); *H10K 50/15* (2023.02); *H10K 50/16* (2023.02); *H10K 2101/10* (2023.02)

(58) Field of Classification Search
CPC .. H10K 85/633; H10K 85/624; H10K 85/654; H10K 85/6574; H10K 85/622; H10K 85/6576; H10K 85/626; H10K 85/6572; H10K 2101/10; H10K 50/16; H10K 50/11; H10K 50/15
USPC .......................................................... 257/40
See application file for complete search history.

(56) References Cited

U.S. PATENT DOCUMENTS

| 4,539,507 A | 9/1985 | Vanslyke et al. |
| 5,151,629 A | 9/1992 | Vanslyke |
| 2012/0045862 A1* | 2/2012 | Thompson ............. C23C 14/12 257/E51.026 |
| 2014/0286851 A1* | 9/2014 | Hodes .................... B01J 19/126 204/157.43 |
| 2016/0133839 A1* | 5/2016 | Li ......................... H10K 85/371 257/40 |
| 2017/0225954 A1* | 8/2017 | Hodes ..................... C30B 29/04 |
| 2019/0292450 A1* | 9/2019 | Li ........................... C07F 1/005 |
| 2020/0263085 A1* | 8/2020 | Li ......................... H01L 33/502 |
| 2021/0047297 A1* | 2/2021 | Schulze ............... C07D 401/14 |

FOREIGN PATENT DOCUMENTS

| EP | 0676461 A2 | 10/1995 |
| WO | 98/27136 A1 | 6/1998 |
| WO | 2018/019688 A1 | 2/2018 |

OTHER PUBLICATIONS

Freedman et al., "Tetraphenylcyclobutadiene Derivatives. IV.1"Octaphenylcubane"; A Dimer of Tetraphenylcyclobutadiene", J. Am. Chem. Soc. 1962, vol. 84, No. 14, pp. 2837-2838.
International Preliminary Report on Patentability received for PCT Patent Application No. PCT/EP2019/080036, dated May 20, 2021, 18 pages (10 pages of English Translation and 8 pages of Original Document).
International Search Report and Written Opinion received for PCT Patent Application No. PCT/EP2019/080036, dated Dec. 19, 2019, 21 pages (9 pages of English Translation and 22 pages of Original Document).
Maitlis et al, Proceedings of Chemical Soc. 1962, pp. 330-332.
Eaton Von Philip E., "Cubane: Ausgangsverbindungen fur die Chemie der neunziger Jahre und des nachsten Jahrhunderts" Angewandte Chemie, DE, vol. 104, 1992, pp. 1447-1462.
Bashir-Hashemi et al., "Chemistry and structure of phenylcubanes," The Journal of Organic Chemistry, vol. 55, No. 2, Jan. 1, 1990, pp. 416-420.
Buchi et al., "Photochemical Reactions. XI. Diphenylacetylene1-3," The Journal of Organic Chemistry, vol. 27, No. 11, Nov. 1, 1962, pp. 4106-4107.
Eaton, P. E., "Cubanes: Starting Materials for the Chemistry of the 1990s and the New Century," Angewandte Chemie, vol. 31, Issue 11, Nov. 1992, pp. 1421-1436.
Paulson et al., "Long-distance electron transfer through rodlike molecules with cubyl spacers," The Jouranl of Physical Chemistry, vol. 97, No. 50, Dec. 1, 1993, pp. 13042-13045.
Toriyama et al., "Redox-Active Esters in Fe-Catalyzed C—C Coupling," Journal of the American Chemical Society, vol. 138, No. 35, Aug. 22, 2016, pp. 11132-11135.

* cited by examiner

*Primary Examiner* — Igwe U Anya
(74) *Attorney, Agent, or Firm* — Faegre Drinker Biddle & Reath LLP

(57) ABSTRACT

The invention relates to compounds that can be used in an organic electronic device as an active compound, in particular for use in electronic devices. The invention further relates to a process for preparing the compounds according to the invention, and to electronic devices comprising the same.

20 Claims, No Drawings

COMPOUNDS THAT CAN BE USED IN AN ORGANIC ELECTRONIC DEVICE

CROSS-REFERENCE TO RELATED APPLICATIONS

This application is a national stage application (under 35 U.S.C. § 371) of PCT/EP2019/080036, filed Nov. 4, 2019, which claims benefit of European Application No. 18204339.8, filed Nov. 5, 2018, both of which are incorporated herein by reference in their entirety.

The present invention describes compounds, especially for use in electronic devices. The invention further relates to a process for preparing the compounds of the invention and to electronic devices comprising these compounds.

The structure of organic electroluminescent devices (OLEDs) in which organic semiconductors are used as functional materials is described, for example, in U.S. Pat. Nos. 4,539,507, 5,151,629, EP 0676461, WO 98/27136 and WO 2018/019688. Emitting materials used are frequently organometallic complexes which exhibit phosphorescence. For quantum-mechanical reasons, up to four times the energy efficiency and power efficiency is possible using organometallic compounds as phosphorescent emitters. In general terms, there is still a need for improvement in OLEDs, especially also in OLEDs which exhibit phosphorescence, for example with regard to efficiency, operating voltage and lifetime. Also known are organic electroluminescent devices comprising fluorescent emitters or emitters that exhibit TADF (thermally activated delayed fluorescence).

The properties of organic electroluminescent devices are not only determined by the emitters used. Also of particular significance here are especially the other materials used, such as host/matrix materials, hole blocker materials, electron transport materials, hole transport materials and electron or exciton blocker materials. Improvements to these materials can lead to distinct improvements to electroluminescent devices.

In addition, compounds having cubane structures are inter alia in the publications P. E. Eaton, "Cubane: Ausgangsverbindungen fur die Chemie der neunziger Jahre und des nachsten Jahrhunderts" [Cubanes: Starting Materials for the Chemistry of the 1990s and the New Century], *Angew. Chem.* 1992, 104, 1447-1462; H. H. Freedman and D. R. Petersen "Tetraphenylcyclobutadiene derivatives "octaphenylcubane"—a dimer of tetraphenylcyclobutadiene", *Journal of the American Chemical Society* (JACS), 1962, 2837-2838 and P. M. Maitlis and F. G. A. Stone, "A Convenient New Synthesis of the Hydrocarbon Reported to be Octaphenylcubane", *Proceedings of the Chemical Society,* 1962, 330-332. However, these compounds are not described in association with electronic devices. Compounds that can be actively used in electronic devices, such as matrix materials, electron transport materials, hole transport materials, phosphorescent emitters, fluorescent emitters or emitters that exhibit TADF (thermally activated delayed fluorescence), are not set out in these documents.

In general terms, in the case of these materials, for example for use as matrix materials, hole conductor materials or electron transport materials, there is still a need for improvement, particularly in relation to the lifetime, but also in relation to the efficiency and operating voltage of the device. Moreover, the compounds should have high color purity.

It is a further object of the present invention to provide compounds which are suitable for use in an organic electronic device, especially in an organic electroluminescent device, as fluorescent emitters or emitters that exhibit TADF (thermally activated delayed fluorescence), and which lead to good device properties when used in this device, and to provide the corresponding electronic device.

It is therefore an object of the present invention to provide compounds which are suitable for use in an organic electronic device, especially in an organic electroluminescent device, and which lead to good device properties when used in this device, and to provide the corresponding electronic device.

It is a particular object of the present invention to provide compounds which lead to a high lifetime, good efficiency and low operating voltage. Particularly the properties of the matrix materials, the hole conductor materials or the electron transport materials too have an essential influence on the lifetime and efficiency of the organic electroluminescent device.

A further problem addressed by the present invention can be considered that of providing compounds suitable for use in a phosphorescent or fluorescent OLED, especially as a matrix material. More particularly, a problem addressed by the present invention is that of providing matrix materials suitable for red-, yellow- and green-phosphorescing OLEDs.

In addition, the compounds, especially when they are used as matrix materials, as hole conductor materials or as electron transport materials in organic electroluminescent devices, should lead to devices having excellent color purity.

Moreover, the compounds should be processible in a very simple manner, and especially exhibit good solubility and film formation. For example, the compounds should exhibit elevated oxidation stability and an improved glass transition temperature.

A further problem addressed can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, particular compounds that are described in detail hereinafter solve these problems and eliminate the disadvantage from the prior art. The use of the compounds leads to very good properties of organic electronic devices, especially of organic electroluminescent devices, especially with regard to lifetime, efficiency and operating voltage. The present invention therefore provides electronic devices, especially organic electroluminescent devices, comprising compounds of this kind, and the corresponding preferred embodiments.

The present invention therefore provides a compound usable as active compound an organic electronic device, the compound preferably being a purely organic compound, characterized in that the compound comprises at least one structure of the formula (I), the compound preferably having the formula specified:

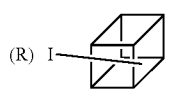

Formula (I)

where:
- l is an integer in the range from 1 to 8, preferably 2, 4, 6 or 8;
- R is the same or different at each instance and is H, D, OH, F, Cl, Br, I, CN, $NO_2$, $N(Ar)_2$, $N(R^1)_2$, $C(=O)N(Ar)_2$, $C(=O)N(R^1)_2$, $Si(Ar)_3$, $Si(R^1)_3$, $B(Ar)_2$, $B(R^1)_2$, $C(=O)Ar$, $C(=O)R^1$, $P(=O)(Ar)_2$, $P(=O)(R^1)_2$, $P(Ar)_2$, $P(R^1)_2$, $S(=O)Ar$, $S(=O)R^1$, $S(=O)_2Ar$, $S(=O)_2R^1$, $OSO_2Ar$, $OSO_2R^1$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may in each case be substituted by one or more $R^1$ radicals, where one or more nonadjacent $CH_2$ groups may be replaced by $R^1C=CR^1$, $C\equiv C$, $Si(R^1)_2$, $Ge(R^1)_2$, $Sn(R^1)_2$, $C=O$, $C=S$, $C=Se$, $C=NR^1$, $-C(=O)O-$, $-C(=O)NR^1-$, $NR^1$, $P(=O)(R^1)$, $-O-$, $-S-$, SO or $SO_2$, or an aromatic or heteroaromatic ring system which has 5 to 60 aromatic ring atoms and may be substituted in each case by one or more $R^1$ radicals, or an aryloxy or heteroaryloxy group which has 5 to 60 aromatic ring atoms and may be substituted by one or more $R^1$ radicals; at the same time, two R radicals together may also form a ring system;
- Ar is the same or different at each instance and is an aromatic or heteroaromatic ring system which has 5 to 60 aromatic ring atoms and may be substituted by one or more $R^1$ radicals; at the same time, it is possible for two Ar radicals bonded to the same silicon atom, nitrogen atom, phosphorus atom or boron atom also to be joined together via a bridge by a single bond or a bridge selected from $B(R^1)$, $C(R^1)_2$, $Si(R^1)_2$, $C=O$, $C=NR^1$, $C=C(R^1)_2$, O, S, $S=O$, $SO_2$, $N(R^1)$, $P(R^1)$ and $P(=O)R^1$;
- $R^1$ is the same or different at each instance and is H, D, F, Cl, Br, I, CN, $NO_2$, $N(Ar^1)_2$, $N(R^2)_2$, $C(=O)Ar^1$, $C(=O)R^2$, $P(=O)(Ar^1)_2$, $P(Ar^1)_2$, $B(Ar^1)_2$, $B(R^2)_2$, $Si(Ar^1)_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $-C(=O)O-$, $-C(=O)NR^2-$, $NR^2$, $P(=O)(R^2)$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a combination of these systems; at the same time, two or more, preferably adjacent $R^1$ radicals together may form a ring system; at the same time, one or more $R^1$ radicals with a further part of the compound may form a ring system;
- $Ar^1$ is the same or different at each instance and is an aromatic or heteroaromatic ring system which has 5 to 30 aromatic ring atoms and may be substituted by one or more, preferably nonaromatic $R^2$ radicals; at the same time, it is possible for two $Ar^1$ radicals bonded to the same silicon atom, nitrogen atom, phosphorus atom or boron atom also to be joined to one another via a bridge by a single bond or a bridge selected from $B(R^2)$, $C(R^2)_2$, $Si(R^2)_2$, $C=O$, $C=NR^2$, $C=C(R^2)_2$, O, S, $S=O$, $SO_2$, $N(R^2)$, $P(R^2)$ and $P(=O)R^2$;
- $R^2$ is the same or different at each instance and is H, D, F, C, Br, I, CN, $B(OR^3)_2$, $NO_2$, $C(=O)R^3$, $CR^3=C(R^3)_2$, $C(=O)OR^3$, $C(=O)N(R^3)_2$, $Si(R^3)_3$, $P(R^3)_2$, $B(R^3)_2$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by $-R^3C=CR^3-$, $-C\equiv C-$, $Si(R^3)_2$, $Ge(R^3)_2$, $Sn(R^3)_2$, $C=O$, $C=S$, $C=NR^3$, $-C(=O)O-$, $-C(=O)NR^3-$, $NR^3$, $P(=O)(R^3)$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^3$ radicals, or an aryloxy or heteroaryloxy group which has 5 to 40 aromatic ring atoms and may be substituted by one or more $R^3$ radicals, or a combination of these systems; at the same time, two or more, preferably adjacent substituents $R^2$ together may also form a ring system;
- $R^3$ is the same or different at each instance and is selected from the group consisting of H, D, F, CN, an aliphatic hydrocarbyl radical having 1 to 20 carbon atoms or an aromatic or heteroaromatic ring system which has 5 to 30 aromatic ring atoms and in which one or more hydrogen atoms may be replaced by D, F, C, Br, I or CN and which may be substituted by one or more alkyl groups each having 1 to 4 carbon atoms; at the same time, two or more, preferably adjacent substituents $R^3$ together may form a ring system.

Active compounds are generally the organic or inorganic materials introduced between anode and cathode, for example in an organic electronic device, especially in an organic electroluminescent device, for example charge injection, charge transport or charge blocker materials, but especially emission materials and matrix materials. Preference is given here to organic materials.

The compound usable as active compound an organic electronic device is preferably a purely organic compound. A purely organic compound is a compound not associated with a metal atom, i.e. not forming a coordination compound with a metal atom nor forming a covalent bond with a metal atom. A purely organic compound here preferably does not comprise any metal atom which is used in phosphorescent emitters. These metals, such as copper, molybdenum, etc., especially rhenium, ruthenium, osmium, rhodium, iridium, palladium, will be discussed in detail later on.

The compound usable as active compound an organic electronic device may preferably be selected from the group consisting of fluorescent emitters, phosphorescent emitters, emitters that exhibit TADF (thermally activated delayed fluorescence), host materials, electron transport materials, exciton blocker materials, electron injection materials, hole conductor materials, hole injection materials, n-dopants, p-dopants, wide bandgap materials, electron blocker materials and/or hole blocker materials. Preference is given here to fluorescent emitters, emitters that exhibit TADF (thermally activated delayed fluorescence), host materials, electron transport materials, exciton blocker materials, electron injection materials, hole conductor materials, hole injection materials, n-dopants, p-dopants, wide bandgap materials, electron blocker materials and/or hole blocker materials.

In a preferred configuration, the compound of the invention may comprise at least one structure of the formula (II), the compound preferably having the formula specified:

Formula (II)

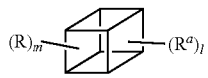

where the R radical has the definition given above, especially for formula (I), and in addition:

l is an integer in the range from 1 to 8, preferably 2, 4, 6 or 8;

m is an integer in the range from 0 to 7, preferably 0, 1, 2, 3 or 4;

m+l is not more than 8;

$R^a$ is the same or different at each instance and is OH, F, Cl, Br, I, CN, $NO_2$, $N(Ar)_2$, $N(R^1)_2$, $C(=O)N(Ar)_2$, $C(=O)N(R^1)_2$, $Si(Ar)_3$, $Si(R^1)_3$, $B(Ar)_2$, $B(R^1)_2$, $C(=O)Ar$, $C(=O)R^1$, $P(=O)(Ar)_2$, $P(=O)(R^1)_2$, $P(Ar)_2$, $P(R^1)_2$, $S(=O)Ar$, $S(=O)R^1$, $S(=O)_2Ar$, $S(=O)_2R^1$, $OSO_2Ar$, $OSO_2R^1$, a straight-chain alkyl, alkoxy or thioalkoxy group having 1 to 20 carbon atoms or an alkenyl or alkynyl group having 2 to 40 carbon atoms or a branched or cyclic alkyl, alkoxy or thioalkoxy group having 3 to 40 carbon atoms, where the alkyl, alkoxy, thioalkoxy, alkenyl or alkynyl group may in each case be substituted by one or more $R^1$ radicals, where one or more nonadjacent $CH_2$ groups may be replaced by $R^1C=CR^1$, C≡C, $Si(R^1)_2$, Ge $(R^1)_2$, $Sn(R^1)_2$, C=O, C=S, C=Se, $C=NR^1$, —C(=O)O—, —C(=O)$NR^1$—, $NR^1$, $P(=O)(R^1)$, —O—, —S—, SO or $SO_2$, or an aromatic or heteroaromatic ring system which has 5 to 60 aromatic ring atoms and may be substituted in each case by one or more $R^1$ radicals, or an aryloxy or heteroaryloxy group which has 5 to 60 aromatic ring atoms and may be substituted by one or more $R^1$ radicals; at the same time, $R^a$ radicals with an R radical may also form a ring system, where the Ar and $R^1$ radicals have the definition given above, especially for formula (I).

Adjacent carbon atoms in the context of the present invention are carbon atoms bonded directly to one another. In addition, "adjacent radicals" in the definition of the radicals means that these radicals are bonded to the same carbon atom or to adjacent carbon atoms. These definitions apply correspondingly, inter alia, to the terms "adjacent groups" and "adjacent substituents".

The wording that two or more radicals together may form a ring, in the context of the present description, should be understood to mean, inter alia, that the two radicals are joined to one another by a chemical bond with formal elimination of two hydrogen atoms. This is illustrated by the following scheme:

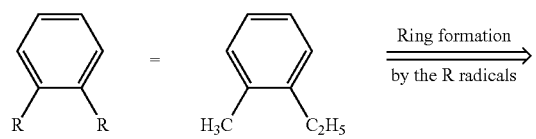

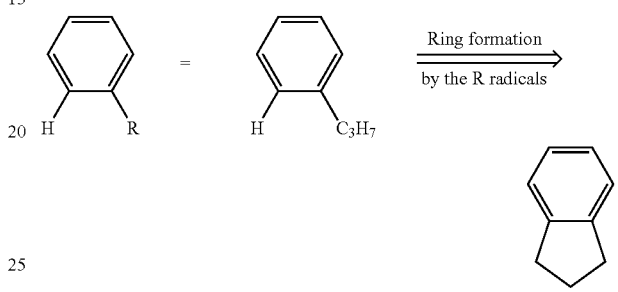

In addition, however, the abovementioned wording shall also be understood to mean that, if one of the two radicals is hydrogen, the second radical binds to the position to which the hydrogen atom was bonded, forming a ring. This shall be illustrated by the following scheme:

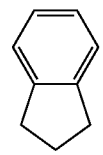

A fused aryl group, a fused aromatic ring system or a fused heteroaromatic ring system in the context of the present invention is a group in which two or more aromatic groups are fused, i.e. annelated, to one another along a common edge, such that, for example, two carbon atoms belong to the at least two aromatic or heteroaromatic rings, as, for example, in naphthalene. By contrast, for example, fluorene is not a fused aryl group in the context of the present invention, since the two aromatic groups in fluorene do not have a common edge. Corresponding definitions apply to heteroaryl groups and to fused ring systems which may but need not also contain heteroatoms.

If two or more, preferably adjacent R, $R^1$, $R^2$ and/or $R^3$ radicals together form a ring system, the result may be a monocyclic or polycyclic, aliphatic, aromatic or heteroaromatic ring system.

An aryl group in the context of this invention contains 6 to 60 carbon atoms, preferably 6 to 40 carbon atoms, more preferably 6 to 30 carbon atoms, a heteroaryl group in the context of this invention contains 2 to 60 carbon atoms, preferably 2 to 40 carbon atoms, more preferably 2 to 30 carbon atoms, and at least one heteroatom, with the proviso that the sum total of carbon atoms and heteroatoms is at least 5. The heteroatoms are preferably selected from N, O and/or S. Here, an aryl group or heteroaryl group is understood to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 60 carbon atoms, preferably 6 to 40 carbon atoms, more preferably 6 to 30 carbon atoms, in the ring system. A heteroaromatic ring system in the context of this invention contains 1 to 60 carbon atoms, preferably 1 to 40 carbon atoms, more preferably 1 to 30 carbon atoms, and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for a plurality of aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall thus also be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl, terphenyl, quaterphenyl or bipyridine, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{20}$-alkyl group in which individual hydrogen atoms or $CH_2$ groups may also be substituted by the abovementioned groups is understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5 to 60, preferably 5-40, aromatic ring atoms, more preferably 5 to 30 aromatic ring atoms, and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a further configuration, preference is given to compounds having point symmetry.

Preference is further given to compounds having axial symmetry.

The compounds of the invention may preferably have at least one structure of the formulae (IIIa), (IIIb) and (IIIc), the compound preferably having the formulae specified:

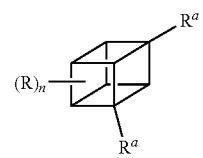

Formula (IIIa)

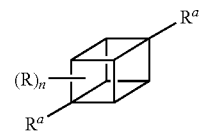

Formula (IIIb)

Formula (IIIc)

where the symbols R and $R^a$ have the definitions given above, especially for formula (I) or (II), and n is an integer in the range from 0 to 6, preferably 0, 1, 2, 3 or 4, more preferably 0, 2 or 4. Preference is given here to structures of the formulae (IIIa) and (IIIb).

In a further embodiment, it may be the case that the compound comprises at least one structure of the formulae (IVa), (IVb) and/or (IVc), the compound preferably having the formulae specified:

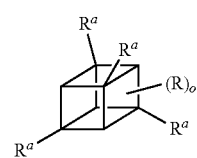

Formula (IVa)

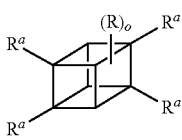

Formula (IVb)

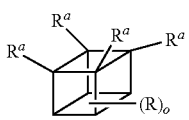

Formula (IVc)

where the symbols R and R$^a$ have the definitions given above, especially for formula (I) or (II), and o is an integer in the range from 0 to 4, preferably 0, 1, 2 or 3, more preferably 0 or 2. Preference is given here to structures of the formulae (IVa) and (IVb), particular preference to the structure of the formula (IVa).

It may further be the case that the compound comprises at least one structure of the formula (V), the compound preferably having the formula specified:

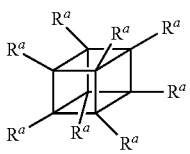

Formula (V)

where the symbol R$^a$ has the definition given above, especially for formula (II).

In one embodiment, it may be the case that at least two of the R$^a$ radicals in the structures of the formulae (II), (IIIa), (IIIb), (IIIc), (IVa), (IVb), (IVc) and/or (V) are the same, preferably all R$^a$ radicals are the same.

In a further configuration, it may be the case that at least two of the R$^a$ radicals in the structures of the formulae (II), (IIIa), (IIIb), (IIIc), (IVa), (IVb), (IVc) and/or (V) are different.

Preferably, at least one of the R and/or R$^a$ radicals is selected from the group of the fluorenes, indenofluorenes, spirobifluorenes, carbazoles, indenocarbazoles, indolocarbazoles, spirocarbazoles, pyrimidines, triazines, lactams, triarylamines, dibenzofurans, dibenzothienes, imidazoles, benzimidazoles, benzoxazoles, benzothiazoles, 5-arylphenanthridin-6-ones, 9,10-dehydrophenanthrenes, fluoranthenes, anthracenes, benzanthracenes, fluoradenes.

It may further be the case that at least one of the R and/or R$^a$ radicals is selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 9,9'-diarylfluorenyl 1-, 2-, 3- or 4-spirobifluorenyl, pyridyl, pyrimidinyl, 1-, 2-, 3- or 4-dibenzofuranyl, 1-, 2-, 3- or 4-dibenzothienyl, pyrenyl, triazinyl, imidazolyl, benzimidazolyl, benzoxazolyl, benzothiazolyl, 1-, 2-, 3- or 4-carbazolyl, 1- or 2-naphthyl, anthracenyl, preferably 9-anthracenyl, trans- and cis-indenofluorenyl, indenocarbazolyl, indolocarbazolyl, spirocarbazolyl, 5-aryl-phenanthridin-6-on-yl, 9,10-dehydrophenanthrenyl, fluoranthenyl, tolyl, mesityl, phenoxytolyl, anisolyl, triarylaminyl, bis(triarylaminyl), tris(triarylaminyl), hexamethylindanyl, tetralinyl, monocycloalkyl, biscycloalkyl, tricycloalkyl, alkyl, for example tert-butyl, methyl, propyl, alkoxyl, alkylsulfanyl, alkylaryl, triarylsilyl, trialkylsilyl, xanthenyl, 10-arylphenoxazinyl, phenanthrenyl and/or triphenylenyl, each of which may be substituted by one or more radicals, but are preferably unsubstituted, particular preference being given to phenyl, spirobifluorene, fluorene, dibenzofuran, dibenzothiophene, anthracene, phenanthrene, triphenylene groups.

When the cubane structure is substituted by substituents R and/or R$^a$, these substituents R and/or R$^a$ are preferably selected from the group consisting of H, D, F, CN, N(Ar)$_2$, C(=O)Ar, P(=O)(Ar)$_2$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more R$^1$ radicals, where one or more nonadjacent CH$_2$ groups may be replaced by O and where one or more hydrogen atoms may be replaced by D or F, an aromatic or heteroaromatic ring system which has 5 to 24 aromatic ring atoms and may be substituted in each case by one or more R$^1$ radicals, but is preferably unsubstituted, or an aralkyl or heteroaralkyl group which has 5 to 25 aromatic ring atoms and may be substituted by one or more R$^1$ radicals; at the same time, it is optionally possible for two substituents R and/or R$^a$, preferably bonded to adjacent carbon atoms, to form a monocyclic or polycyclic, aliphatic, aromatic or heteroaromatic ring system which may be substituted by one or more R$^1$ radicals; where the Ar group has the definition given above, especially for formula (I).

More preferably, these substituents R and/or R$^a$ are selected from the group consisting of H, D, F, CN, N(Ar)$_2$, a straight-chain alkyl group having 1 to 8 carbon atoms, preferably having 1, 2, 3 or 4 carbon atoms, or a branched or cyclic alkyl group having 3 to 8 carbon atoms, preferably having 3 or 4 carbon atoms, or an alkenyl group having 2 to 8 carbon atoms, preferably having 2, 3 or 4 carbon atoms, each of which may be substituted by one or more R$^1$ radicals, but is preferably unsubstituted, or an aromatic or heteroaromatic ring system which has 5 to 24 aromatic ring atoms, preferably 6 to 18 aromatic ring atoms, more preferably 6 to 13 aromatic ring atoms, and may be substituted in each case by one or more nonaromatic R$^1$ radicals, but is preferably unsubstituted; at the same time, it is optionally possible for two substituents R$^1$ preferably bonded to adjacent carbon atoms to form a monocyclic or polycyclic aliphatic ring system which may be substituted by one or more R$^2$ radicals, but is preferably unsubstituted, where Ar may have the definition set out above.

More preferably, the substituents R are selected from the group consisting of H or an aromatic or heteroaromatic ring system having 6 to 18 aromatic ring atoms, preferably having 6 to 13 aromatic ring atoms, each of which may be substituted by one or more nonaromatic R$^1$ radicals, but is preferably unsubstituted. Examples of suitable substituents R are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl, 1-, 2-, 3- or 4-carbazolyl and indenocarbazolyl, each of which may be substituted by one or more R$^1$ radicals, but are preferably unsubstituted.

Most preferably, the substituents R$^a$ are selected from the group consisting of an aromatic or heteroaromatic ring system which has 6 to 18 aromatic ring atoms, preferably 6 to 13 aromatic ring atoms, and may be substituted in each case by one or more nonaromatic R$^1$ radicals, but is preferably unsubstituted. Examples of suitable substituents R$^a$ are selected from the group consisting of phenyl, ortho-, metaor para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl, 1-, 2-, 3- or 4-carbazolyl and indenocarbazolyl, each of which may be substituted by one or more $R^1$ radicals, but are preferably unsubstituted.

It may additionally be the case that the substituents R and/or $R^a$ of the cubane structure of the formulae (I), (II), (IIIa), (IIIb), (IIIc), (IVa), (IVb), (IVc) and/or (V) do not form a fused aromatic or heteroaromatic ring system, and preferably do not form any fused ring system. This includes the formation of a fused ring system with possible substituents $R^1$, $R^2$, $R^3$ which may be bonded to the $R^1$ radicals.

In a further embodiment, it may be the case that the compound usable as active compound in an organic electronic device comprises a hole transport group, where preferably at least one of the R and/or $R^a$ groups in a structure of the formulae (I), (II), (IIIa), (IIIb), (IIIc), (IVa), (IVb), (IVc) and/or (V) comprises and preferably is a hole transport group. Hole transport groups are known in the technical field, and they preferably include triarylamine or carbazole groups.

It may preferably be the case that the hole transport group comprises a group and preferably is a group selected from the formulae (H-1) to (H-3)

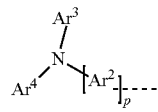

Formula (H-1)

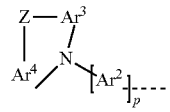

Formula (H-2)

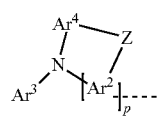

Formula (H-3)

where the dotted bond marks the position of attachment and the symbols are defined as follows:

$Ar^2$, $Ar^3$, $Ar^4$ is in each case independently an aromatic ring system having 6 to 40 carbon atoms or a heteroaromatic ring system having 3 to 40 carbon atoms, each of which may be substituted by one or more $R^1$ radicals;

p is 0 or 1;

Z is a bond or $C(R^1)_2$, $Si(R^1)_2$, C=O, $NR^1$, N—$Ar^1$, $BR^1$, $PR^1$, $PO(R^1)$, SO, $SO_2$, Se, O or S, preferably a bond or $C(R^1)_2$, N—$Ar^1$, O or S;

where the symbols $Ar^1$ and $R^1$ have the definition given above, especially for formula (I). At the same time, the presence of an N—N bond is preferably ruled out.

It may additionally be the case that the hole transport group comprises a group and preferably is a group selected from the formulae (H-4) to (H-26)

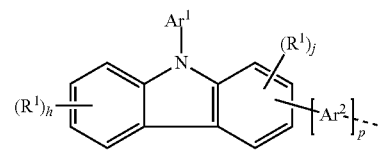

Formula (H-4)

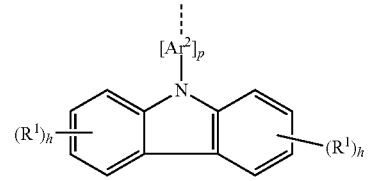

Formula (H-5)

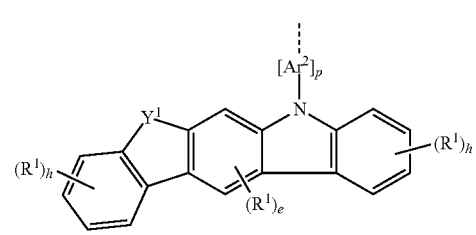

Formula (H-6)

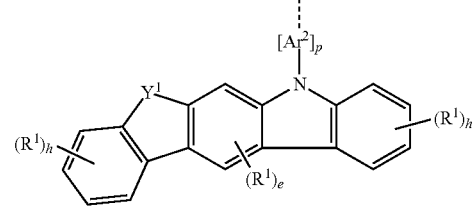

Formula (H-7)

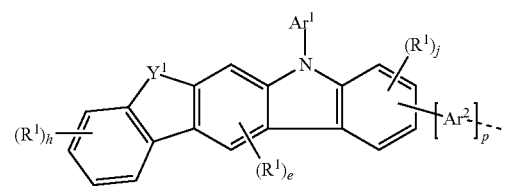

Formula (H-8)

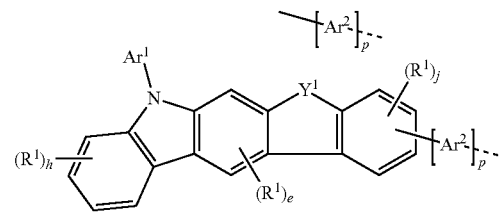

Formula (H-9)

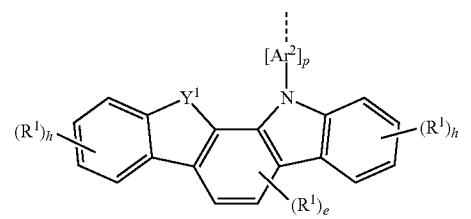

Formula (H-10)

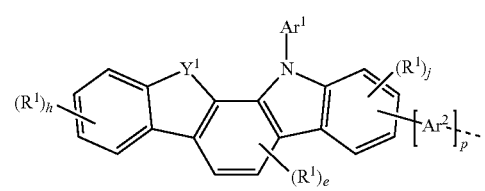

Formula (H-11)
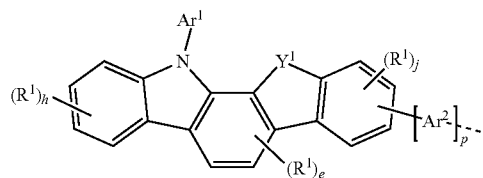
Formula (H-12)
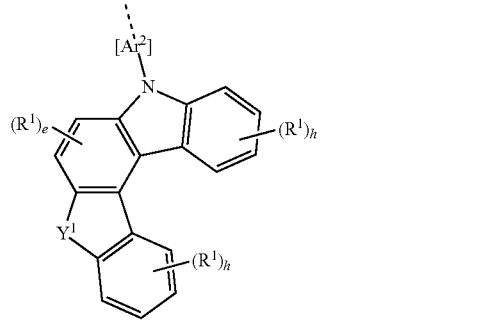
Formula (H-13)
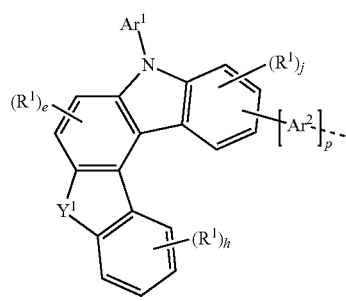
Formula (H-14)
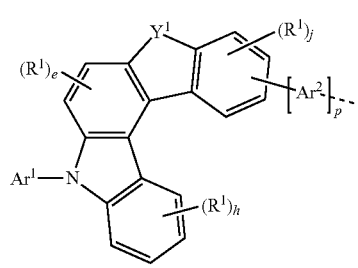
Formula (H-15)
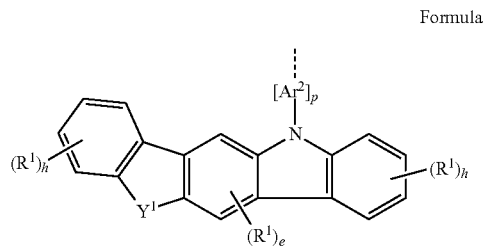
Formula (H-16)
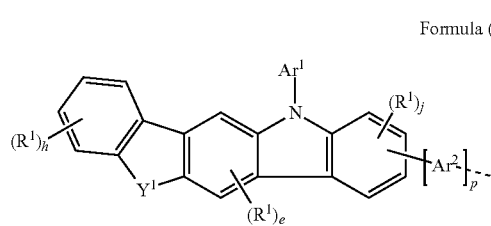
Formula (H-17)
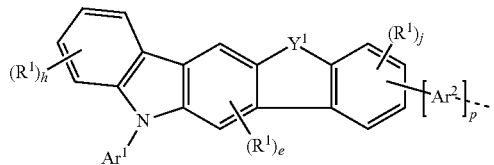
Formula (H-18)
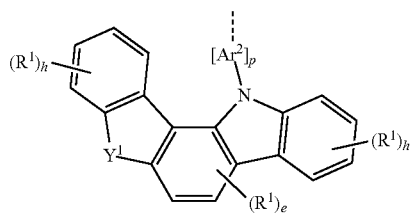
Formula (H-19)
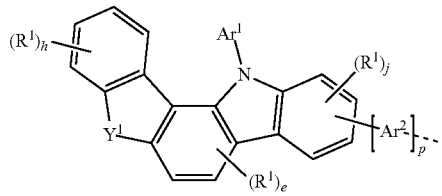
Formula (H-20)
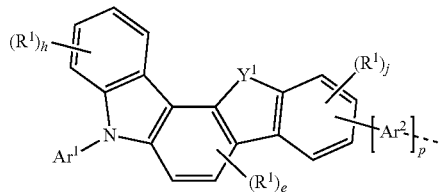
Formula (H-21)
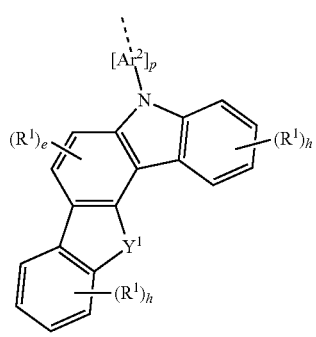
Formula (H-22)

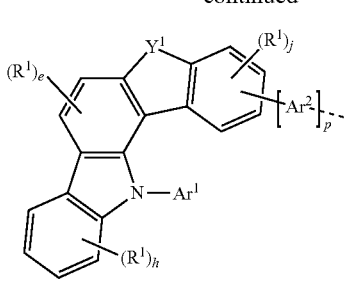

Formula (H-23)

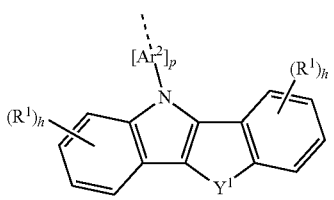

Formula (H-24)

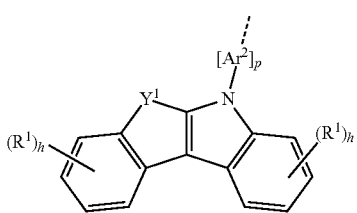

Formula (H-25)

where $Y^1$ is O, S, $C(R^1)_2$, $NR^1$ or $NAr^1$, the dotted bond marks the position of attachment, e is 0, 1 or 2, j is 0, 1, 2 or 3, h is the same or different at each instance and is 0, 1, 2, 3 or 4, p is 0 or 1, $Ar^1$ and $R^1$ have the definitions given above, especially for formula (I), and $Ar^2$ has the definitions given above, especially for formula (H-1) or (H-2). At the same time, the presence of an N—N bond is preferably ruled out.

It is clear from the above wording that, if the index is p=0, the corresponding $Ar^2$ group is absent and a bond is formed.

Preferably, the $Ar^2$ group may form through-conjugation with the aromatic or heteroaromatic radical or the nitrogen atom to which the $Ar^2$ group of the formulae (H-1) to (H-26) may be bonded.

In a further preferred embodiment of the invention, $Ar^2$ is an aromatic or heteroaromatic ring system which has 5 to 14 aromatic or heteroaromatic ring atoms, preferably an aromatic ring system which has 6 to 12 carbon atoms, and which may be substituted by one or more $R^1$ radicals, but is preferably unsubstituted, where $R^1$ may have the definition given above, especially for formula (I). More preferably, $Ar^2$ is an aromatic ring system having 6 to 10 aromatic ring atoms or a heteroaromatic ring system having 6 to 13 heteroaromatic ring atoms, each of which may be substituted by one or more $R^1$ radicals, but is preferably unsubstituted, where $R^1$ may have the definition given above, especially for formula (I).

Further preferably, the symbol $Ar^2$ shown in formulae (H-1) to (H-26) inter alia is an aryl or heteroaryl radical having 5 to 24 ring atoms, preferably 6 to 13 ring atoms, more preferably 6 to 10 ring atoms, such that an aromatic or heteroaromatic group of an aromatic or heteroaromatic ring system is bonded to the respective atom of the further group directly, i.e. via an atom of the aromatic or heteroaromatic group.

It may further be the case that the $Ar^2$ group shown in formulae (H-1) to (H-26) comprises an aromatic ring system having not more than two fused aromatic and/or heteroaromatic 6-membered rings; preferably it does not comprise any fused aromatic or heteroaromatic ring system with fused 6-membered rings. Accordingly, naphthyl structures are preferred over anthracene structures. In addition, fluorenyl, spirobifluorenyl, dibenzofuranyl and/or dibenzothienyl structures are preferred over naphthyl structures. Particular preference is given to structures having no fusion, for example phenyl, biphenyl, terphenyl and/or quaterphenyl structures.

It may further be the case that the $Ar^2$ group shown in formulae (H-1) to (H-26) inter alia has not more than 1 nitrogen atom, preferably not more than 2 heteroatoms, particularly preferably not more than one heteroatom and especially preferably no heteroatom.

In a further preferred embodiment of the invention, $Ar^3$ and/or $Ar^4$ are the same or different at each instance and are an aromatic or heteroaromatic ring system having 6 to 24 aromatic ring atoms, preferably 6 to 18 aromatic ring atoms, and are more preferably an aromatic ring system having 6 to 12 aromatic ring atoms or a heteroaromatic ring system having 6 to 13 aromatic ring atoms, each of which may be substituted by one or more $R^1$ radicals, but is preferably unsubstituted, where $R^1$ may have the definition given above, especially in formula (I).

In a further embodiment, it may be the case that the compound usable as active compound in an organic electronic device comprises an electron transport group-comprising radical, where preferably at least one of the R and/or $R^a$ groups in a structure of the formulae (I), (II), (IIIa), (IIIb), (IIIc), (IVa), (IVb), (IVc) and/or (V) comprises and preferably is an electron transport group-comprising radical. Electron transport groups are widely known in the technical field and promote the ability of compounds to transport and/or conduct electrons.

In addition, surprising advantages are shown by compounds usable as active compound in an organic electronic device that comprise at least one structure selected from the group of the pyridines, pyrimidines, pyrazines, pyridazines, triazines, quinazolines, quinoxalines, quinolines, isoquinolines, imidazoles and/or benzimidazoles, particular preference being given to pyrimidines, triazines and quinazolines. These structures generally promote the ability of compounds to transport and/or to conduct electrons.

In a preferred configuration of the present invention, it may be the case that the electron transport group-comprising radical is a group that can be represented by the formula (QL)

$$Q-L^1----$$

Formula (QL)

in which $L^1$ represents a bond or an aromatic or heteroaromatic ring system which has 5 to 40, preferably 5 to 30, aromatic ring atoms and may be substituted by one or more $R^1$ radicals, Q is an electron transport group, where $R^1$ has the definition given above, especially for formula (I), and the dotted bond marks the position of attachment.

Preferably, the $L^1$ group may form through-conjugation with the Q group and the atom, preferably the carbon or nitrogen atom, to which the $L^1$ group of formula (QL) is bonded. Through-conjugation of the aromatic or heteroaromatic systems is formed as soon as direct bonds are formed between adjacent aromatic or heteroaromatic rings. A further bond between the aforementioned conjugated groups, for example via a sulfur, nitrogen or oxygen atom or a carbonyl group, is not detrimental to conjugation. In the case of a fluorene system, the two aromatic rings are bonded directly, where the sp$^3$-hybridized carbon atom in position 9 does prevent fusion of these rings, but conjugation is possible since this sp$^3$-hybridized carbon atom in position 9 does not necessarily lie between the electron-transporting Q group and the atom via which the group of formula (QL) is bonded to further structural elements of a compound of the invention. In contrast, in the case of a second spirobifluorene structure, through-conjugation can be formed if the bond between the Q group and the aromatic or heteroaromatic radical to which the L$^1$ group of formula (QL) is bonded is via the same phenyl group in the spirobifluorene structure or via phenyl groups in the spirobifluorene structure that are bonded directly to one another and are in one plane. If the bond between the Q group and the aromatic or heteroaromatic radical to which the L$^1$ group of formula (QL) is bonded is via different phenyl groups in the second spirobifluorene structure bonded via the sp$^3$-hybridized carbon atom in position 9, the conjugation is interrupted.

In a further preferred embodiment of the invention, L$^1$ is a bond or an aromatic or heteroaromatic ring system which has 5 to 14 aromatic or heteroaromatic ring atoms, preferably an aromatic ring system which has 6 to 12 carbon atoms, and which may be substituted by one or more R$^1$ radicals, but is preferably unsubstituted, where R$^1$ may have the definition given above, especially for formula (I). More preferably, L$^1$ is an aromatic ring system having 6 to 10 aromatic ring atoms or a heteroaromatic ring system having 6 to 13 heteroaromatic ring atoms, each of which may be substituted by one or more R$^2$ radicals, but is preferably unsubstituted, where R$^2$ may have the definition given above, especially for formula (I).

Further preferably, the symbol L$^1$ shown in formula (QL) inter alia is the same or different at each instance and is a bond or an aryl or heteroaryl radical having 5 to 24 ring atoms, preferably 6 to 13 ring atoms, more preferably 6 to 10 ring atoms, such that an aromatic or heteroaromatic group of an aromatic or heteroaromatic ring system is bonded to the respective atom of the further group directly, i.e. via an atom of the aromatic or heteroaromatic group.

It may additionally be the case that the L$^1$ group shown in formula (QL) comprises an aromatic ring system having not more than two fused aromatic and/or heteroaromatic 6-membered rings, preferably does not comprise any fused aromatic or heteroaromatic ring system. Accordingly, naphthyl structures are preferred over anthracene structures. In addition, fluorenyl, spirobifluorenyl, dibenzofuranyl and/or dibenzothienyl structures are preferred over naphthyl structures.

Particular preference is given to structures having no fusion, for example phenyl, biphenyl, terphenyl and/or quaterphenyl structures.

Examples of suitable aromatic or heteroaromatic ring systems L$^1$ are selected from the group consisting of ortho-, meta- or para-phenylene, ortho-, meta- or para-biphenylene, terphenylene, especially branched terphenylene, quaterphenylene, especially branched quaterphenylene, fluorenylene, spirobifluorenylene, dibenzofuranylene, dibenzothienylene and carbazolylene, each of which may be substituted by one or more R$^1$ radicals, but are preferably unsubstituted.

It may further be the case that the L$^1$ group shown in formula (QL) inter alia has not more than 1 nitrogen atom, preferably not more than 2 heteroatoms, especially preferably not more than one heteroatom and more preferably no heteroatom.

Preferably, the Q group shown in the formula (QL) inter alia, or the electron transport group, may be selected from structures of the formulae (Q-1), (Q-2), (Q-4), (Q-4), (Q-5), (Q-6), (Q-7), (Q-8), (Q-9) and/or (Q-10)

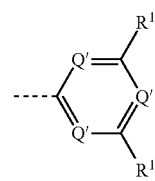

Formula (Q-1)

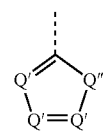

Formula (Q-2)

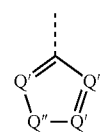

Formula (Q-3)

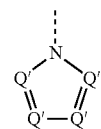

Formula (Q-4)

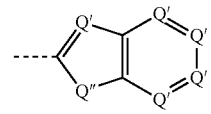

Formula (Q-5)

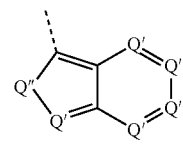

Formula (Q-6)

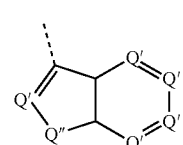

Formula (Q-7)

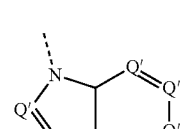

Formula (Q-8)

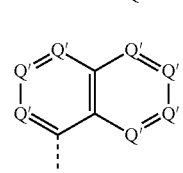

Formula (Q-9)

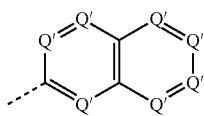

Formula (Q-10)

where the dotted bond marks the position of attachment,

Q' is the same or different at each instance and is $CR^1$ or N, and

Q" is $NR^1$, O or S;

where at least one Q' is N and $R^1$ is as defined above, especially in formula (I).

In addition, the Q group shown in the formula (QL) inter alia, or the electron transport group, may preferably be selected from a structure of the formulae (Q-11), (Q-12), (Q-13), (Q-14) and/or (Q-15)

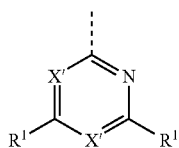

Formula (Q-11)

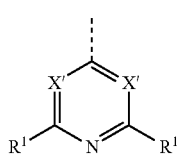

Formula (Q-12)

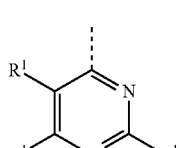

Formula (Q-13)

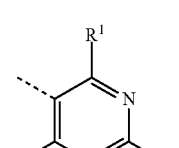

Formula (Q-14)

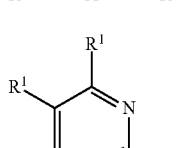

Formula (Q-15)

where the symbol $R^1$ has the definition given above for formula (I) inter alia, X is N or $CR^1$ and the dotted bond marks the position of attachment, where X is preferably a nitrogen atom.

In a further embodiment, the Q group shown in the formula (QL) inter alia, or the electron transport group, may be selected from structures of the formulae (Q-16), (Q-17), (Q-18), (Q-19), (Q-20), (Q-21) and/or (Q-22)

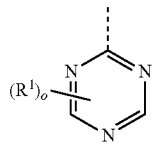

Formula (Q-16)

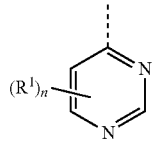

Formula (Q-17)

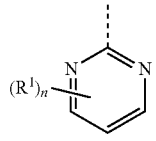

Formula (Q-18)

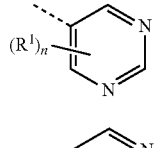

Formula (Q-19)

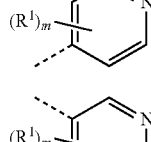

Formula (Q-20)

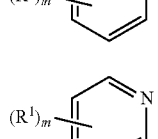

Formula (Q-21)

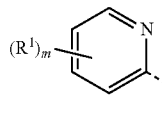

Formula (Q-22)

in which the symbol $R^1$ has the definition detailed above for formula (I) inter alia, the dotted bond marks the position of attachment and m is 0, 1, 2, 3 or 4, preferably 0, 1 or 2, n is 0, 1, 2 or 3, preferably 0, 1 or 2, and o is 0, 1 or 2, preferably 1 or 2. Preference is given here to the structures of the formulae (Q-16), (Q-17), (Q-18) and (Q-19).

In a further embodiment, the Q group shown in the formula (QL) inter alia, or the electron transport group, may be selected from structures of the formulae (Q-23), (Q-24) and/or (Q-25)

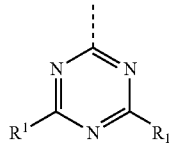

Formula (Q-23)

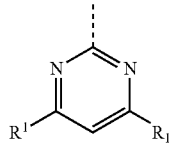

Formula (Q-24)

Formula (Q-25)

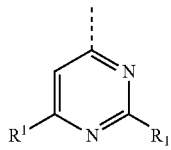

in which the symbol R¹ has the definition set out above for formula (I) inter alia, and the dotted bond marks the position of attachment.

In a further embodiment, the Q group shown in the formula (QL) inter alia, or the electron transport group, may be selected from structures of the formulae (Q-26), (Q-27), (Q-28), (Q-29) and/or (Q-30)

Formula (Q-26)

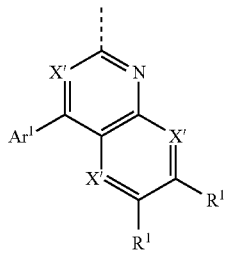

Formula (Q-27)

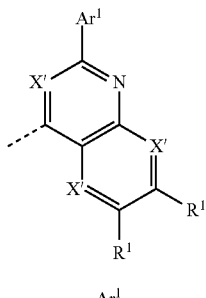

Formula (Q-28)

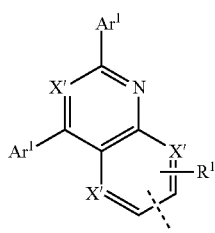

Formula (Q-29)

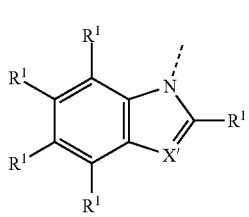

Formula (Q-30)

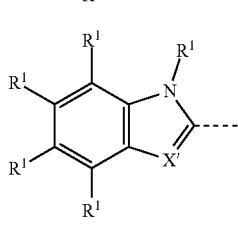

where symbols Ar¹ and R¹ have the definition given above for formula (I) to inter alia, X is N or CR¹ and the dotted bond marks the position of attachment. Preferably, in the structures of the formulae (Q-26), (Q-27) and (Q-28), exactly one X is a nitrogen atom.

Preferably, the Q group shown in the formula (QL) inter alia, or the electron transport group, may be selected from structures of the formulae (Q-31), (Q-32), (Q-33), (Q-34), (Q-35), (Q-36), (Q-37), (Q-38), (Q-39), (Q-40), (Q-41), (Q-42), (Q-43) and/or (Q-44)

Formula (Q-31)

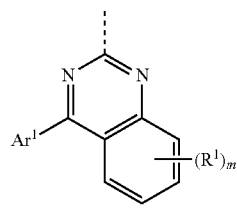

Formula (Q-32)

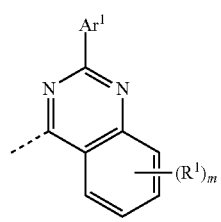

Formula (Q-33)

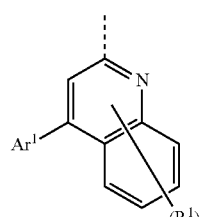

Formula (Q-34)

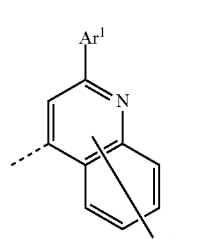

Formula (Q-35)

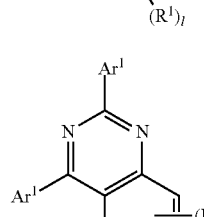

Formula (Q-36)

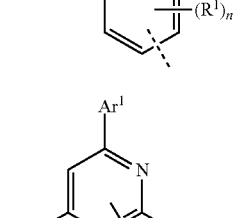

Formula (Q-37)
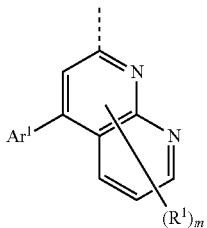

Formula (Q-38)
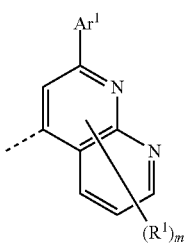

Formula (Q-39)
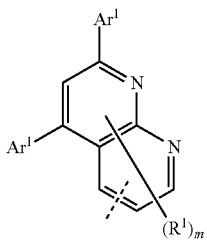

Formula (Q-40)
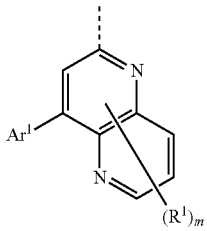

Formula (Q-41)
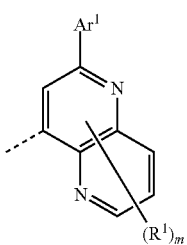

Formula (Q-42)
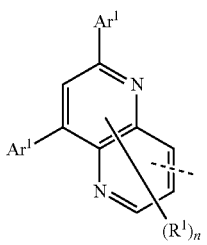

Formula (Q-43)
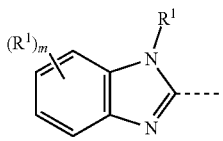

Formula (Q-44)
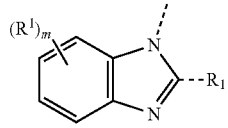

in which the symbols $Ar^1$ and $R^1$ have the definition set out above for formula (I) inter alia, the dotted bond marks the position of attachment and m is 0, 1, 2, 3 or 4, preferably 0, 1 or 2, n is 0, 1, 2 or 3, preferably 0 or 1, n is 0, 1, 2 or 3, preferably 0, 1 or 2, and l is 1, 2, 3, 4 or 5, preferably 0, 1 or 2.

In a further preferred embodiment of the invention, $Ar^1$ is the same or different at each instance and is an aromatic or heteroaromatic ring system, preferably an aryl or heteroaryl radical having 5 to 24 aromatic ring atoms, preferably having 6 to 18 aromatic ring atoms, and is more preferably an aromatic ring system, preferably an aryl radical having 6 to 12 aromatic ring atoms, or a heteroaromatic ring system, preferably a heteroaryl group having 5 to 13 aromatic ring atoms, each of which may be substituted by one or more $R^2$ radicals, but is preferably unsubstituted, where $R^2$ may have the definition detailed above, especially in formula (I).

Preferably, the symbol $Ar^1$ is an aryl or heteroaryl radical, such that an aromatic or heteroaromatic group of an aromatic or heteroaromatic ring system is bonded directly, i.e. via an atom of the aromatic or heteroaromatic group, to the respective atom of the further group, for example a carbon or nitrogen atom of the (H-1) to (H-26) or (Q-26) to (Q-44) groups shown above.

Advantageously, $Ar^1$ in the formulae (H-1) to (H-26) or (Q-26) to (Q-44) is an aromatic ring system which has 6 to 12 aromatic ring atoms and may be substituted by one or more $R^2$ radicals, but is preferably unsubstituted, where $R^2$ may have the definition detailed above, especially for formula (I).

Preferably, the $R^1$ or $R^2$ radicals in the formulae (H-1) to (H-26) or (Q-1) to (Q-44) do not form a fused ring system with the ring atoms of the aryl group or heteroaryl group $Ar^1$, $Ar^2$, $Ar^3$ and/or $Ar^4$ to which the $R^1$ or $R^2$ radicals are bonded. This includes the formation of a fused ring system with possible substituents $R^2$, $R^3$ which may be bonded to the $R^1$ or $R^2$ radicals.

It may also be the case that the Ar, $Ar^1$, $Ar^2$, $Ar^3$ and/or $Ar^4$ group is selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl, pyrenyl, triazinyl, imidazolyl, benzimidazolyl, benzoxazolyl, benzothiazolyl, 1-, 2-, 3- or 4-carbazolyl, indenocarbazolyl, 1- or 2-naphthyl, anthracenyl, preferably 9-anthracenyl, phenanthrenyl and/or triphenylenyl, each of which may be substituted by one or more $R^1$ and/or $R^2$ radicals, but are preferably unsubstituted, particular preference being given to phenyl, spirobifluorene, fluorene, dibenzofuran, dibenzothiophene, anthracene, phenanthrene, triphenylene groups.

In a preferred embodiment, it may be the case that at least two R and/or $R^a$ radicals in a structure of the formulae (I), (II), (IIIa), (IIIb), (IIIc), (IVa), (IVb), (IVc) and/or (V) each comprise and preferably are a hole transport group, where preferably two $R^a$ radicals each comprise and preferably are a hole transport group.

It may further be the case that at least one of the R and/or $R^a$ radicals in a structure of the formulae (I), (II), (IIIa), (IIIb), (IIIc), (IVa), (IVb), (IVc) and/or (V) comprises two hole transport groups. A hole transport group may be regarded here as the $R^1$ radical, in which case the substituents $R^1$ in the structures of the formulae (H-1) to (H-26) should be replaced by $R^2$ radicals.

In a preferred embodiment, it may be the case that at least two R and/or $R^a$ radicals in a structure of the formulae (I), (II), (IIIa), (IIIb), (IIIc), (IVa), (IVb), (IVc) and/or (V) each comprise and preferably are an electron transport group-comprising radical, where preferably two $R^a$ radicals each comprise and preferably are an electron transport group-comprising radical.

It may further be the case that at least one of the R and/or $R^a$ radicals in a structure of the formulae (I), (II), (IIIa), (IIIb), (IIIc), (IVa), (IVb), (IVc) and/or (V) comprises two electron transport group-comprising radicals. An electron transport group-comprising radical may be regarded here as the $R^1$ radical, in which case the substituents $R^1$ in the structures of the formulae (Q-1) to (Q-44) should be replaced by $R^2$ radicals.

In a further configuration, it may be the case that at least one of the R and/or $R^a$ radicals in a structure of the formulae (I), (II), (IIIa), (IIIb), (IIIc), (IVa), (IVb), (IVc) and/or (V) comprises and preferably is a hole transport group, and at least one of the R and/or $R^a$ radicals comprises and preferably is an electron transport group-comprising radical, where preferably one of the $R^a$ radicals comprises and preferably is a hole transport group, and at least one of the $R^a$ radicals comprises and preferably is an electron transport group-comprising radical.

It may further be the case that at least one of the R and/or $R^a$ radicals in a structure of the formulae (I), (II), (IIIa), (IIIb), (IIIc), (IVa), (IVb), (IVc) and/or (V) comprises both an electron transport group-comprising radical and a hole transport group. An electron transport group-comprising radical or a hole transport group may be regarded here as the $R^1$ radical, in which case the substituents $R^1$ in the structures of the formulae (Q-1) to (Q-44) or (H-1) to (H-26) should be replaced by $R^2$ radicals.

In a further configuration, it may be the case that at least one of the R and/or $R^a$ radicals comprises at least one group that leads to with wide bandgap materials. The expression "group that leads to with wide bandgap materials" sets out that the compounds can be used as wide bandgap materials, and so the compounds have corresponding groups. Wide bandgap materials are discussed in detail later on.

It may further be the case that at least one of the R and/or $R^a$ radicals comprises at least one group that leads to materials that are used as host material. The expression "group that leads to materials that are used as host material" sets out that the compounds can be used as host materials, and so the compounds have corresponding groups. Host materials will be discussed in detail later on.

In a further configuration, it may be the case that the compound usable as active compound an organic electronic device comprises a fused aromatic or heteroaromatic ring system having at least 2, preferably three, fused rings that may optionally be substituted.

Preferably, at least one of the R and/or $R^a$ radicals in structures of the formulae (I), (II), (IIIa), (IIIb), (IIIc), (IVa), (IVb), (IVc) and/or (V) comprises at least one aromatic or heteroaromatic ring system having two, preferably having three, fused aromatic or heteroaromatic rings.

It may preferably be the case that the aromatic or heteroaromatic ring system having two, preferably having three, fused aromatic or heteroaromatic rings is selected from the groups of the formulae (Ar-1) to (Ar-11)

(Ar-1)

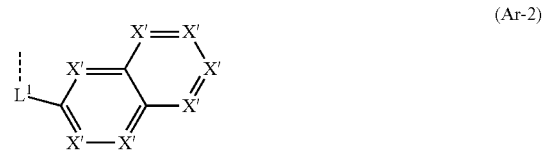

(Ar-2)

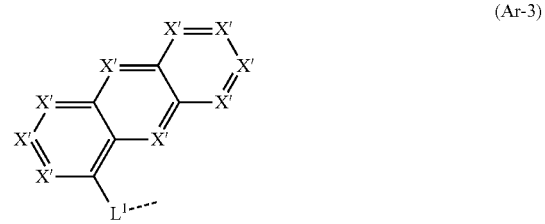

(Ar-3)

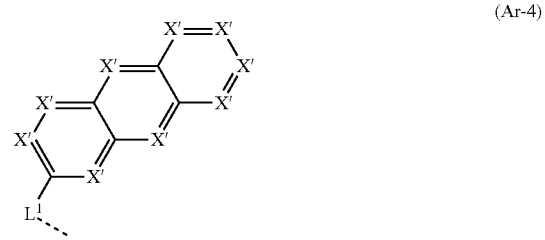

(Ar-4)

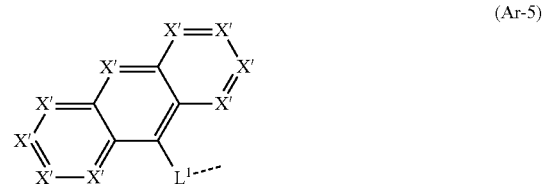

(Ar-5)

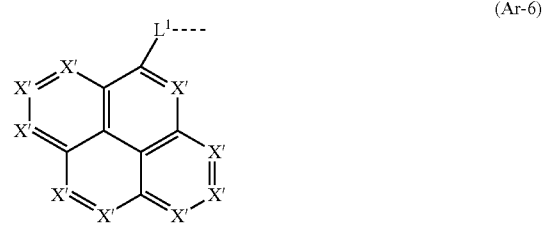

(Ar-6)

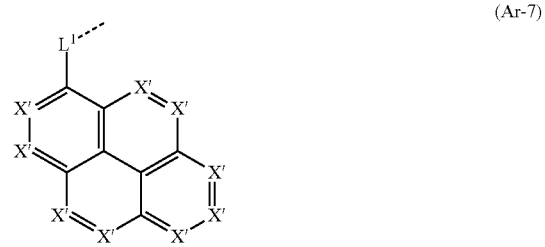

(Ar-7)

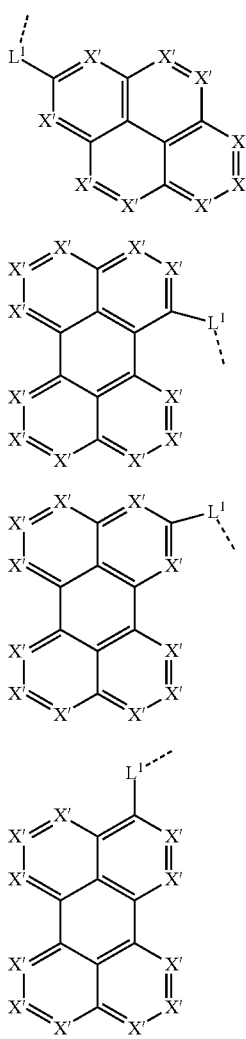

(Ar-8)

(Ar-9)

(Ar-10)

(Ar-11)

where X' is N or CR$^1$, preferably CR$^1$, L$^1$ represents a bond or an aromatic or heteroaromatic ring system which has 5 to 40, preferably 5 to 30, aromatic ring atoms and may be substituted by one or more R$^1$ radicals, where R$^1$ has the definition set out above, especially for formula (I), and the dotted bond marks the position of attachment.

It may most preferably be the case that the aromatic or heteroaromatic ring system having two, preferably having three, fused aromatic or heteroaromatic rings is selected from the groups of the formulae (Ar'-1) to (Ar'-11)

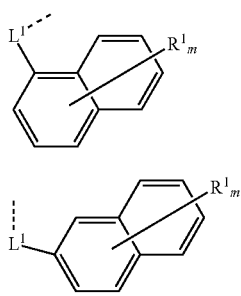

(Ar'-1)

(Ar'-2)

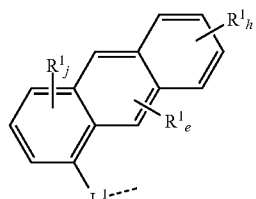

(Ar'-3)

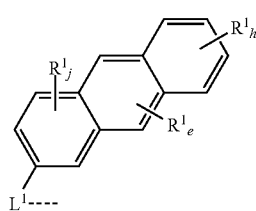

(Ar'-4)

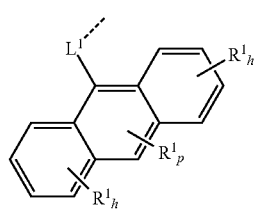

(Ar'-5)

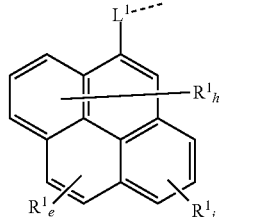

(Ar'-6)

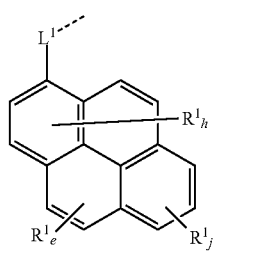

(Ar'-7)

(Ar'-8)

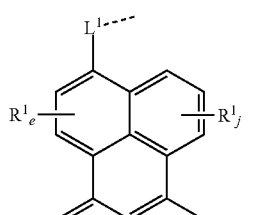

(Ar'-9)

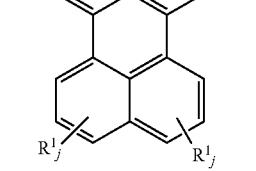

-continued

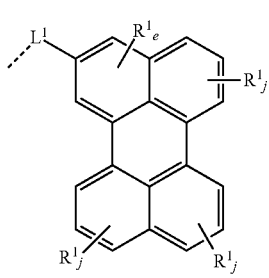

(Ar'-10)

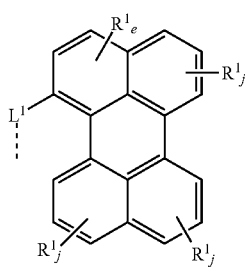

(Ar'-11)

where $L^1$ represents a bond or an aromatic or heteroaromatic ring system which has 5 to 40, preferably 5 to 30, aromatic ring atoms and may be substituted by one or more $R^1$ radicals, where $R^1$ has the definition set out above, especially for formula (I), the dotted bond marks the position of attachment and the indices are as follows:

p is 0 or 1;
e is 0, 1 or 2, preferably 0 or 1;
j at each instance is independently 0, 1, 2 or 3, preferably 0, 1 or 2, more preferably 0 or 1;
h at each instance is independently 0, 1, 2, 3 or 4, preferably 0, 1 or 2, more preferably 0 or 1;
i at each instance is independently 0, 1 or 2;
m is an integer in the range from 0 to 7, preferably 0, 1, 2, 3, 4, 5 or 6, particularly preferably 0, 1, 2, 3 or 4, especially preferably 0, 1 or 2.

It is preferable that the sum total of the indices p, e, i, j, h and m in the structures of the formula (Ar'-1) to (Ar'-11) in each case is not more than 3, preferably not more than 2 and more preferably not more than 1.

When X or $X^1$ is $CR^1$ or when the aromatic and/or heteroaromatic groups are substituted by substituents $R^1$, these substituents $R^1$ are preferably selected from the group consisting of H, D, F, CN, $N(Ar^1)_2$, $C(=O)Ar^1$, $P(=O)(Ar^1)_2$ a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more $R^2$ radicals, where one or more nonadjacent $CH_2$ groups may be replaced by O and where one or more hydrogen atoms may be replaced by D or F, an aromatic or heteroaromatic ring system which has 5 to 24 aromatic ring atoms and may be substituted in each case by one or more $R^2$ radicals, but is preferably unsubstituted, or an aralkyl or heteroaralkyl group which has 5 to 25 aromatic ring atoms and may be substituted by one or more $R^2$ radicals; at the same time, it is optionally possible for two substituents $R^1$ preferably bonded to adjacent carbon atoms to form a monocyclic or polycyclic, aliphatic, aromatic or heteroaromatic ring system which may be substituted by one or more $R^1$ radicals; where the $Ar^1$ group has the definition given above, especially for formula (I).

More preferably, these substituents $R^1$ are selected from the group consisting of H, D, F, CN, $N(Ar^1)_2$, a straight-chain alkyl group having 1 to 8 carbon atoms, preferably having 1, 2, 3 or 4 carbon atoms, or a branched or cyclic alkyl group having 3 to 8 carbon atoms, preferably having 3 or 4 carbon atoms, or an alkenyl group having 2 to 8 carbon atoms, preferably having 2, 3 or 4 carbon atoms, each of which may be substituted by one or more $R^2$ radicals, but is preferably unsubstituted, or an aromatic or heteroaromatic ring system which has 5 to 24 aromatic ring atoms, preferably 6 to 18 aromatic ring atoms, more preferably 6 to 13 aromatic ring atoms, and may be substituted in each case by one or more nonaromatic $R^1$ radicals, but is preferably unsubstituted; at the same time, two substituents $R^1$ preferably bonded to adjacent carbon atoms may optionally form a monocyclic or polycyclic aliphatic ring system which may be substituted by one or more $R^2$ radicals, but is preferably unsubstituted, where $Ar^1$ may have the definition set out above.

Most preferably, the substituents $R^1$ are selected from the group consisting of H or an aromatic or heteroaromatic ring system which has 6 to 18 aromatic ring atoms, preferably 6 to 13 aromatic ring atoms, and may be substituted in each case by one or more nonaromatic $R^2$ radicals, but is preferably unsubstituted. Examples of suitable substituents $R^1$ are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl, 1-, 2-, 3- or 4-carbazolyl and indenocarbazolyl, each of which may be substituted by one or more $R^2$ radicals, but are preferably unsubstituted.

It may further be the case that the substituents $R^1$ of an aromatic or heteroaromatic ring system do not form a fused aromatic or heteroaromatic ring system, preferably any fused ring system, with further ring atoms of the aromatic or heteroaromatic ring system. This includes the formation of a fused ring system with possible substituents $R^2$, $R^3$ which may be bonded to the $R^1$ radicals.

It may further be the case that at least one $R^1$ or $Ar^1$ radical in a structure of formula (I), (II), (IIIa), (IIIb), (IIIc), (IVa), (IVb), (IVc) and/or (V) is a group selected from the formulae ($R^1$-1) to ($R^1$-92), or at least one $Ar^1$ or $R^1$ radical in a structure of formula (H-1) to (H-26), (QL), (Q-1) to (Q-44), (Ar-1) to (Ar-11) and/or (Ar'-1) to (Ar'-11) is a group selected from the formulae ($R^1$-1) to ($R^1$-92)

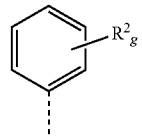

Formula ($R^1$-1)

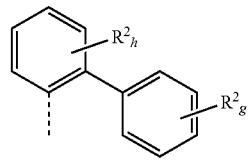

Formula ($R^1$-2)

Formula (R¹-3)
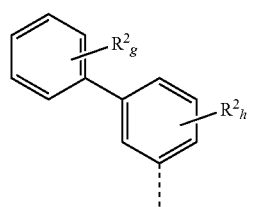
Formula (R¹-4)
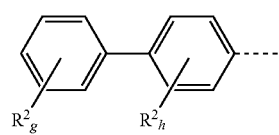
Formula (R¹-5)
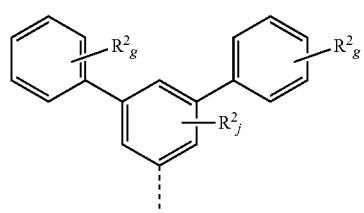
Formula (R¹-6)
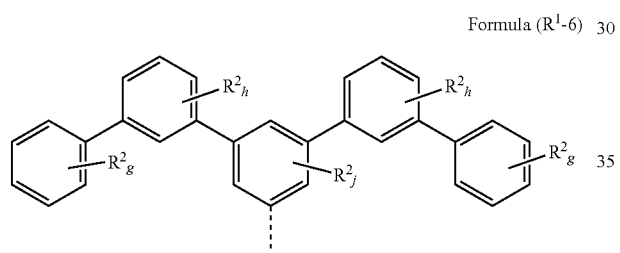
Formula (R¹-7)
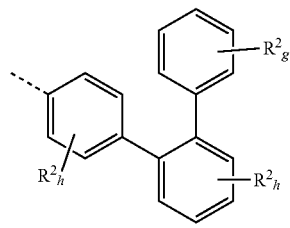
Formula (R¹-8)
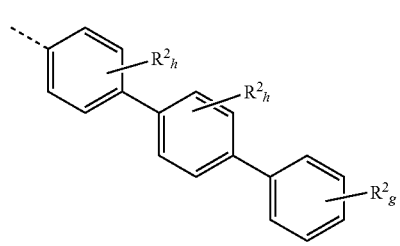
Formula (R¹-9)
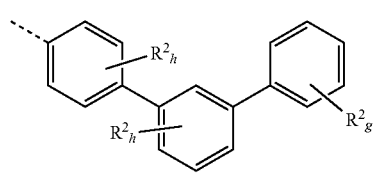
Formula (R¹-10)
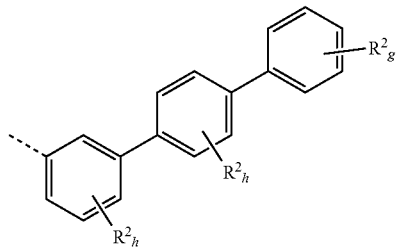
Formula (R¹-11)
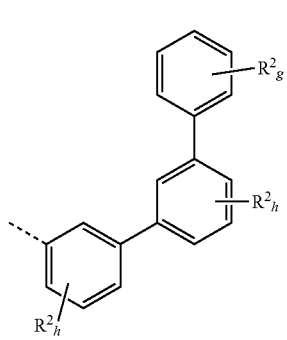
Formula (R¹-12)
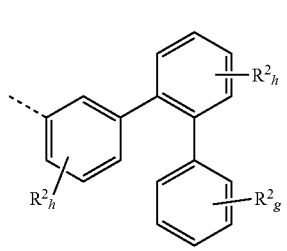
Formula (R¹-13)
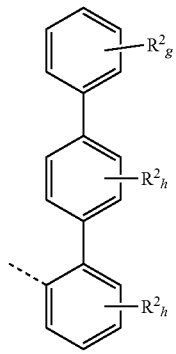
Formula (R¹-14)
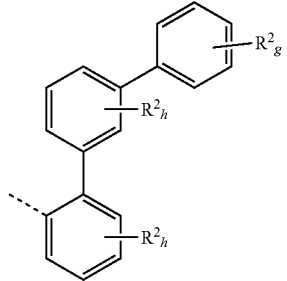

Formula (R¹-15)
Formula (R¹-16)
Formula (R¹-17)
Formula (R¹-18)
Formula (R¹-19)
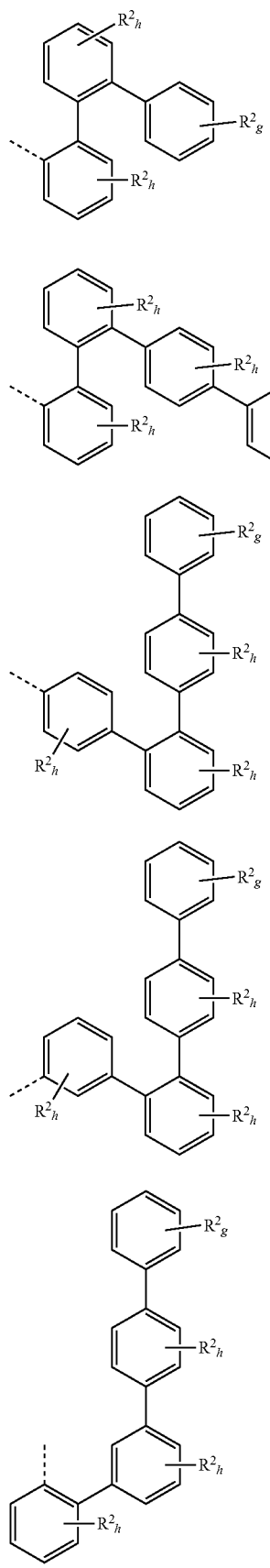
Formula (R¹-20)
Formula (R¹-21)
Formula (R¹-22)
Formula (R¹-23)
Formula (R¹-24)
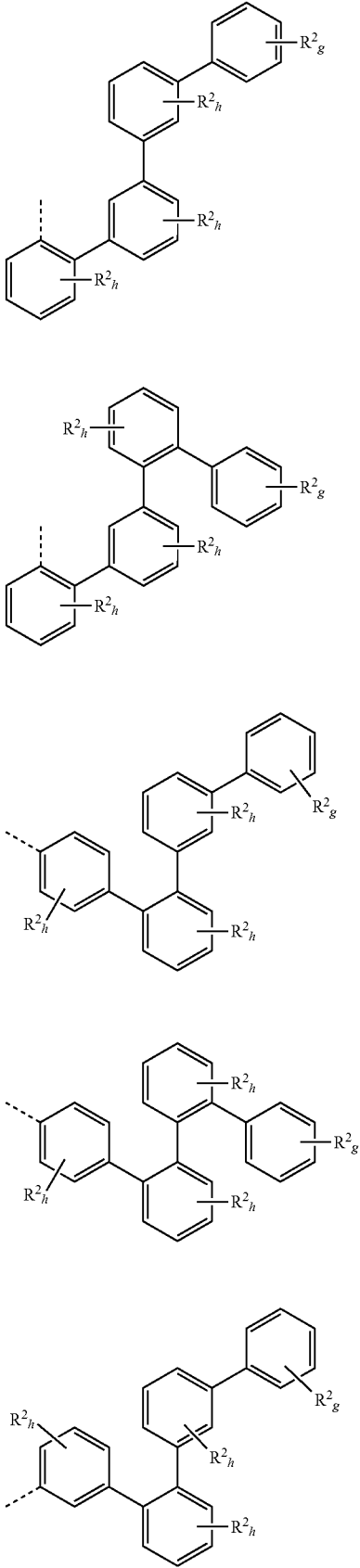

Formula (R¹-25)
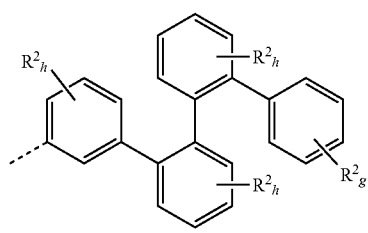
Formula (R¹-26)
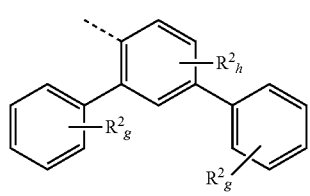
Formula (R¹-27)
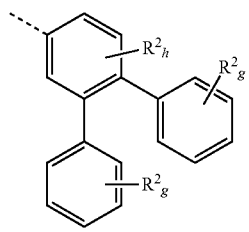
Formula (R¹-28)
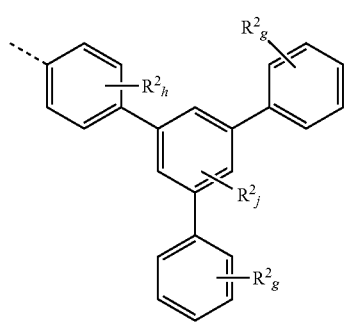
Formula (R¹-29)
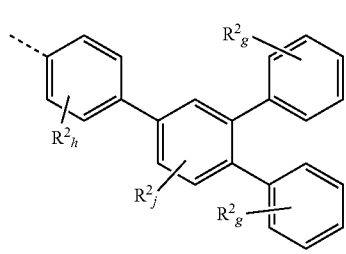
Formula (R¹-30)
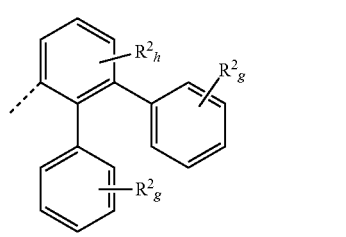
Formula (R¹-31)
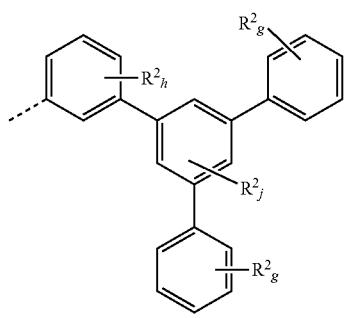
Formula (R¹-32)
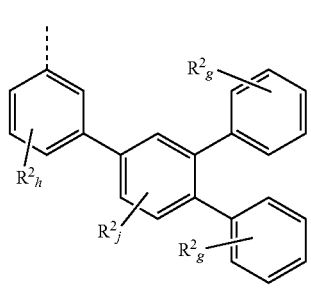
Formula (R¹-33)
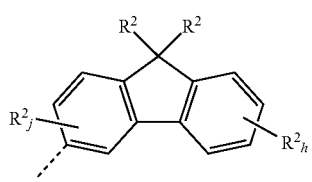
Formula (R¹-34)
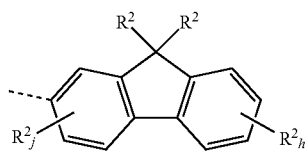
Formula (R¹-35)
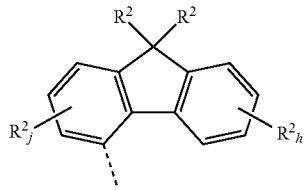
Formula (R¹-36)
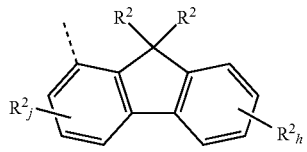
Formula (R¹-37)
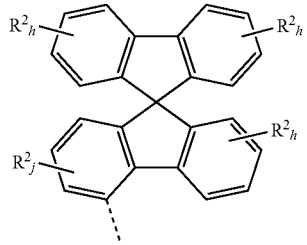

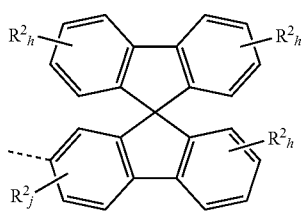
Formula (R¹-38)
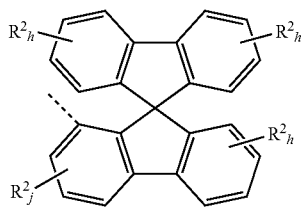
Formula (R¹-39)
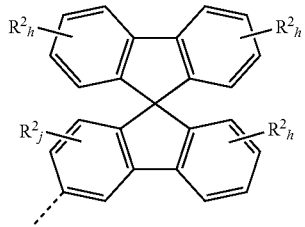
Formula (R¹-40)
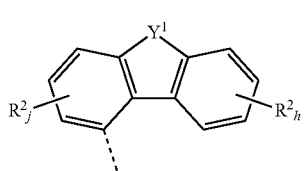
Formula (R¹-41)
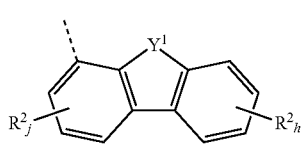
Formula (R¹-42)
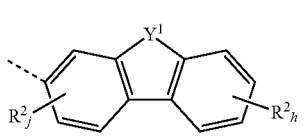
Formula (R¹-43)
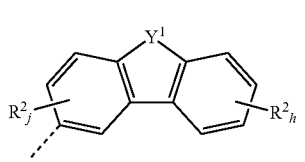
Formula (R¹-44)
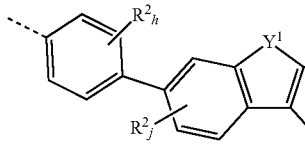
Formula (R¹-45)
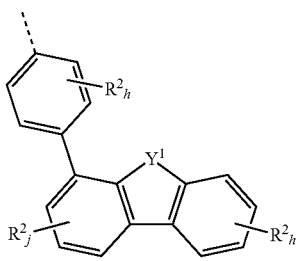
Formula (R¹-46)
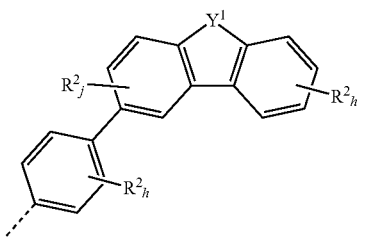
Formula (R¹-47)
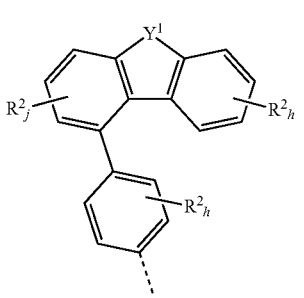
Formula (R¹-48)
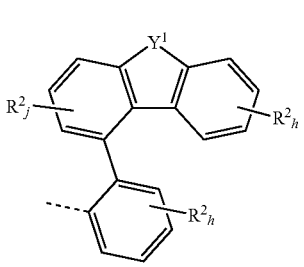
Formula (R¹-49)
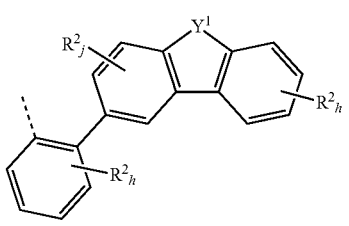
Formula (R¹-50)
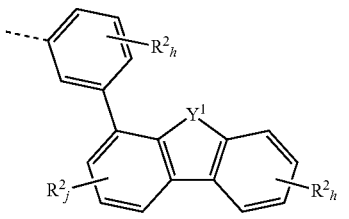
Formula (R¹-51)

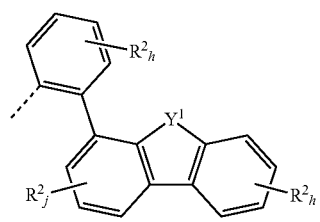
Formula (R¹-52)
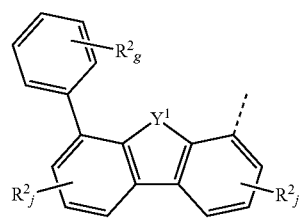
Formula (R¹-53)
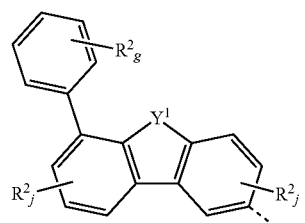
Formula (R¹-54)
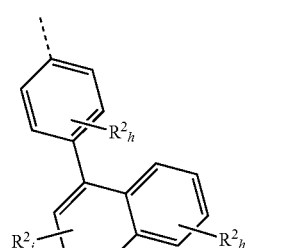
Formula (R¹-55)
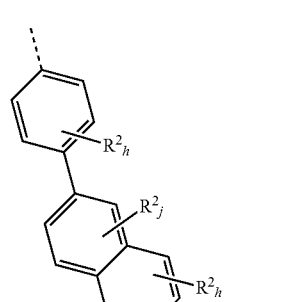
Formula (R¹-56)
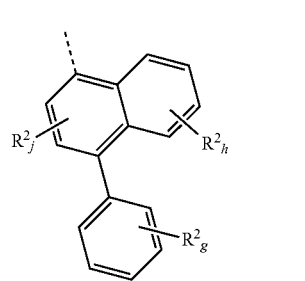
Formula (R¹-57)
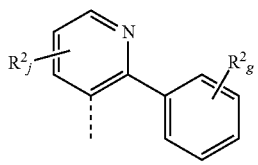
Formula (R¹-58)
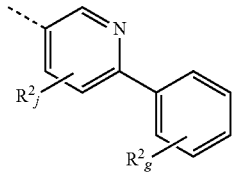
Formula (R¹-59)
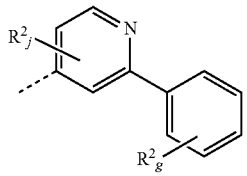
Formula (R¹-60)
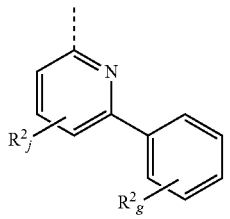
Formula (R¹-61)
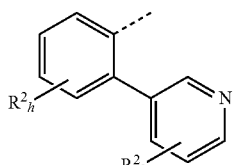
Formula (R¹-62)
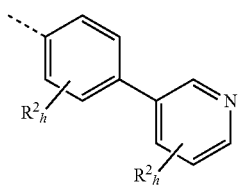
Formula (R¹-63)
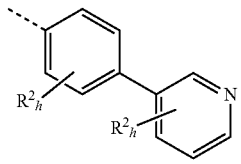
Formula (R¹-64)
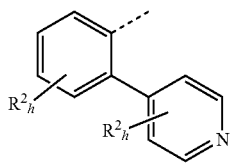
Formula (R¹-65)

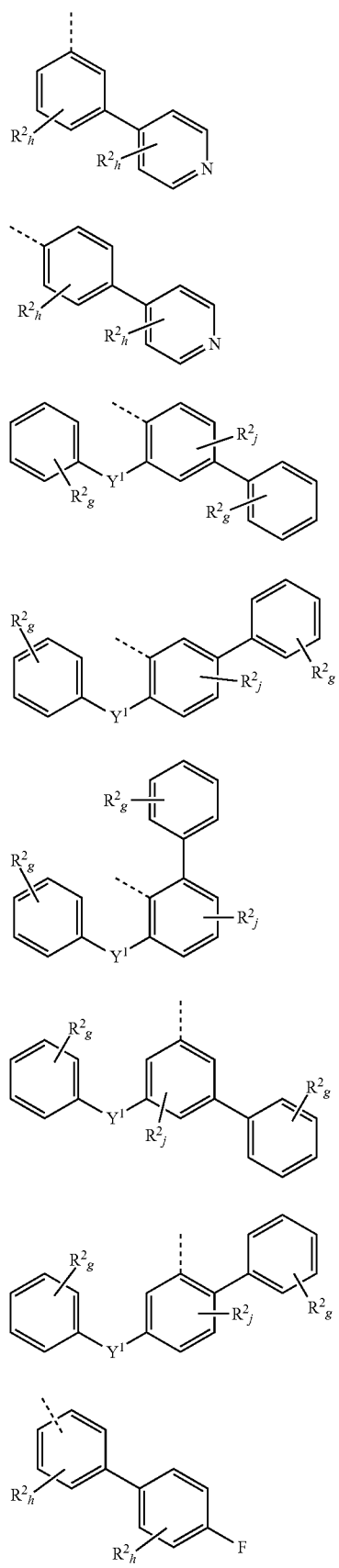
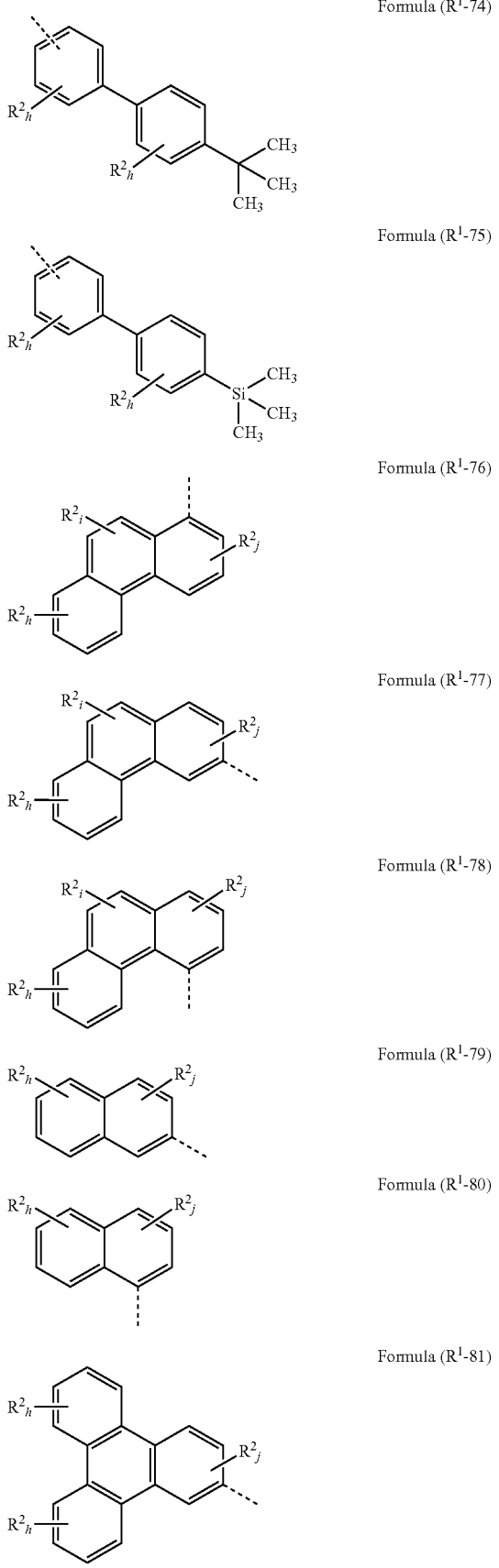

Formula (R¹-82)
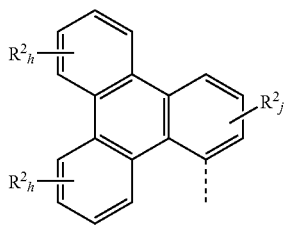

Formula (R¹-83)
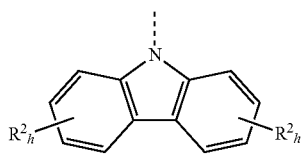

Formula (R¹-84)
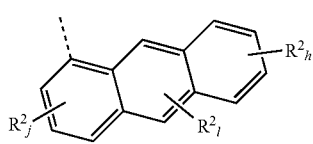

Formula (R¹-85)
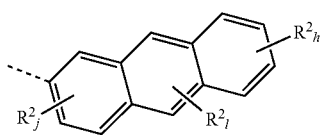

Formula (R¹-86)
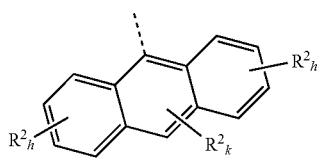

Formula (R¹-87)
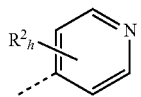

Formula (R¹-88)
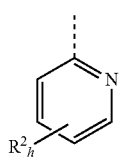

Formula (R¹-89)
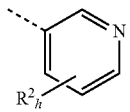

Formula (R¹-90)
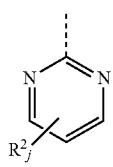

Formula (R¹-91)
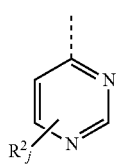

Formula (R¹-92)
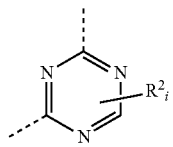

where the symbols used are as follows:
Y¹ is O, S or NR², preferably O or S;
k at each instance is independently 0 or 1;
i at each instance is independently 0, 1 or 2;
j at each instance is independently 0, 1, 2 or 3;
h at each instance is independently 0, 1, 2, 3 or 4;
g at each instance is independently 0, 1, 2, 3, 4 or 5;
R² may have the definition given above, especially for formula (I), and the dotted bond marks the position of attachment.

Preference is given here to the groups of the formulae R¹-1 to R¹-54, particular preference to the R¹-1, R¹-3, R¹-5, R¹-6, R¹-15, R¹-29, R¹-30, R¹-31, R¹-32, R¹-33, R¹-38, R¹-39, R¹-40, R¹-41, R¹-42, R¹-43, R¹-44 and/or R¹-45 groups.

It may preferably be the case that the sum total of the indices k, i, j, h and g in the structures of the formula (R¹-1) to (R¹-92) in each case is not more than 3, preferably not more than 2 and more preferably not more than 1.

Preferably, the R² radicals in the formulae (R¹-1) to (R¹-92) do not form a fused aromatic or heteroaromatic ring system, and preferably do not form any fused ring system, with the ring atoms of the aryl group or heteroaryl group to which the R² radicals are bonded. This includes the formation of a fused ring system with possible substituents R³ which may be bonded to the R² radicals.

The above-detailed radicals of the formulae (R¹-1) to (R¹-92) are preferred Ar radicals of formula (I) or Ar³, Ar⁴ radicals of formulae (H-1) to (H-3) or preferred embodiments of these formulae, where, in this case, the R² groups shown in the formulae (R¹-1) to (R¹-92) are to be replaced by R¹ radicals. The preferences detailed above with regard to the formulae (R¹-1) to (R¹-92) are correspondingly applicable.

It may preferably be the case that the compound comprises at least one linking group selected from the formulae (L¹-1) to (L¹-108); preferably, in the structure of formulae (H-1) to (H-26), the Ar² group is selected from the formulae (L¹-1) to (L¹-108) or the electron transport group is linked to further structural elements via a linking group selected from the formulae (L¹-1) to (L¹-108), or the L¹ radical in formulae (QL), (Ar-1) to (Ar-11) and/or (Ar'-1) to (Ar'-11) is a group selected from the formulae (L¹-1) to (L¹-108)

Formula (L¹-1)
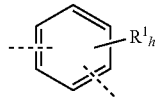

Formula (L¹-2)
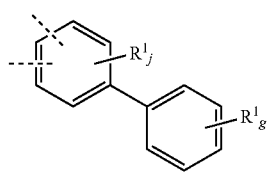

-continued
Formula (L¹-3)
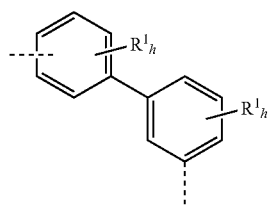
Formula (L¹-4)
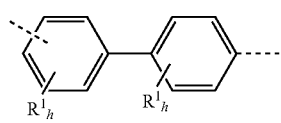
Formula (L¹-5)
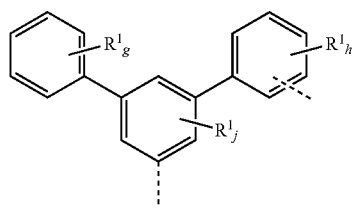
Formula (L¹-6)
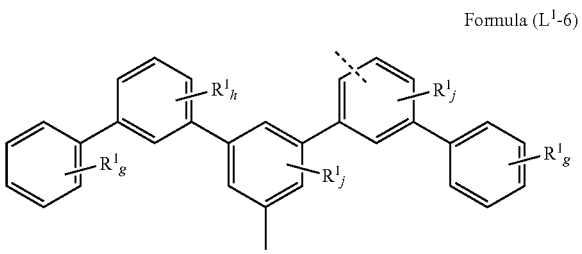
Formula (L¹-7)
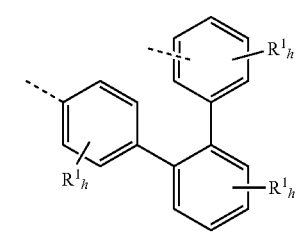
Formula (L¹-8)
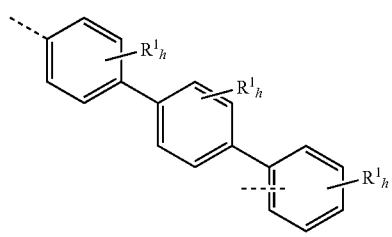
Formula (L¹-9)
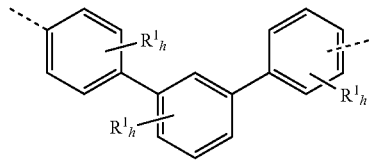
-continued
Formula (L¹-10)
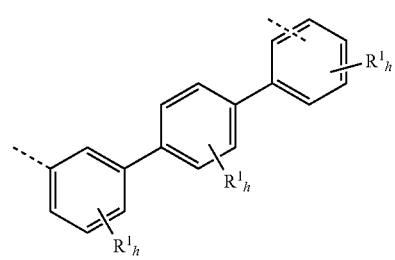
Formula (L¹-11)
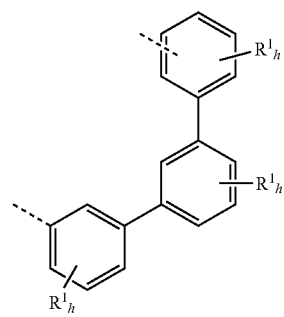
Formula (L¹-12)
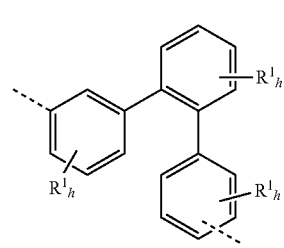
Formula (L¹-13)
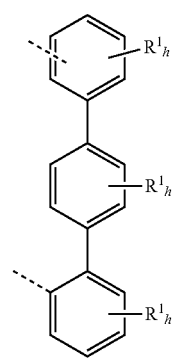
Formula (L¹-14)
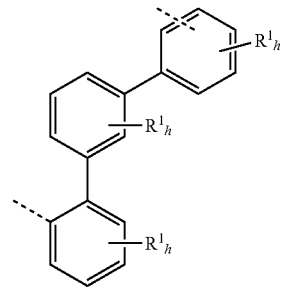

Formula (L¹-15)
Formula (L¹-16)
Formula (L¹-17)
Formula (L¹-18)
Formula (L¹-19)
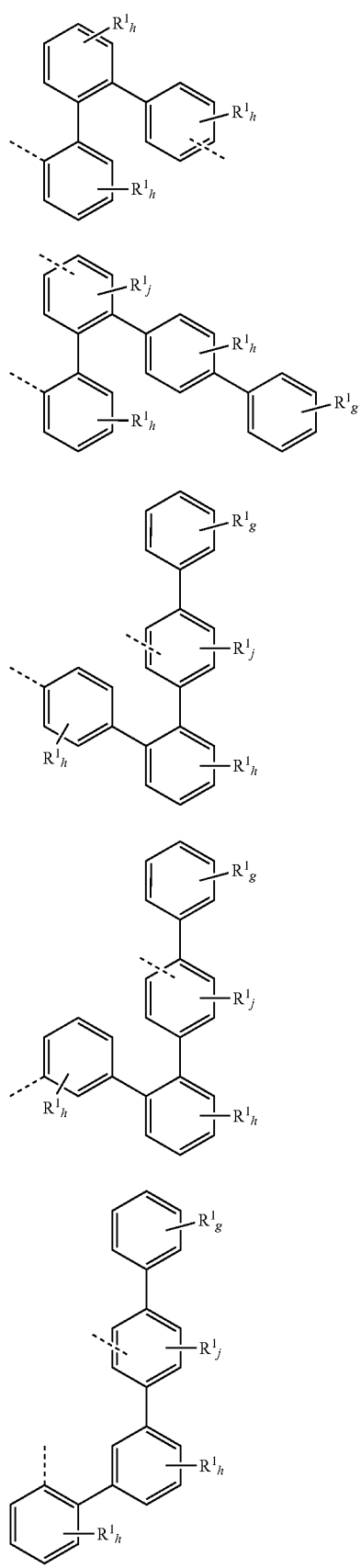
Formula (L¹-20)
Formula (L¹-21)
Formula (L¹-22)
Formula (L¹-23)
Formula (L¹-24)
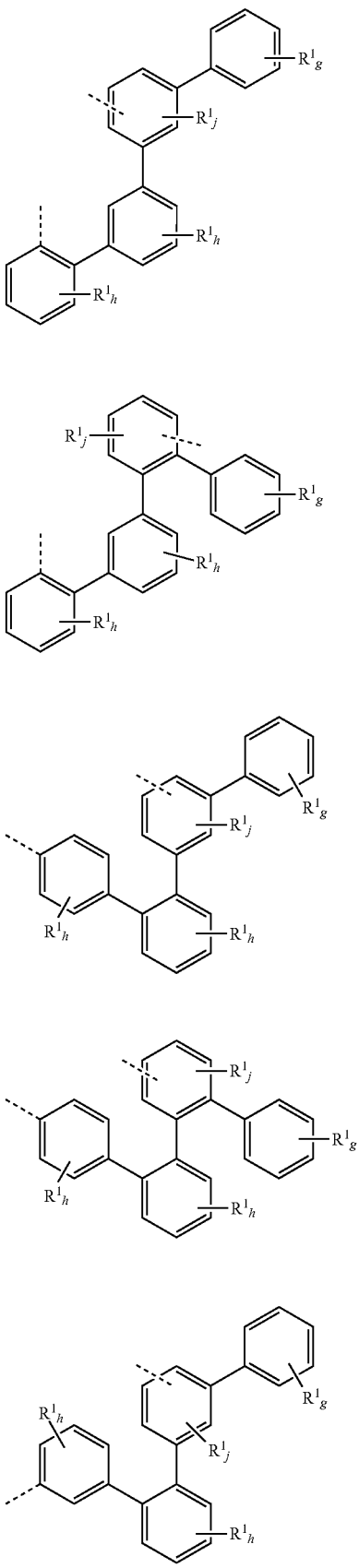

Formula (L¹-25)
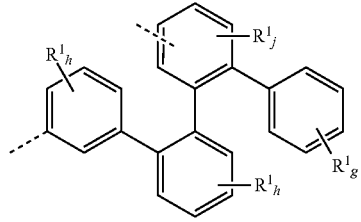
Formula (L¹-26)
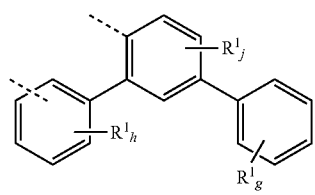
Formula (L¹-27)
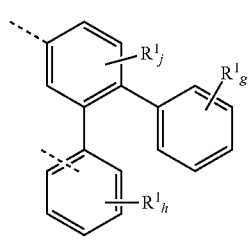
Formula (L¹-28)
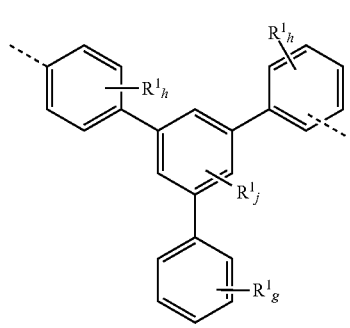
Formula (L¹-29)
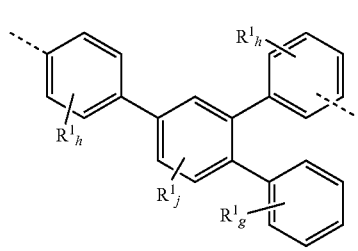
Formula (L¹-30)
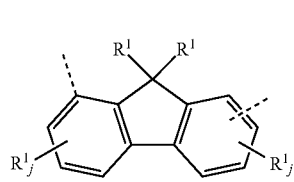
Formula (L¹-31)
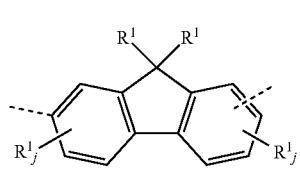
Formula (L¹-32)
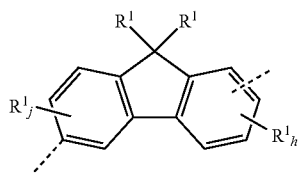
Formula (L¹-33)
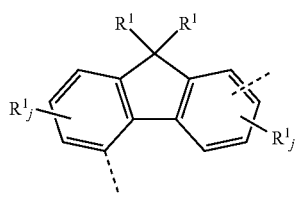
Formula (L¹-34)
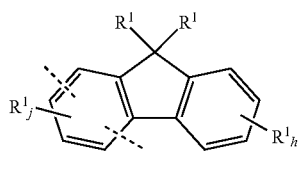
Formula (L¹-35)
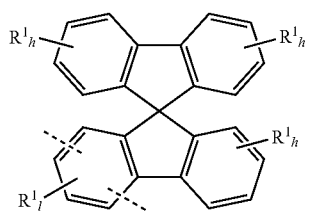
Formula (L¹-36)
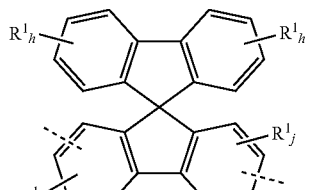
Formula (L¹-37)
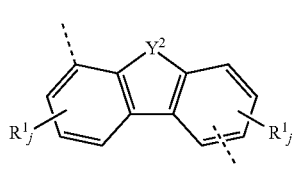
Formula (L¹-38)
Formula (L¹-39)
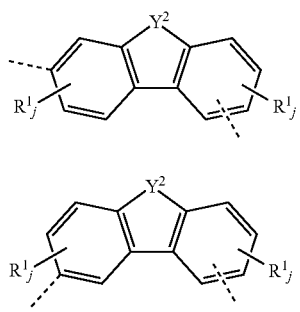

Formula (L¹-40)
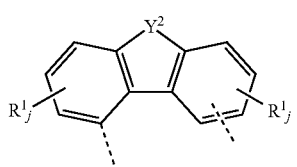
Formula (L¹-41)
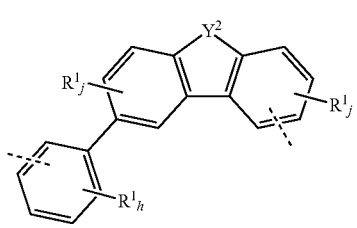
Formula (L¹-42)
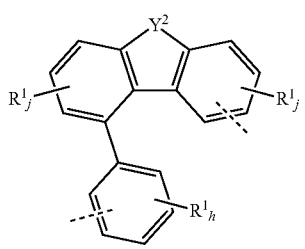
Formula (L¹-43)
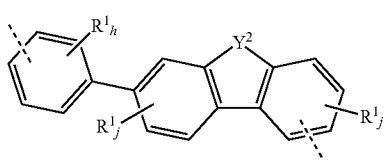
Formula (L¹-44)
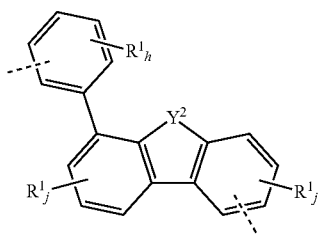
Formula (L¹-45)
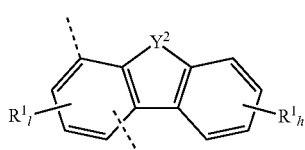
Formula (L¹-46)
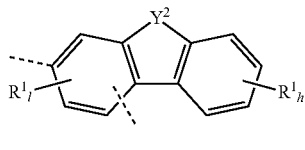
Formula (L¹-47)
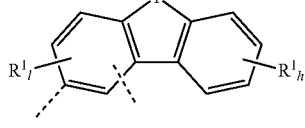
Formula (L¹-48)
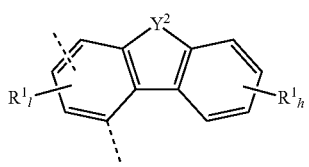
Formula (L¹-49)
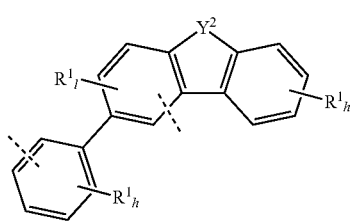
Formula (L¹-50)
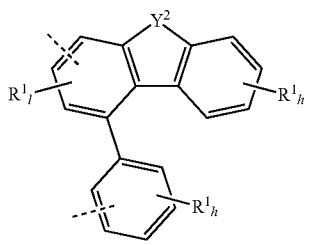
Formula (L¹-51)
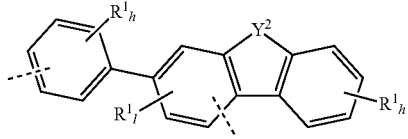
Formula (L¹-52)
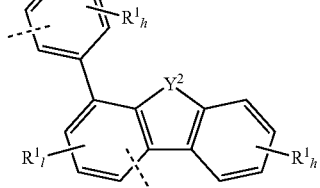
Formula (L¹-53)
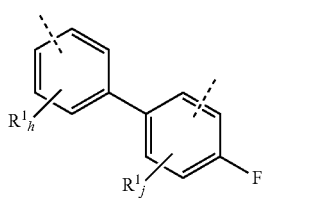
Formula (L¹-54)
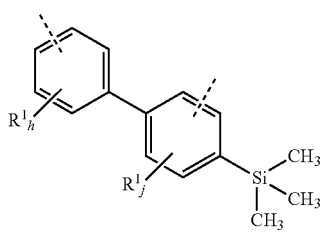

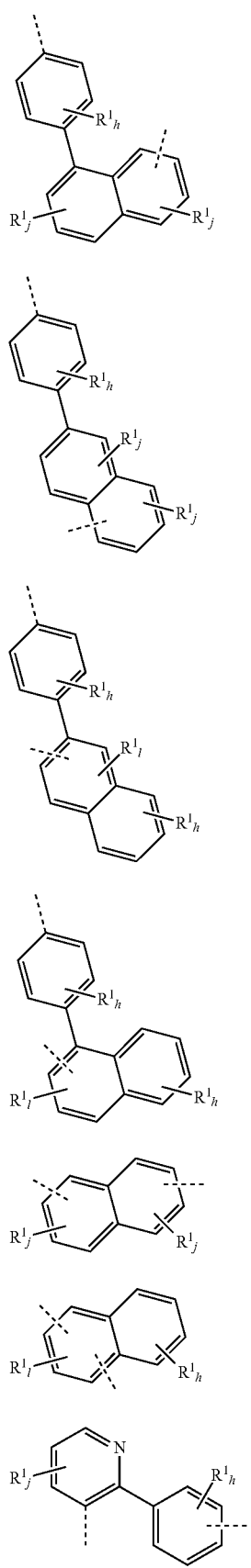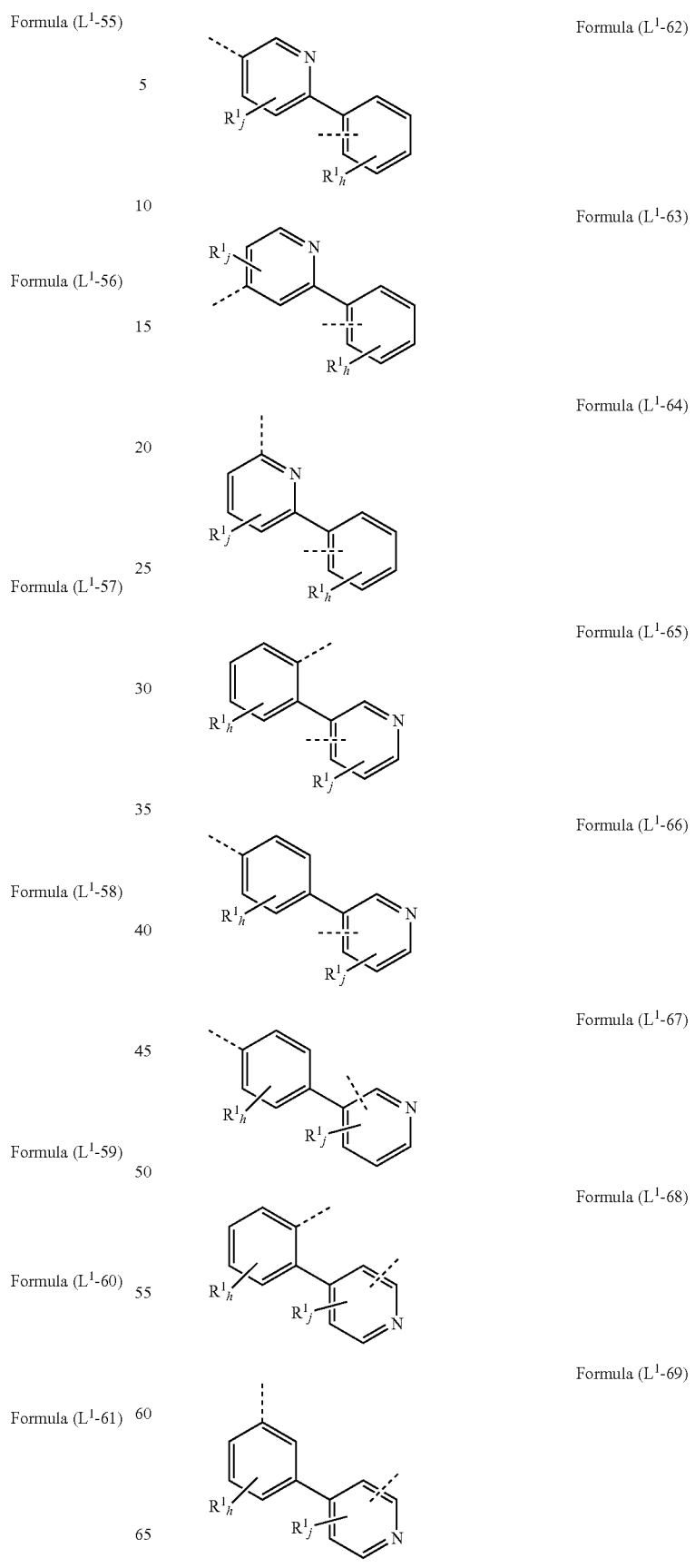

-continued

Formula (L¹-70)

Formula (L¹-71)

Formula (L¹-72)

Formula (L¹-73)

Formula (L¹-74)

Formula (L¹-75)

Formula (L¹-76)

Formula (L¹-77)

Formula (L¹-78)

Formula (L¹-79)

-continued

Formula (L¹-80)

Formula (L¹-81)

Formula (L¹-82)

Formula (L¹-83)

Formula (L¹-84)

Formula (L¹-85)

Formula (L¹-86)

Formula (L¹-87)

Formula (L¹-88)
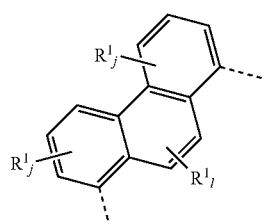
Formula (L¹-89)
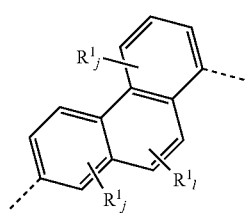
Formula (L¹-90)
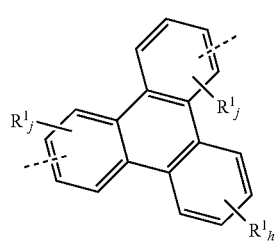
Formula (L¹-91)
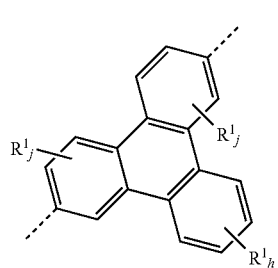
Formula (L¹-92)
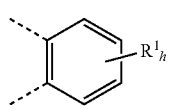
Formula (L¹-93)
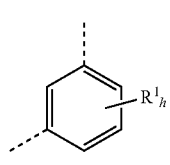
Formula (L¹-94)
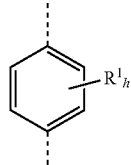
Formula (L¹-95)
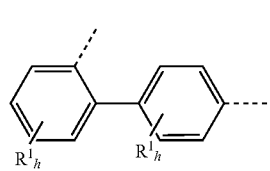
Formula (L¹-96)
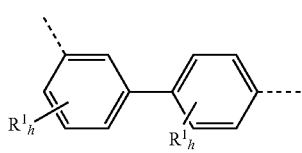
Formula (L¹-97)
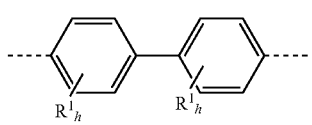
Formula (L¹-98)
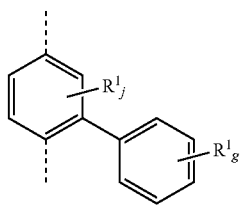
Formula (L¹-99)
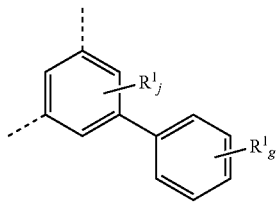
Formula (L¹-100)
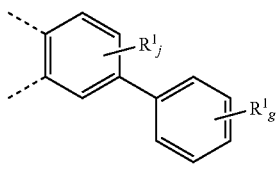
Formula (L¹-101)
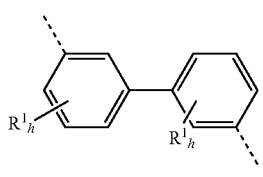
Formula (L¹-102)
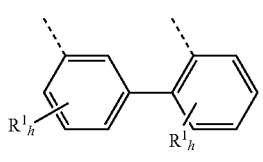
Formula (L¹-103)
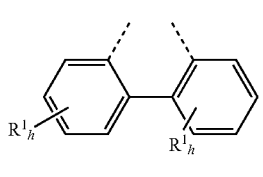
Formula (L¹-104)
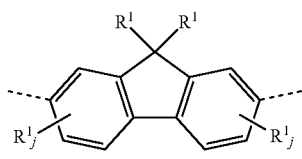

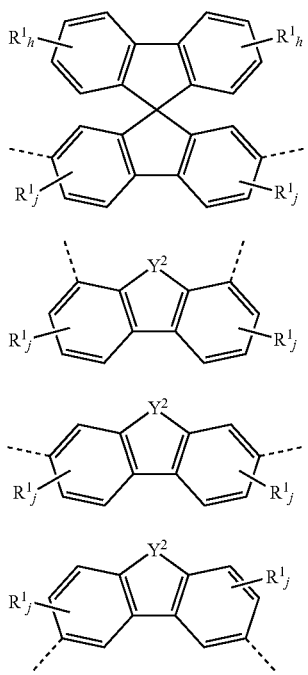

Formula (L¹-105)

Formula (L¹-106)

Formula (L¹-107)

Formula (L¹-108)

where the dotted bonds in each case mark the positions of attachment, the index k is 0 or 1, the index l is 0, 1 or 2, the index j at each instance is independently 0, 1, 2 or 3; the index h at each instance is independently 0, 1, 2, 3 or 4, the index g is 0, 1, 2, 3, 4 or 5; the symbol $Y^2$ is O, S or $NR^1$, preferably O or S; and the symbol $R^1$ has the definition given above, especially for formula (I).

It may preferably be the case that the sum total of the indices k, l, g, h and j in the structures of the formula (L¹-1) to (L¹-108) is at most 3 in each case, preferably at most 2 and more preferably at most 1.

Preferred compounds of the invention having a group of the formulae (H-1) to (H-26) comprise an $Ar^2$ group selected from one of the formulae (L¹-1) to (L¹-78) and/or (L¹-92) to (L¹-108), preferably of the formula (L¹-1) to (L¹-54) and/or (L¹-92) to (L¹-108), especially preferably of the formula (L¹-1) to (L¹-29) and/or (L¹-92) to (L¹-103). Advantageously, the sum total of the indices k, l, g, h and j in the structures of the formulae (L¹-1) to (L¹-78) and/or (L¹-92) to (L¹-108), preferably of the formula (L¹-1) to (L¹-54) and/or (L¹-92) to (L¹-108), especially preferably of the formula (L¹-1) to (L¹-29) and/or (L¹-92) to (L¹-103), may in each case be not more than 3, preferably not more than 2 and more preferably not more than 1.

Preferred compounds of the invention having a group of the formula (QL) comprise an $L^1$ group which represents a bond or which is selected from one of the formulae (L¹-1) to (L¹-78) and/or (L¹-92) to (L¹-108), preferably of the formula (L¹-1) to (L¹-54) and/or (L¹-92) to (L¹-108), especially preferably of the formula (L¹-1) to (L¹-29) and/or (L¹-92) to (L¹-103). Advantageously, the sum total of the indices k, l, g, h and j in the structures of the formulae (L¹-1) to (L¹-78) and/or (L¹-92) to (L¹-108), preferably of the formula (L¹-1) to (L¹-54) and/or (L¹-92) to (L¹-108), especially preferably of the formula (L¹-1) to (L¹-29) and/or (L¹-92) to (L¹-103), may in each case be not more than 3, preferably not more than 2 and more preferably not more than 1.

Preferred inventive compounds having a group of the formulae (Ar-1) to (Ar-11) and/or (Ar'-1) to (Ar'-11) comprise an $L^1$ group which is a bond or which is selected from one of the formulae (L¹-1) to (L¹-78) and/or (L¹-92) to (L¹-108), preferably of the formula (L¹-1) to (L¹-54) and/or (L¹-92) to (L¹-108), especially preferably of the formula (L¹-1) to (L¹-29) and/or (L¹-92) to (L¹-103). Advantageously, the sum total of the indices k, l, g, h and j in the structures of the formulae (L¹-1) to (L¹-78) and/or (L¹-92) to (L¹-108), preferably of the formula (L¹-1) to (L¹-54) and/or (L¹-92) to (L¹-108), especially preferably of the formula (L¹-1) to (L¹-29) and/or (L¹-92) to (L¹-103), may in each case be not more than 3, preferably not more than 2 and more preferably not more than 1.

Preferably, the $R^2$ radicals in the formulae (L¹-1) to (L¹-108) do not form a fused aromatic or heteroaromatic ring system, and preferably do not form any fused ring system, with the ring atoms of the aryl group or heteroaryl group to which the $R^2$ radicals are bonded. This includes the formation of a fused ring system with possible substituents $R^3$ which may be bonded to the $R^2$ radicals.

In a preferred configuration, compounds of the invention usable as active compound in an organic electronic device are selected from the group of the phenyls, fluorenes, indenofluorenes, spirobifluorenes, carbazoles, indenocarbazoles, indolocarbazoles, spirocarbazoles, pyrimidines, triazines, lactams, triarylamines, dibenzofurans, dibenzothienes, imidazoles, benzimidazoles, benzoxazoles, benzothiazoles, 5-arylphenanthridin-6-ones, 9,10-dehydrophenanthrenes, fluoranthenes, anthracenes, benzanthracenes, fluoradenes.

In a preferred configuration, inventive compounds are defined by the structures of the formulae (I), (II), (IIIa) to (IIIc), (IVa) to (IVc) and/or (V). Preferably, compounds usable as active compound in an organic electronic device, preferably compounds comprising structures of the formulae (I), (II), (IIIa) to (IIIc), (IVa) to (IVc) and/or (V), have a molecular weight of not more than 5000 g/mol, preferably not more than 4000 g/mol, particularly preferably not more than 3000 g/mol, especially preferably not more than 2000 g/mol and very particularly preferably not more than 1200 g/mol.

In addition, it is a feature of preferred compounds of the invention that they are sublimable. These compounds generally have a molar mass of less than about 1200 g/mol.

When the compound of the invention is substituted by aromatic or heteroaromatic $R^1$ or $R^2$ groups, it is preferable when these do not have any aryl or heteroaryl groups having more than two aromatic six-membered rings fused directly to one another. More preferably, the substituents do not have any aryl or heteroaryl groups having six-membered rings fused directly to one another at all. The reason for this preference is the low triplet energy of such structures. Fused aryl groups which have more than two aromatic six-membered rings fused directly to one another but are nevertheless also suitable in accordance with the invention are phenanthrene and triphenylene, since these also have a high triplet level.

In the case of configuration of the compounds of the invention that are usable as active compound in an organic electronic device for use as fluorescent emitters or as blue OLED materials, preferred compounds may contain corresponding groups, for example fluorene, anthracene and/or pyrene groups which may be substituted by $R^1$ or $R^2$ groups or which are formed by corresponding substitution of the (R¹-1) to (R¹-92) groups, preferably (R¹-33) to (R¹-57) and (R¹-76) to (R¹-86), or (L¹-1) to (L¹-109), preferably (L¹-30) to (L¹-60) and (L¹-71) to (L¹-91), by the substituents $R^2$.

In a further preferred embodiment of the invention, $R^2$, for example in a structure of formula (I) and preferred embodiments of this structure or the structures where reference is made to these formulae, is the same or different at each instance and is selected from the group consisting of H, D, an aliphatic hydrocarbyl radical having 1 to 10 carbon atoms, preferably having 1, 2, 3 or 4 carbon atoms, or an aromatic or heteroaromatic ring system which has 5 to 30 aromatic ring atoms, preferably 5 to 24 aromatic ring atoms, more preferably 5 to 13 aromatic ring atoms, and may be substituted by one or more alkyl groups each having 1 to 4 carbon atoms, but is preferably unsubstituted.

Preferably, the $R^2$ radicals do not form a fused aromatic or heteroaromatic ring system, and preferably do not form any fused ring system, with the ring atoms of the aryl group or heteroaryl group to which the $R^2$ radicals are bonded. This includes the formation of a fused ring system with possible substituents $R^3$ which may be bonded to the $R^2$ radicals.

In a further preferred embodiment of the invention, $R^3$, for example in a structure of formulae (I), (II), (IIIa), (IIIb), (IIIc), (IVa), (IVb), (IVc) and/or (V) and preferred embodiments of this structure or the structures where reference is made to these formulae, is the same or different at each instance and is selected from the group consisting of H, D, F, CN, an aliphatic hydrocarbyl radical having 1 to 10 carbon atoms, preferably having 1, 2, 3 or 4 carbon atoms, or an aromatic or heteroaromatic ring system which has 5 to 30 aromatic ring atoms, preferably 5 to 24 aromatic ring atoms, more preferably 5 to 13 aromatic ring atoms, and may be substituted by one or more alkyl groups each having 1 to 4 carbon atoms, but is preferably unsubstituted.

Particular preference is given to inventive compounds having structures of the formula (II) where the index m is an integer in the range from 0 to 4, preferably 0 to 2 and more preferably 0, and the index l is an integer in the range from 1 to 8, which have the following properties:

| R, not equal to H or D (if present) | preferably | at least one $R^a$ comprises one of the groups | preferably |
| --- | --- | --- | --- |
| $R^1$-1 to $R^1$-92 | $R^1$-1 to $R^1$-54 | H-1 to H-26 | H-4 to H-26 |
| $R^1$-1 to $R^1$-92 | $R^1$-1 to $R^1$-54 | H-1 to H-26 | H-1 |
| $R^1$-1 to $R^1$-92 | $R^1$-1 to $R^1$-54 | QL | Q-11 to Q-25, more preferably Q-16 to 19 and Q-23 to Q-25 |
| $R^1$-1 to $R^1$-92 | $R^1$-1 to $R^1$-54 | QL | Q-26 to Q44 |
| $R^1$-1 to $R^1$-92 | $R^1$-1 to $R^1$-54 | Ar-1 to Ar-11 | Ar-3 to Ar-5, preferably Ar-5 |
| $R^1$-1 to $R^1$-92 | $R^1$-1 to $R^1$-54 | Ar'-1 to Ar'-11 | Ar'-3 to Ar'-5, preferably Ar'-5 |
| $R^1$-1 to $R^1$-92 | $R^1$-1 to $R^1$-54 | $R^1$-1 to $R^1$-92 | $R^1$-5 to $R^1$-32 |
| $R^1$-1 to $R^1$-92 | $R^1$-1 to $R^1$-54 | $R^1$-1 to $R^1$-92 | $R^1$-33 to $R^1$-54 |
| $R^1$-1 to $R^1$-4 | $R^1$-1 | H4 - H-26 | H-4, H-5 |
| $R^1$-1 to $R^1$-4 | $R^1$-1 | H-1 | H-1 |
| $R^1$-1 to $R^1$-4 | $R^1$-1 | Q-11 to Q-25 | Q-16 to 19 and Q-23 to Q-25 |
| $R^1$-1 to $R^1$-4 | $R^1$-1 | Q-16 to 19 and Q-23 to Q-25 | Q-23 |
| $R^1$-1 to $R^1$-4 | $R^1$-1 | Ar-1 to Ar-11 | Ar-3 to Ar-5, preferably Ar-5 |
| $R^1$-1 to $R^1$-4 | $R^1$-1 | Ar'-1 to Ar'-11 | Ar'-3 to Ar'-5, preferably Ar'-5 |
| $R^1$-1 to $R^1$-4 | $R^1$-1 | $R^1$-1 to $R^1$-92 | $R^1$-5 to $R^1$-32 |
| $R^1$-1 to $R^1$-4 | $R^1$-1 | $R^1$-33 to $R^1$-54 | $R^1$-41 to $R^1$-54 |

Particular preference is further given to inventive compounds having structures of the formulae (IIIa), (IIIb) and (IIIc) where the index n is an integer in the range from 0 to 4, preferably 0 to 2 and more preferably 0, which have the following properties:

| R, not equal to H or D (if present) | preferably | at least one $R^a$ comprises one of the groups | preferably |
| --- | --- | --- | --- |
| $R^1$-1 to $R^1$-92 | $R^1$-1 to $R^1$-54 | H-1 to H-26 | H-4 to H-26 |
| $R^1$-1 to $R^1$-92 | $R^1$-1 to $R^1$-54 | H-1 to H-26 | H-1 |
| $R^1$-1 to $R^1$-92 | $R^1$-1 to $R^1$-54 | QL | Q-11 to Q-25, more preferably Q-16 to 19 and Q-23 to Q-25 |
| $R^1$-1 to $R^1$-92 | $R^1$-1 to $R^1$-54 | QL | Q-26 to Q44 |
| $R^1$-1 to $R^1$-92 | $R^1$-1 to $R^1$-54 | Ar-1 to Ar-11 | Ar-3 to Ar-5, preferably Ar-5 |
| $R^1$-1 to $R^1$-92 | $R^1$-1 to $R^1$-54 | Ar'-1 to Ar'-11 | Ar'-3 to Ar'-5, preferably Ar'-5 |
| $R^1$-1 to $R^1$-92 | $R^1$-1 to $R^1$-54 | $R^1$-1 to $R^1$-92 | $R^1$-5 to $R^1$-32 |
| $R^1$-1 to $R^1$-92 | $R^1$-1 to $R^1$-54 | $R^1$-1 to $R^1$-92 | $R^1$-33 to $R^1$-54 |
| $R^1$-1 to $R^1$-4 | $R^1$-1 | H4 - H-26 | H4, H-5 |
| $R^1$-1 to $R^1$-4 | $R^1$-1 | H-1 | H1 |
| $R^1$-1 to $R^1$-4 | $R^1$-1 | Q-11 to Q-25 | Q-16 to 19 and Q-23 to Q-25 |
| $R^1$-1 to $R^1$-4 | $R^1$-1 | Q-16 to 19 and Q-23 to Q-25 | Q-23 |
| $R^1$-1 to $R^1$-4 | $R^1$-1 | Ar-1 to Ar-11 | Ar-3 to Ar-5, preferably Ar-5 |
| $R^1$-1 to $R^1$-4 | $R^1$-1 | Ar'-1 to Ar'-11 | Ar'-3 to Ar'-5, preferably Ar'-5 |
| $R^1$-1 to $R^1$-4 | $R^1$-1 | $R^1$-1 to $R^1$-92 | $R^1$-5 to $R^1$-32 |
| $R^1$-1 to $R^1$-4 | $R^1$-1 | $R^1$-33 to $R^1$-54 | $R^1$-41 to $R^1$-54 |

In a particularly preferred embodiment, both $R^a$ radicals are the same. Preference is given here to structures of the formulae (IIIa) and (IIIb), particular preference to structures of the formula (IIIb).

Particular preference is further given to inventive compounds having structures of the formulae (IVa), (IVb) and (IVc) where the index n is an integer in the range from 0 to 4, preferably 0 to 2 and more preferably 0, which have the following properties:

| R, not equal to H or D (if present) | preferably | at least one $R^a$ comprises one of the groups | preferably |
| --- | --- | --- | --- |
| $R^1$-1 to $R^1$-92 | $R^1$-1 to $R^1$-54 | H-1 to H-26 | H-4 to H-26 |
| $R^1$-1 to $R^1$-92 | $R^1$-1 to $R^1$-54 | H-1 to H-26 | H-1 |
| $R^1$-1 to $R^1$-92 | $R^1$-1 to $R^1$-54 | QL | Q-11 to Q-25, more preferably Q-16 to 19 and Q-23 to Q-25 |
| $R^1$-1 to $R^1$-92 | $R^1$-1 to $R^1$-54 | QL | Q-26 to Q44 |
| $R^1$-1 to $R^1$-92 | $R^1$-1 to $R^1$-54 | Ar-1 to Ar-11 | Ar-3 to Ar-5, preferably Ar-5 |
| $R^1$-1 to $R^1$-92 | $R^1$-1 to $R^1$-54 | Ar'-1 to Ar'-11 | Ar'-3 to Ar'-5, preferably Ar'-5 |
| $R^1$-1 to $R^1$-92 | $R^1$-1 to $R^1$-54 | $R^1$-1 to $R^1$-92 | $R^1$-5 to $R^1$-32 |
| $R^1$-1 to $R^1$-92 | $R^1$-1 to $R^1$-54 | $R^1$-1 to $R^1$-92 | $R^1$-33 to $R^1$-54 |
| $R^1$-1 to $R^1$-4 | $R^1$-1 | H4 - H-26 | H4, H-5 |
| $R^1$-1 to $R^1$-4 | $R^1$-1 | H-1 | H1 |
| $R^1$-1 to $R^1$-4 | $R^1$-1 | Q-11 to Q-25 | Q-16 to 19 and Q-23 to Q-25 |
| $R^1$-1 to $R^1$-4 | $R^1$-1 | Q-16 to 19 and Q-23 to Q-25 | Q-23 |
| $R^1$-1 to $R^1$-4 | $R^1$-1 | Ar-1 to Ar-11 | Ar-3 to Ar-5, preferably Ar-5 |
| $R^1$-1 to $R^1$-4 | $R^1$-1 | Ar'-1 to Ar'-11 | Ar'-3 to Ar'-5, preferably Ar'-5 |
| $R^1$-1 to $R^1$-4 | $R^1$-1 | $R^1$-1 to $R^1$-92 | $R^1$-5 to $R^1$-32 |
| $R^1$-1 to $R^1$-4 | $R^1$-1 | $R^1$-33 to $R^1$-54 | $R^1$-41 to $R^1$-54 |

In a particularly preferred embodiment, all four $R^a$ radicals are the same. Preference is given here to structures of the formulae (IVa) and (IVb), particular preference to structures of the formula (IVa).

Particular preference is further given to inventive compounds having structures of the formula (V) that have the following properties:

| at least four $R^a$ radicals comprise one of the groups | preferably | more preferably | most preferably |
|---|---|---|---|
| H-1 to H-26 | H-1 - H-11 and H-15 to H-17 | H-1 to H-11 | H-1 |
| H-1 to H-26 | H-4 to H-26 | H-4 to H-19 and H-15 to H-17 | H4, H-5 |
| QL | Q-11 to Q-25, | Q-16 to 19 and Q-23 to Q-25 | Q-23 |
| QL | Q-26 to Q44 | Q-33 to Q-42 | Q-33 and Q34 |
| Ar-1 to Ar-11 | Ar-3 to Ar-11 | Ar-3 to Ar-5 | Ar-5 |
| Ar'-1 to Ar'-11 | Ar'-3 to Ar'-11 | Ar'-3 to Ar'-5 | Ar'-5 |
| $R^1$-1 to $R^1$-92 | $R^1$-5 to $R^1$-54 | $R^1$-5 to $R^1$-32 | |
| $R^1$-1 to $R^1$-92 | $R^1$-5 to $R^1$-54 | $R^1$-33 to $R^1$-54 | |
| Ar-1 to Ar-11 | Ar-3 to Ar-11 | Ar-3 to Ar-5 | Ar-5 |
| Ar'-1 to Ar'-11 | Ar'-3 to Ar'-11 | Ar'-3 to Ar'-5 | Ar'-5 |
| $R^1$-1 to $R^1$-92 | $R^1$-5 to $R^1$-32 | $R^1$-5 to $R^1$-15 | $R^1$-9 and $R^1$-11 |
| $R^1$-1 to $R^1$-92 | $R^1$-41 to $R^1$-54 | $R^1$-33 to $R^1$-54 | |

In a particularly preferred embodiment, all R radicals are the same.

Particular preference is given to inventive compounds having structures of the formula (II) where the index m is an integer in the range from 0 to 4, preferably 0 to 2 and more preferably 0, and the index l is an integer in the range from 1 to 8, which have the following properties:

| at least one $R^a$ comprises one of the groups | where $Ar^3$, $Ar^4$ | $Ar^2$ | $R^1$ (if present) |
|---|---|---|---|
| H-1 to H-3 | $R^1$-1 to $R^1$-92 | $L^1$-1 to $L^1$-108 | $R^1$-1 to $R^1$-92 |
| H-1 to H-3 | $R^1$-1 to $R^1$-92 | bond | $R^1$-1 to $R^1$-92 |
| H-1 to H-3 | $R^1$-1 to $R^1$-92 | $L^1$-1 to $L^1$-4 | $R^1$-1 to $R^1$-92 |
| H-1 | $R^1$-2 to $R^1$-32 | bond, $L^1$-1 to $L^1$-4 | $R^1$-1 to $R^1$-92 |
| H-1 | $R^1$-2 to $R^1$-32 | $L^1$-41 to $L^1$-54 | $R^1$-1 to $R^1$-92 |
| H-1 | $R^1$-1 | bond, $L^1$-1 to $L^1$-4 | $R^1$-1 to $R^1$-92 |
| H-1 | $R^1$-1 | $L^1$-41 to $L^1$-54 | $R^1$-1 to $R^1$-92 |
| H-2 | $R^1$-2 to $R^1$-32 | bond, $L^1$-1 to $L^1$-4 | $R^1$-1 to $R^1$-92 |
| H-2 | $R^1$-2 to $R^1$-32 | $L^1$-41 to $L^1$-54 | $R^1$-1 to $R^1$-92 |
| H-2 | $R^1$-1 | bond, $L^1$-1 to $L^1$-4 | $R^1$-1 to $R^1$-92 |
| H-2 | $R^1$-1 | $L^1$-41 to $L^1$-54 | $R^1$-1 to $R^1$-92 |
| H-3 | $R^1$-2 to $R^1$-32 | bond, $L^1$-1 to $L^1$-4 | $R^1$-1 to $R^1$-92 |
| H-3 | $R^1$-2 to $R^1$-32 | $L^1$-41 to $L^1$-54 | $R^1$-1 to $R^1$-92 |
| H-3 | $R^1$-1 | bond, $L^1$-1 to $L^1$-4 | $R^1$-1 to $R^1$-92 |
| H-3 | $R^1$-1 | $L^1$-41 to $L^1$-54 | $R^1$-1 to $R^1$-92 |

Particular preference is given to inventive compounds having structures of the formula (II) where the index m is an integer in the range from 0 to 4, preferably 0 to 2 and more preferably 0, and the index l is an integer in the range from 1 to 8, which have the following properties:

| at least one $R^a$ comprises one of the groups | $Ar^2$ | $Ar^2$ (preferred) | $Ar^1$ or $R^1$ (if present) |
|---|---|---|---|
| H-4 to H-26 | $L^1$-1 to $L^1$-108 | $L^1$-1 to $L^1$-54, $L^1$-92 to $L^1$-108 | $R^1$-1 to $R^1$-92 |
| H-4 to H-26 | bond or $L^1$-1 to $L^1$-54, $L^1$-92 to $L^1$-108 | bond | $R^1$-1 to $R^1$-92 |
| H-4 to H-26 | bond or $L^1$-1 to $L^1$-4, $L^1$-92 to $L^1$-103 | $L^1$-1 to $L^1$-4 | $R^1$-1 to $R^1$-92 |
| H-4 to H-26 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-4 | $L^1$-1 to $L^1$-108 | $L^1$-1 to $L^1$-54, $L^1$-92 to $L^1$-108 | $R^1$-1 to $R^1$-92 |
| H-4 | bond or $L^1$-1 to $L^1$-54, $L^1$-92 to $L^1$-108 | bond | $R^1$-1 to $R^1$-92 |
| H-4 | bond or $L^1$-1 to $L^1$-4, $L^1$-92 to $L^1$-103 | $L^1$-1 to $L^1$-4 | $R^1$-1 to $R^1$-92 |
| H-4 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-5 | $L^1$-1 to $L^1$-108 | $L^1$-1 to $L^1$-54, $L^1$-92 to $L^1$-108 | $R^1$-1 to $R^1$-92 |
| H-5 | bond or $L^1$-1 to $L^1$-54, $L^1$-92 to $L^1$-108 | bond | $R^1$-1 to $R^1$-92 |
| H-5 | bond or $L^1$-1 to $L^1$-4, $L^1$-92 to $L^1$-103 | $L^1$-1 to $L^1$-4 | $R^1$-1 to $R^1$-92 |
| H-5 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-6 | $L^1$-1 to $L^1$-108 | $L^1$-1 to $L^1$-54, $L^1$-92 to $L^1$-108 | $R^1$-1 to $R^1$-92 |
| H-6 | bond or $L^1$-1 to $L^1$-54, $L^1$-92 to $L^1$-108 | bond | $R^1$-1 to $R^1$-92 |
| H-6 | bond or $L^1$-1 to $L^1$-4, $L^1$-92 to $L^1$-103 | $L^1$-1 to $L^1$-4 | $R^1$-1 to $R^1$-92 |
| H-6 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-7 | $L^1$-1 to $L^1$-108 | $L^1$-1 to $L^1$-54, $L^1$-92 to $L^1$-108 | $R^1$-1 to $R^1$-92 |
| H-7 | bond or $L^1$-1 to $L^1$-54, $L^1$-92 to $L^1$-108 | bond | $R^1$-1 to $R^1$-92 |
| H-7 | bond or $L^1$-1 to $L^1$-4, $L^1$-92 to $L^1$-103 | $L^1$-1 to $L^1$-4 | $R^1$-1 to $R^1$-92 |
| H-7 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-8 | $L^1$-1 to $L^1$-108 | $L^1$-1 to $L^1$-54, $L^1$-92 to $L^1$-108 | $R^1$-1 to $R^1$-92 |
| H-8 | bond or $L^1$-1 to $L^1$-54, $L^1$-92 to $L^1$-108 | bond | $R^1$-1 to $R^1$-92 |
| H-8 | bond or $L^1$-1 to $L^1$-4, $L^1$-92 to $L^1$-103 | $L^1$-1 to $L^1$-4 | $R^1$-1 to $R^1$-92 |
| H-8 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |

Particular preference is given to inventive compounds having structures of the formula (II) where the index m is an integer in the range from 0 to 4, preferably 0 to 2 and more preferably 0, and the index l is an integer in the range from 1 to 8, which have the following properties:

| at least one Rᵃ comprises one of the groups | L¹ | L¹ (preferred) | Ar¹ or R¹ (if present) |
|---|---|---|---|
| Q-1 to Q-44 | L¹-1 to L¹-108 | L¹-1 to L¹-54, L¹-92 to L¹-108 | R¹-1 to R¹-92 |
| Q-1 to Q-44 | bond or L¹-1 to L¹-54, L¹-92 to L¹-108 | bond | R¹-1 to R¹-92 |
| Q-1 to Q-44 | bond or L¹-1 to L¹-4, L¹-92 to L¹-103 | L¹-1 to L¹-4 | R¹-1 to R¹-92 |
| Q-1 to Q-44 | L¹-30 to L¹-52 or L¹-104 to L¹-108 | L¹-37 to L¹-52 or L¹-106 to L¹-108 | R¹-1 to R¹-92 |
| Q-11 to Q-25 | L¹-1 to L¹-108 | L¹-1 to L¹-54, L¹-92 to L¹-108 | R¹-1 to R¹-92 |
| Q-11 to Q-25 | bond or L¹-1 to L¹-54, L¹-92 to L¹-108 | bond | R¹-1 to R¹-92 |
| Q-11 to Q-25 | bond or L¹-1 to L¹-4, L¹-92 to L¹-103 | L¹-1 to L¹-4 | R¹-1 to R¹-92 |
| Q-11 to Q-25 | L¹-30 to L¹-52 or L¹-104 to L¹-108 | L¹-37 to L¹-52 or L¹-106 to L¹-108 | R¹-1 to R¹-92 |
| Q-26 to Q-44, preferably Q-26 to Q-42 | L¹-1 to L¹-108 | L¹-1 to L¹-54, L¹-92 to L¹-108 | R¹-1 to R¹-92 |
| Q-26 to Q-44, preferably Q-26 to Q-42 | bond or L¹-1 to L¹-54, L¹-92 to L¹-108 | bond | R¹-1 to R¹-92 |
| Q-26 to Q-44, preferably Q-26 to Q-42 | bond or L¹-1 to L¹-4, L¹-92 to L¹-103 | L¹-1 to L¹-4 | R¹-1 to R¹-92 |
| Q-26 to Q-44, preferably Q-26 to Q-42 | L¹-30 to L¹-52 or L¹-104 to L¹-108 | L¹-37 to L¹-52 or L¹-106 to L¹-108 | R¹-1 to R¹-92 |
| Q-23 to Q-25 | L¹-1 to L¹-108 | L¹-1 to L¹-54, L¹-92 to L¹-108 | R¹-1 to R¹-92 |
| Q-23 to Q-25 | bond or L¹-1 to L¹-54, L¹-92 to L¹-108 | bond | R¹-1 to R¹-92 |
| Q-23 to Q-25 | bond or L¹-1 to L¹-4, L¹-92 to L¹-103 | L¹-1 to L¹-4 | R¹-1 to R¹-92 |
| Q-23 to Q-25 | L¹-30 to L¹-52 or L¹-104 to L¹-108 | L¹-37 to L¹-52 or L¹-106 to L¹-108 | R¹-1 to R¹-92 |
| Q-23 | L¹-1 to L¹-108 | L¹-1 to L¹-54, L¹-92 to L¹-108 | R¹-1 to R¹-92 |
| Q-23 | bond or L¹-1 to L¹-54, L¹-92 to L¹-108 | bond | R¹-1 to R¹-92 |
| Q-23 | bond or L¹-1 to L¹-4, L¹-92 to L¹-103 | L¹-1 to L¹-4 | R¹-1 to R¹-92 |
| Q-23 | L¹-30 to L¹-52 or L¹-104 to L¹-108 | L¹-37 to L¹-52 or L¹-106 to L¹-108 | R¹-1 to R¹-92 |

Particular preference is given to inventive compounds having structures of the formula (II) where the index m is an integer in the range from 0 to 4, preferably 0 to 2 and more preferably 0, and the index l is an integer in the range from 1 to 8, which have the following properties:

| at least one Rᵃ comprises one of the groups | L¹ | L¹ (preferred) | Ar¹ or R¹ (if present) |
|---|---|---|---|
| Ar-1 to Ar-11 | L¹-1 to L¹-108 | L¹-1 to L¹-54, L¹-92 to L¹-108 | R¹-1 to R¹-92 |
| Ar-1 to Ar-11 | bond or L¹-1 to L¹-54, L¹-92 to L¹-108 | bond | R¹-1 to R¹-92 |
| Ar-1 to Ar-11 | bond or L¹-1 to L¹-4, L¹-92 to L¹-103 | L¹-1 to L¹-4 | R¹-1 to R¹-92 |
| Ar-1 to Ar-11 | L¹-30 to L¹-52 or L¹-104 to L¹-108 | L¹-37 to L¹-52 or L¹-106 to L¹-108 | R¹-1 to R¹-92 |
| Ar-3 to Ar-11 | L¹-1 to L¹-108 | L¹-1 to L¹-54, L¹-92 to L¹-108 | R¹-1 to R¹-92 |
| Ar-3 to Ar-11 | bond or L¹-1 to L¹-54, L¹-92 to L¹-108 | bond | R¹-1 to R¹-92 |
| Ar-3 to Ar-11 | bond or L¹-1 to L¹-4, L¹-92 to L¹-103 | L¹-1 to L¹-4 | R¹-1 to R¹-92 |
| Ar-3 to Ar-11 | L¹-30 to L¹-52 or L¹-104 to L¹-108 | L¹-37 to L¹-52 or L¹-106 to L¹-108 | R¹-1 to R¹-92 |
| Ar-3 to Ar-5 | L¹-1 to L¹-108 | L¹-1 to L¹-54, L¹-92 to L¹-108 | R¹-1 to R¹-92 |
| Ar-3 to Ar-5 | bond or L¹-1 to L¹-54, L¹-92 to L¹-108 | bond | R¹-1 to R¹-92 |
| Ar-3 to Ar-5 | bond or L¹-1 to L¹-4, L¹-92 to L¹-103 | L¹-1 to L¹-4 | R¹-1 to R¹-92 |
| Ar-3 to Ar-5 | L¹-30 to L¹-52 or L¹-104 to L¹-108 | L¹-37 to L¹-52 or L¹-106 to L¹-108 | R¹-1 to R¹-92 |
| Ar-5 | L¹-1 to L¹-108 | L¹-1 to L¹-54, L¹-92 to L¹-108 | R¹-1 to R¹-92 |
| Ar-5 | bond or L¹-1 to L¹-54, L¹-92 to L¹-108 | bond | R¹-1 to R¹-92 |
| Ar-5 | bond or L¹-1 to L¹-4, L¹-92 to L¹-103 | L¹-1 to L¹-4 | R¹-1 to R¹-92 |
| Ar-5 | L¹-30 to L¹-52 or L¹-104 to L¹-108 | L¹-37 to L¹-52 or L¹-106 to L¹-108 | R¹-1 to R¹-92 |
| Ar'-1 to Ar'-11 | L¹-1 to L¹-108 | L¹-1 to L¹-54, L¹-92 to L¹-108 | R¹-1 to R¹-92 |
| Ar'-1 to Ar'-11 | bond or L¹-1 to L¹-54, L¹-92 to L¹-108 | bond | R¹-1 to R¹-92 |
| Ar'-1 to Ar'-11 | bond or L¹-1 to L¹-4, L¹-92 to L¹-103 | L¹-1 to L¹-4 | R¹-1 to R¹-92 |
| Ar'-1 to Ar'-11 | L¹-30 to L¹-52 or L¹-104 to L¹-108 | L¹-37 to L¹-52 or L¹-106 to L¹-108 | R¹-1 to R¹-92 |
| Ar'-3 to Ar'-11 | L¹-1 to L¹-108 | L¹-1 to L¹-54, L¹-92 to L¹-108 | R¹-1 to R¹-92 |
| Ar'-3 to Ar'-11 | bond or L¹-1 to L¹-54, L¹-92 to L¹-108 | bond | R¹-1 to R¹-92 |
| Ar'-3 to Ar'-11 | bond or L¹-1 to L¹-4, L¹-92 to L¹-103 | L¹-1 to L¹-4 | R¹-1 to R¹-92 |
| Ar'-3 to Ar'-11 | L¹-30 to L¹-52 or L¹-104 to L¹-108 | L¹-37 to L¹-52 or L¹-106 to L¹-108 | R¹-1 to R¹-92 |
| Ar'-3 to Ar'-5 | L¹-1 to L¹-108 | L¹-1 to L¹-54, L¹-92 to L¹-108 | R¹-1 to R¹-92 |
| Ar'-3 to Ar'-5 | bond or L¹-1 to L¹-54, L¹-92 to L¹-108 | bond | R¹-1 to R¹-92 |
| Ar'-3 to Ar'-5 | bond or L¹-1 to L¹-4, L¹-92 to L¹-103 | L¹-1 to L¹-4 | R¹-1 to R¹-92 |
| Ar'-3 to Ar'-5 | L¹-30 to L¹-52 or L¹-104 to L¹-108 | L¹-37 to L¹-52 or L¹-106 to L¹-108 | R¹-1 to R¹-92 |
| Ar'-5 | L¹-1 to L¹-108 | L¹-1 to L¹-54, L¹-92 to L¹-108 | R¹-1 to R¹-92 |
| Ar'-5 | bond or L¹-1 to L¹-54, L¹-92 to L¹-108 | bond | R¹-1 to R¹-92 |
| Ar'-5 | bond or L¹-1 to L¹-4, L¹-92 to L¹-103 | L¹-1 to L¹-4 | R¹-1 to R¹-92 |

Particular preference is further given to inventive compounds having structures of the formulae (IIIa), (IIIb) and (IIIc) where the index n is an integer in the range from 0 to 4, preferably 0 to 2 and more preferably 0, which have the following properties:

| at least one $R^a$ comprises one of the groups | $L^1$ | $L^1$ (preferred) | $Ar^1$ or $R^1$ (if present) |
|---|---|---|---|
| Ar'-5 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |

Particular preference is further given to inventive compounds having structures of the formulae (IIIa), (IIIb) and (IIIc) where the index n is an integer in the range from 0 to 4, preferably 0 to 2 and more preferably 0, which have the following properties:

| at least one $R^a$ comprises one of the groups | where $Ar^3$, $Ar^4$ | $Ar^2$ | $R^1$ (if present) |
|---|---|---|---|
| H-1 to H-3 | $R^1$-1 to $R^1$-92 | $L^1$-1 to $L^1$-108 | $R^1$-1 to $R^1$-92 |
| H-1 to H-3 | $R^1$-1 to $R^1$-92 | bond | $R^1$-1 to $R^1$-92 |
| H-1 to H-3 | $R^1$-1 to $R^1$-92 | $L^1$-1 to $L^1$-4 | $R^1$-1 to $R^1$-92 |
| H-1 | $R^1$-2 to $R^1$-32 | bond, $L^1$-1 to $L^1$-4 | $R^1$-1 to $R^1$-92 |
| H-1 | $R^1$-2 to $R^1$-32 | $L^1$-41 to $L^1$-54 | $R^1$-1 to $R^1$-92 |
| H-1 | $R^1$-1 | bond, $L^1$-1 to $L^1$-4 | $R^1$-1 to $R^1$-92 |
| H-1 | $R^1$-1 | $L^1$-41 to $L^1$-54 | $R^1$-1 to $R^1$-92 |
| H-2 | $R^1$-2 to $R^1$-32 | bond, $L^1$-1 to $L^1$-4 | $R^1$-1 to $R^1$-92 |
| H-2 | $R^1$-2 to $R^1$-32 | $L^1$-41 to $L^1$-54 | $R^1$-1 to $R^1$-92 |
| H-2 | $R^1$-1 | bond, $L^1$-1 to $L^1$-4 | $R^1$-1 to $R^1$-92 |
| H-2 | $R^1$-1 | $L^1$-41 to $L^1$-54 | $R^1$-1 to $R^1$-92 |
| H-3 | $R^1$-2 to $R^1$-32 | bond, $L^1$-1 to $L^1$-4 | $R^1$-1 to $R^1$-92 |
| H-3 | $R^1$-2 to $R^1$-32 | $L^1$-41 to $L^1$-54 | $R^1$-1 to $R^1$-92 |
| H-3 | $R^1$-1 | bond, $L^1$-1 to $L^1$-4 | $R^1$-1 to $R^1$-92 |
| H-3 | $R^1$-1 | $L^1$-41 to $L^1$-54 | $R^1$-1 to $R^1$-92 |

In a particularly preferred embodiment, both $R^a$ radicals are the same. Preference is given here to structures of the formulae (IIIa) and (IIIb), particular preference to structures of the formula (IIIb).

Particular preference is further given to inventive compounds having structures of the formulae (IIIa), (IIIb) and (IIIc) where the index n is an integer in the range from 0 to 4, preferably 0 to 2 and more preferably 0, which have the following properties:

| at least one $R^a$ comprises one of the groups | $Ar^2$ | $Ar^2$ (preferred) | $Ar^1$ or $R^1$ (if present) |
|---|---|---|---|
| H-4 to H-26 | $L^1$-1 to $L^1$-108 | $L^1$-1 to $L^1$-54, $L^1$-92 to $L^1$-108 | $R^1$-1 to $R^1$-92 |
| H-4 to H-26 | bond or $L^1$-1 to $L^1$-54, $L^1$-92 to $L^1$-108 | bond | $R^1$-1 to $R^1$-92 |
| H-4 to H-26 | bond or $L^1$-1 to $L^1$-4, $L^1$-92 to $L^1$-103 | $L^1$-1 to $L^1$-4 | $R^1$-1 to $R^1$-92 |
| H-4 to H-26 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-4 | $L^1$-1 to $L^1$-108 | $L^1$-1 to $L^1$-54, $L^1$-92 to $L^1$-108 | $R^1$-1 to $R^1$-92 |
| H-4 | bond or $L^1$-1 to $L^1$-54, $L^1$-92 to $L^1$-108 | bond | $R^1$-1 to $R^1$-92 |
| H-4 | bond or $L^1$-1 to $L^1$-4, $L^1$-92 to $L^1$-103 | $L^1$-1 to $L^1$-4 | $R^1$-1 to $R^1$-92 |
| H-4 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-5 | $L^1$-1 to $L^1$-108 | $L^1$-1 to $L^1$-54, $L^1$-92 to $L^1$-108 | $R^1$-1 to $R^1$-92 |
| H-5 | bond or $L^1$-1 to $L^1$-54, $L^1$-92 to $L^1$-108 | bond | $R^1$-1 to $R^1$-92 |
| H-5 | bond or $L^1$-1 to $L^1$-4, $L^1$-92 to $L^1$-103 | $L^1$-1 to $L^1$-4 | $R^1$-1 to $R^1$-92 |
| H-5 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-6 | $L^1$-1 to $L^1$-108 | $L^1$-1 to $L^1$-54, $L^1$-92 to $L^1$-108 | $R^1$-1 to $R^1$-92 |
| H-6 | bond or $L^1$-1 to $L^1$-54, $L^1$-92 to $L^1$-108 | bond | $R^1$-1 to $R^1$-92 |
| H-6 | bond or $L^1$-1 to $L^1$-4, $L^1$-92 to $L^1$-103 | $L^1$-1 to $L^1$-4 | $R^1$-1 to $R^1$-92 |
| H-6 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-7 | $L^1$-1 to $L^1$-108 | $L^1$-1 to $L^1$-54, $L^1$-92 to $L^1$-108 | $R^1$-1 to $R^1$-92 |
| H-7 | bond or $L^1$-1 to $L^1$-54, $L^1$-92 to $L^1$-108 | bond | $R^1$-1 to $R^1$-92 |
| H-7 | bond or $L^1$-1 to $L^1$-4, $L^1$-92 to $L^1$-103 | $L^1$-1 to $L^1$-4 | $R^1$-1 to $R^1$-92 |
| H-7 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-8 | $L^1$-1 to $L^1$-108 | $L^1$-1 to $L^1$-54, $L^1$-92 to $L^1$-108 | $R^1$-1 to $R^1$-92 |
| H-8 | bond or $L^1$-1 to $L^1$-54, $L^1$-92 to $L^1$-108 | bond | $R^1$-1 to $R^1$-92 |
| H-8 | bond or $L^1$-1 to $L^1$-4, $L^1$-92 to $L^1$-103 | $L^1$-1 to $L^1$-4 | $R^1$-1 to $R^1$-92 |
| H-8 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |

In a particularly preferred embodiment, both R radicals are the same. Preference is given here to structures of the formulae (IIIa) and (IIIb), particular preference to structures of the formula (IIIb).

Particular preference is further given to inventive compounds having structures of the formulae (IIIa), (IIIb) and (IIIc) where the index n is an integer in the range from 0 to 4, preferably 0 to 2 and more preferably 0, which have the following properties:

| at least one $R^a$ comprises one of the groups | $L^1$ | $L^1$ (preferred) | $Ar^1$ or $R^1$ (if present) |
|---|---|---|---|
| Q-1 to Q-44 | $L^1$-1 to $L^1$-108 | $L^1$-1 to $L^1$-54, $L^1$-92 to $L^1$-108 | $R^1$-1 to $R^1$-92 |
| Q-1 to Q-44 | bond or $L^1$-1 to $L^1$-54, $L^1$-92 to $L^1$-108 | bond | $R^1$-1 to $R^1$-92 |

| at least one $R^a$ comprises one of the groups | $L^1$ | $L^1$ (preferred) | $Ar^1$ or $R^1$ (if present) |
|---|---|---|---|
| Q-1 to Q-44 | bond or $L^1$-1 to $L^1$-4, $L^1$-92 to $L^1$-103 | $L^1$-1 to $L^1$-4 | $R^1$-1 to $R^1$-92 |
| Q-1 to Q-44 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Q-11 to Q-25 | $L^1$-1 to $L^1$-108 | $L^1$-1 to $L^1$-54, $L^1$-92 to $L^1$-108 | $R^1$-1 to $R^1$-92 |
| Q-11 to Q-25 | bond or $L^1$-1 to $L^1$-54, $L^1$-92 to $L^1$-108 | bond | $R^1$-1 to $R^1$-92 |
| Q-11 to Q-25 | bond or $L^1$-1 to $L^1$-4, $L^1$-92 to $L^1$-103 | $L^1$-1 to $L^1$-4 | $R^1$-1 to $R^1$-92 |
| Q-11 to Q-25 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Q-26 to Q-44, preferably Q-26 to Q-42 | $L^1$-1 to $L^1$-108 | $L^1$-1 to $L^1$-54, $L^1$-92 to $L^1$-108 | $R^1$-1 to $R^1$-92 |
| Q-26 to Q-44, preferably Q-26 to Q-42 | bond or $L^1$-1 to $L^1$-54, $L^1$-92 to $L^1$-108 | bond | $R^1$-1 to $R^1$-92 |
| Q-26 to Q-44, preferably Q-26 to Q-42 | bond or $L^1$-1 to $L^1$-4, $L^1$-92 to $L^1$-103 | $L^1$-1 to $L^1$-4 | $R^1$-1 to $R^1$-92 |
| Q-26 to Q-44, preferably Q-26 to Q-42 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Q-23 to Q-25 | $L^1$-1 to $L^1$-108 | $L^1$-1 to $L^1$-54, $L^1$-92 to $L^1$-108 | $R^1$-1 to $R^1$-92 |
| Q-23 to Q-25 | bond or $L^1$-1 to $L^1$-54, $L^1$-92 to $L^1$-108 | bond | $R^1$-1 to $R^1$-92 |
| Q-23 to Q-25 $L^1$-4, $L^1$-92 to $L^1$-103 | bond or $L^1$-1 to | $L^1$-1 to $L^1$-4 | $R^1$-1 to $R^1$-92 |
| Q-23 to Q-25 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Q-23 | $L^1$-1 to $L^1$-108 | $L^1$-1 to $L^1$-54, $L^1$-92 to $L^1$-108 | $R^1$-1 to $R^1$-92 |
| Q-23 | bond or $L^1$-1 to $L^1$-54, $L^1$-92 to $L^1$-108 | bond | $R^1$-1 to $R^1$-92 |
| Q-23 | bond or $L^1$-1 to $L^1$-4, $L^1$-92 to $L^1$-103 | $L^1$-1 to $L^1$-4 | $R^1$-1 to $R^1$-92 |
| Q-23 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |

In a particularly preferred embodiment, both R radicals are the same. Preference is given here to structures of the formulae (IIIa) and (IIIb), particular preference to structures of the formula (IIIb).

Particular preference is further given to inventive compounds having structures of the formulae (IIIa), (IIIb) and (IIIc) where the index n is an integer in the range from 0 to 4, preferably 0 to 2 and more preferably 0, which have the following properties:

| at least one $R^a$ comprises one of the groups | $L^1$ | $L^1$ (preferred) | $Ar^1$ or $R^1$ (if present) |
|---|---|---|---|
| Ar-1 to Ar-11 | $L^1$-1 to $L^1$-108 | $L^1$-1 to $L^1$-54, $L^1$-92 to $L^1$-108 | $R^1$-1 to $R^1$-92 |
| Ar-1 to Ar-11 | bond or $L^1$-1 to $L^1$-54, $L^1$-92 to $L^1$-108 | bond | $R^1$-1 to $R^1$-92 |
| Ar-1 to Ar-11 | bond or $L^1$-1 to $L^1$-4, $L^1$-92 to $L^1$-103 | $L^1$-1 to $L^1$-4 | $R^1$-1 to $R^1$-92 |
| Ar-1 to Ar-11 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Ar-3 to Ar-11 | $L^1$-1 to $L^1$-108 | $L^1$-1 to $L^1$-54, $L^1$-92 to $L^1$-108 | $R^1$-1 to $R^1$-92 |
| Ar-3 to Ar-11 | bond or $L^1$-1 to $L^1$-54, $L^1$-92 to $L^1$-108 | bond | $R^1$-1 to $R^1$-92 |
| Ar-3 to Ar-11 | bond or $L^1$-1 to $L^1$-4, $L^1$-92 to $L^1$-103 | $L^1$-1 to $L^1$-4 | $R^1$-1 to $R^1$-92 |
| Ar-3 to Ar-11 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Ar-3 to Ar-5 | $L^1$-1 to $L^1$-108 | $L^1$-1 to $L^1$-54, $L^1$-92 to $L^1$-108 | $R^1$-1 to $R^1$-92 |
| Ar-3 to Ar-5 | bond or $L^1$-1 to $L^1$-54, $L^1$-92 to $L^1$-108 | bond | $R^1$-1 to $R^1$-92 |
| Ar-3 to Ar-5 | bond or $L^1$-1 to $L^1$-4, $L^1$-92 to $L^1$-103 | $L^1$-1 to $L^1$-4 | $R^1$-1 to $R^1$-92 |
| Ar-3 to Ar-5 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Ar-5 | $L^1$-1 to $L^1$-108 | $L^1$-1 to $L^1$-54, $L^1$-92 to $L^1$-108 | $R^1$-1 to $R^1$-92 |
| Ar-5 | bond or $L^1$-1 to $L^1$-54, $L^1$-92 to $L^1$-108 | bond | $R^1$-1 to $R^1$-92 |
| Ar-5 | bond or $L^1$-1 to $L^1$-4, $L^1$-92 to $L^1$-103 | $L^1$-1 to $L^1$-4 | $R^1$-1 to $R^1$-92 |
| Ar-5 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Ar'-1 to Ar'-11 | $L^1$-1 to $L^1$-108 | $L^1$-1 to $L^1$-54, $L^1$-92 to $L^1$-108 | $R^1$-1 to $R^1$-92 |
| Ar'-1 to Ar'-11 | bond or $L^1$-1 to $L^1$-54, $L^1$-92 to $L^1$-108 | bond | $R^1$-1 to $R^1$-92 |
| Ar'-1 to Ar'-11 | bond or $L^1$-1 to $L^1$-4, $L^1$-92 to $L^1$-103 | $L^1$-1 to $L^1$-4 | $R^1$-1 to $R^1$-92 |
| Ar'-1 to Ar'-11 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Ar'-3 to Ar'-11 | $L^1$-1 to $L^1$-108 | $L^1$-1 to $L^1$-54, $L^1$-92 to $L^1$-108 | $R^1$-1 to $R^1$-92 |
| Ar'-3 to Ar'-11 | bond or $L^1$-1 to $L^1$-54, $L^1$-92 to $L^1$-108 | bond | $R^1$-1 to $R^1$-92 |
| Ar'-3 to Ar'-11 | bond or $L^1$-1 to $L^1$-4, $L^1$-92 to $L^1$-103 | $L^1$-1 to $L^1$-4 | $R^1$-1 to $R^1$-92 |
| Ar'-3 to Ar'-11 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Ar'-3 to Ar'-5 | $L^1$-1 to $L^1$-108 | $L^1$-1 to $L^1$-54, $L^1$-92 to $L^1$-108 | $R^1$-1 to $R^1$-92 |
| Ar'-3 to Ar'-5 | bond or $L^1$-1 to $L^1$-54, $L^1$-92 to $L^1$-108 | bond | $R^1$-1 to $R^1$-92 |
| Ar'-3 to Ar'-5 | bond or $L^1$-1 to $L^1$-4, $L^1$-92 to $L^1$-103 | $L^1$-1 to $L^1$-4 | $R^1$-1 to $R^1$-92 |
| Ar'-3 to Ar'-5 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Ar'-5 | $L^1$-1 to $L^1$-108 | $L^1$-1 to $L^1$-54, $L^1$-92 to $L^1$-108 | $R^1$-1 to $R^1$-92 |
| Ar'-5 | bond or $L^1$-1 to $L^1$-54, $L^1$-92 to $L^1$-108 | bond | $R^1$-1 to $R^1$-92 |
| Ar'-5 | bond or $L^1$-1 to $L^1$-4, $L^1$-92 to $L^1$-103 | $L^1$-1 to $L^1$-4 | $R^1$-1 to $R^1$-92 |

-continued

| at least one $R^a$ comprises one of the groups | $L^1$ | $L^1$ (preferred) | $Ar^1$ or $R^1$ (if present) |
|---|---|---|---|
| Ar'-5 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |

In a particularly preferred embodiment, both $R^a$ radicals are the same. Preference is given here to structures of the formulae (IIIa) and (IIIb), particular preference to structures of the formula (IIIb).

Particular preference is further given to inventive compounds having structures of the formulae (IVa), (IVb) and (IVc) where the index n is an integer in the range from 0 to 4, preferably 0 to 2 and more preferably 0, which have the following properties:

| at least one $R^a$ comprises one of the groups | where $Ar^3$, $Ar^4$ | $Ar^2$ | $R^1$ (if present) |
|---|---|---|---|
| H-1 to H-3 | $R^1$-1 to $R^1$-92 | $L^1$-1 to $L^1$-108 | $R^1$-1 to $R^1$-92 |
| H-1 to H-3 | $R^1$-1 to $R^1$-92 | bond | $R^1$-1 to $R^1$-92 |
| H-1 to H-3 | $R^1$-1 to $R^1$-92 | $L^1$-1 to $L^1$-4 | $R^1$-1 to $R^1$-92 |
| H-1 | $R^1$-2 to $R^1$-32 | bond, $L^1$-1 to $L^1$-4 | $R^1$-1 to $R^1$-92 |
| H-1 | $R^1$-2 to $R^1$-32 | $L^1$-41 to $L^1$-54 | $R^1$-1 to $R^1$-92 |
| H-1 | $R^1$-1 | bond, $L^1$-1 to $L^1$-4 | $R^1$-1 to $R^1$-92 |
| H-1 | $R^1$-1 | $L^1$-41 to $L^1$-54 | $R^1$-1 to $R^1$-92 |
| H-2 | $R^1$-2 to $R^1$-32 | bond, $L^1$-1 to $L^1$-4 | $R^1$-1 to $R^1$-92 |
| H-2 | $R^1$-2 to $R^1$-32 | $L^1$-41 to $L^1$-54 | $R^1$-1 to $R^1$-92 |
| H-2 | $R^1$-1 | bond, $L^1$-1 to $L^1$-4 | $R^1$-1 to $R^1$-92 |
| H-2 | $R^1$-1 | $L^1$-41 to $L^1$-54 | $R^1$-1 to $R^1$-92 |
| H-3 | $R^1$-2 to $R^1$-32 | bond, $L^1$-1 to $L^1$-4 | $R^1$-1 to $R^1$-92 |
| H-3 | $R^1$-2 to $R^1$-32 | $L^1$-41 to $L^1$-54 | $R^1$-1 to $R^1$-92 |
| H-3 | $R^1$-1 | bond, $L^1$-1 to $L^1$-4 | $R^1$-1 to $R^1$-92 |
| H-3 | $R^1$-1 | $L^1$-41 to $L^1$-54 | $R^1$-1 to $R^1$-92 |

In a particularly preferred embodiment, all four R radicals are the same. Preference is given here to structures of the formulae (IVa) and (IVb), particular preference to structures of the formula (IVa).

Particular preference is further given to inventive compounds having structures of the formulae (IVa), (IVb) and (IVc) where the index n is an integer in the range from 0 to 4, preferably 0 to 2 and more preferably 0, which have the following properties:

| at least one $R^a$ comprises one of the groups | $Ar^2$ | $Ar^2$ (preferred) | $Ar^1$ or $R^1$ (if present) |
|---|---|---|---|
| H-4 to H-26 | $L^1$-1 to $L^1$-108 | $L^1$-1 to $L^1$-54, $L^1$-92 to $L^1$-108 | $R^1$-1 to $R^1$-92 |
| H-4 to H-26 | bond or $L^1$-1 to $L^1$-54, $L^1$-92 to $L^1$-108 | bond | $R^1$-1 to $R^1$-92 |
| H-4 to H-26 | bond or $L^1$-1 to $L^1$-4, $L^1$-92 to $L^1$-103 | $L^1$-1 to $L^1$-4 | $R^1$-1 to $R^1$-92 |
| H-4 to H-26 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-4 | $L^1$-1 to $L^1$-108 | $L^1$-1 to $L^1$-54, $L^1$-92 to $L^1$-108 | $R^1$-1 to $R^1$-92 |
| H-4 | bond or $L^1$-1 to $L^1$-54, $L^1$-92 to $L^1$-108 | bond | $R^1$-1 to $R^1$-92 |
| H-4 | bond or $L^1$-1 to $L^1$-4, $L^1$-92 to $L^1$-103 | $L^1$-1 to $L^1$-4 | $R^1$-1 to $R^1$-92 |
| H-4 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-5 | $L^1$-1 to $L^1$-108 | $L^1$-1 to $L^1$-54, $L^1$-92 to $L^1$-108 | $R^1$-1 to $R^1$-92 |
| H-5 | bond or $L^1$-1 to $L^1$-54, $L^1$-92 to $L^1$-108 | bond | $R^1$-1 to $R^1$-92 |
| H-5 | bond or $L^1$-1 to $L^1$-4, $L^1$-92 to $L^1$-103 | $L^1$-1 to $L^1$-4 | $R^1$-1 to $R^1$-92 |
| H-5 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-6 | $L^1$-1 to $L^1$-108 | $L^1$-1 to $L^1$-54, $L^1$-92 to $L^1$-108 | $R^1$-1 to $R^1$-92 |
| H-6 | bond or $L^1$-1 to $L^1$-54, $L^1$-92 to $L^1$-108 | bond | $R^1$-1 to $R^1$-92 |
| H-6 | bond or $L^1$-1 to $L^1$-4, $L^1$-92 to $L^1$-103 | $L^1$-1 to $L^1$-4 | $R^1$-1 to $R^1$-92 |
| H-6 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-7 | $L^1$-1 to $L^1$-108 | $L^1$-1 to $L^1$-54, $L^1$-92 to $L^1$-108 | $R^1$-1 to $R^1$-92 |
| H-7 | bond or $L^1$-1 to $L^1$-54, $L^1$-92 to $L^1$-108 | bond | $R^1$-1 to $R^1$-92 |
| H-7 | bond or $L^1$-1 to $L^1$-4, $L^1$-92 to $L^1$-103 | $L^1$-1 to $L^1$-4 | $R^1$-1 to $R^1$-92 |
| H-7 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-8 | $L^1$-1 to $L^1$-108 | $L^1$-1 to $L^1$-54, $L^1$-92 to $L^1$-108 | $R^1$-1 to $R^1$-92 |
| H-8 | bond or $L^1$-1 to $L^1$-54, $L^1$-92 to $L^1$-108 | bond | $R^1$-1 to $R^1$-92 |
| H-8 | bond or $L^1$-1 to $L^1$-4, $L^1$-92 to $L^1$-103 | $L^1$-1 to $L^1$-4 | $R^1$-1 to $R^1$-92 |
| H-8 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |

In a particularly preferred embodiment, all four $R^a$ radicals are the same. Preference is given here to structures of the formulae (IVa) and (IVb), particular preference to structures of the formula (IVa).

Particular preference is further given to inventive compounds having structures of the formulae (IVa), (IVb) and (IVc) where the index n is an integer in the range from 0 to 4, preferably 0 to 2 and more preferably 0, which have the following properties:

| at least one $R^a$ comprises one of the groups | $L^1$ | $L^1$ (preferred) | $Ar^1$ or $R^1$ (if present) |
|---|---|---|---|
| Q-1 to Q-44 | $L^1$-1 to $L^1$-108 | $L^1$-1 to $L^1$-54, $L^1$-92 to $L^1$-108 | $R^1$-1 to $R^1$-92 |
| Q-1 to Q-44 | bond or $L^1$-1 to $L^1$-54, $L^1$-92 to $L^1$-108 | bond | $R^1$-1 to $R^1$-92 |
| Q-1 to Q-44 | bond or $L^1$-1 to $L^1$-4, $L^1$-92 to $L^1$-103 | $L^1$-1 to $L^1$-4 | $R^1$-1 to $R^1$-92 |
| Q-1 to Q-44 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Q-11 to Q-25 | $L^1$-1 to $L^1$-108 | $L^1$-1 to $L^1$-54, $L^1$-92 to $L^1$-108 | $R^1$-1 to $R^1$-92 |
| Q-11 to Q-25 | bond or $L^1$-1 to $L^1$-54, $L^1$-92 to $L^1$-108 | bond | $R^1$-1 to $R^1$-92 |

| at least one R<sup>a</sup> comprises one of the groups | L¹ | L¹ (preferred) | Ar¹ or R¹ (if present) |
|---|---|---|---|
| Q-11 to Q-25 | bond or L¹-1 to L¹-4, L¹-92 to L¹-103 | L¹-1 to L¹-4 | R¹-1 to R¹-92 |
| Q-11 to Q-25 | L¹-30 to L¹-52 or L¹-104 to L¹-108 | L¹-37 to L¹-52 or L¹-106 to L¹-108 | R¹-1 to R¹-92 |
| Q-26 to Q-44, preferably Q-26 to Q-42 | L¹-1 to L¹-108 | L¹-1 to L¹-54, L¹-92 to L¹-108 | R¹-1 to R¹-92 |
| Q-26 to Q-44, preferably Q-26 to Q-42 | bond or L¹-1 to L¹-54, L¹-92 to L¹-108 | bond | R¹-1 to R¹-92 |
| Q-26 to Q-44, preferably Q-26 to Q-42 | bond or L¹-1 to L¹-4, L¹-92 to L¹-103 | L¹-1 to L¹-4 | R¹-1 to R¹-92 |
| Q-26 to Q-44, preferably Q-26 to Q-42 | L¹-30 to L¹-52 or L¹-104 to L¹-108 | L¹-37 to L¹-52 or L¹-106 to L¹-108 | R¹-1 to R¹92 |
| Q-23 to Q-25 | L¹-1 to L¹-108 | L¹-1 to L¹-54, L¹-92 to L¹-108 | R¹-1 to R¹-92 |
| Q-23 to Q-25 | bond or L¹-1 to L¹-54, L¹-92 to L¹-108 | bond | R¹-1 to R¹-92 |
| Q-23 to Q-25 | bond or L¹-1 to L¹-4, L¹-92 to L¹-103 | L¹-1 to L¹-4 | R¹-1 to R¹-92 |
| Q-23 to Q-25 | L¹-30 to L¹-52 or L¹-104 to L¹-108 | L¹-37 to L¹-52 or L¹-106 to L¹-108 | R¹-1 to R¹-92 |
| Q-23 | L¹-1 to L¹-108 | L¹-1 to L¹-54, L¹-92 to L¹-108 | R¹-1 to R¹-92 |
| Q-23 | bond or L¹-1 to L¹-54, L¹-92 to L¹-108 | bond | R¹-1 to R¹-92 |
| Q-23 | bond or L¹-1 to L¹-4, L¹-92 to L¹-103 | L¹-1 to L¹-4 | R¹-1 to R¹-92 |
| Q-23 | L¹-30 to L¹-52 or L¹-104 to L¹-108 | L¹-37 to L¹-52 or L¹-106 to L¹-108 | R¹-1 to R¹-92 |

In a particularly preferred embodiment, all four R<sup>a</sup> radicals are the same. Preference is given here to structures of the formulae (IVa) and (IVb), particular preference to structures of the formula (IVa).

Particular preference is further given to inventive compounds having structures of the formulae (IVa), (IVb) and (IVc) where the index n is an integer in the range from 0 to 4, preferably 0 to 2 and more preferably 0, which have the following properties:

| at least one R<sup>a</sup> comprises one of the groups | L¹ | L¹ (preferred) | Ar¹ or R¹ (if present) |
|---|---|---|---|
| Ar-1 to Ar-11 | L¹-1 to L¹-108 | L¹-1 to L¹-54, L¹-92 to L¹-108 | R¹-1 to R¹-92 |
| Ar-1 to Ar-11 | bond or L¹-1 to L¹-54, L¹-92 to L¹-108 | bond | R¹-1 to R¹-92 |
| Ar-1 to Ar-11 | bond or L¹-1 to L¹-4, L¹-92 to L¹-103 | L¹-1 to L¹-4 | R¹-1 to R¹-92 |
| Ar-1 to Ar-11 | L¹-30 to L¹-52 or L¹-104 to L¹-108 | L¹-37 to L¹-52 or L¹-106 to L¹-108 | R¹-1 to R¹-92 |
| Ar-3 to Ar-11 | L¹-1 to L¹-108 | L¹-1 to L¹-54, L¹-92 to L¹-108 | R¹-1 to R¹-92 |
| Ar-3 to Ar-11 | bond or L¹-1 to L¹-54, L¹-92 to L¹-108 | bond | R¹-1 to R¹-92 |
| Ar-3 to Ar-11 | bond or L¹-1 to L¹-4, L¹-92 to L¹-103 | L¹-1 to L¹-4 | R¹-1 to R¹-92 |
| Ar-3 to Ar-11 | L¹-30 to L¹-52 or L¹-104 to L¹-108 | L¹-37 to L¹-52 or L¹-106 to L¹-108 | R¹-1 to R¹-92 |
| Ar-3 to Ar-5 | L¹-1 to L¹-108 | L¹-1 to L¹-54, L¹-92 to L¹-108 | R¹-1 to R¹-92 |
| Ar-3 to Ar-5 | bond or L¹-1 to L¹-54, L¹-92 to L¹-108 | bond | R¹-1 to R¹-92 |
| Ar-3 to Ar-5 | bond or L¹-1 to L¹-4, L¹-92 to L¹-103 | L¹-1 to L¹-4 | R¹-1 to R¹-92 |
| Ar-3 to Ar-5 | L¹-30 to L¹-52 or L¹-104 to L¹-108 | L¹-37 to L¹-52 or L¹-106 to L¹-108 | R¹-1 to R¹-92 |
| Ar-5 | L¹-1 to L¹-108 | L¹-1 to L¹-54, L¹-92 to L¹-108 | R¹-1 to R¹-92 |
| Ar-5 | bond or L¹-1 to L¹-54, L¹-92 to L¹-108 | bond | R¹-1 to R¹-92 |
| Ar-5 | bond or L¹-1 to L¹-4, L¹-92 to L¹-103 | L¹-1 to L¹-4 | R¹-1 to R¹-92 |
| Ar-5 | L¹-30 to L¹-52 or L¹-104 to L¹-108 | L¹-37 to L¹-52 or L¹-106 to L¹-108 | R¹-1 to R¹-92 |
| Ar'-1 to Ar'-11 | L¹-1 to L¹-108 | L¹-1 to L¹-54, L¹-92 to L¹-108 | R¹-1 to R¹-92 |
| Ar'-1 to Ar'-11 | bond or L¹-1 to L¹-54, L¹-92 to L¹-108 | bond | R¹-1 to R¹-92 |
| Ar'-1 to Ar'-11 | bond or L¹-1 to L¹-4, L¹-92 to L¹-103 | L¹-1 to L¹-4 | R¹-1 to R¹-92 |
| Ar'-1 to Ar'-11 | L¹-30 to L¹-52 or L¹-104 to L¹-108 | L¹-37 to L¹-52 or L¹-106 to L¹-108 | R¹-1 to R¹-92 |
| Ar'-3 to Ar'-11 | L¹-1 to L¹-108 | L¹-1 to L¹-54, L¹-92 to L¹-108 | R¹-1 to R¹-92 |
| Ar'-3 to Ar'-11 | bond or L¹-1 to L¹-54, L¹-92 to L¹-108 | bond | R¹-1 to R¹-92 |
| Ar'-3 to Ar'-11 | bond or L¹-1 to L¹-4, L¹-92 to L¹-103 | L¹-1 to L¹-4 | R¹-1 to R¹-92 |
| Ar'-3 to Ar'-11 | L¹-30 to L¹-52 or L¹-104 to L¹-108 | L¹-37 to L¹-52 or L¹-106 to L¹-108 | R¹-1 to R¹-92 |
| Ar'-3 to Ar'-5 | L¹-1 to L¹-108 | L¹-1 to L¹-54, L¹-92 to L¹-108 | R¹-1 to R¹-92 |
| Ar'-3 to Ar'-5 | bond or L¹-1 to L¹-54, L¹-92 to L¹-108 | bond | R¹-1 to R¹-92 |
| Ar'-3 to Ar'-5 | bond or L¹-1 to L¹-4, L¹-92 to L¹-103 | L¹-1 to L¹-4 | R¹-1 to R¹-92 |
| Ar'-3 to Ar'-5 | L¹-30 to L¹-52 or L¹-104 to L¹-108 | L¹-37 to L¹-52 or L¹-106 to L¹-108 | R¹-1 to R¹-92 |
| Ar'-5 | L¹-1 to L¹-108 | L¹-1 to L¹-54, L¹-92 to L¹-108 | R¹-1 to R¹-92 |
| Ar'-5 | bond or L¹-1 to L¹-54, L¹-92 to L¹-108 | bond | R¹-1 to R¹-92 |
| Ar'-5 | bond or L¹-1 to L¹-4, L¹-92 to L¹-103 | L¹-1 to L¹-4 | R¹-1 to R¹-92 |
| Ar'-5 | L¹-30 to L¹-52 or L¹-104 to L¹-108 | L¹-37 to L¹-52 or L¹-106 to L¹-108 | R¹-1 to R¹-92 |

In a particularly preferred embodiment, all four R<sup>a</sup> radicals are the same. Preference is given here to structures of the formulae (IVa) and (IVb), particular preference to structures of the formula (IVa).

Particular preference is further given to inventive compounds having structures of the formula (V) that have the following properties:

| at least one R<sup>a</sup> comprises one of the groups | where Ar³, Ar⁴ | Ar² | R¹ (if present) |
|---|---|---|---|
| H-1 to H-3 | R¹-1 to R¹-92 | L¹-1 to L¹-108 | R¹-1 to R¹-92 |
| H-1 to H-3 | R¹-1 to R¹-92 | bond | R¹-1 to R¹-92 |
| H-1 to H-3 | R¹-1 to R¹-92 | L¹-1 to L¹-4 | R¹-1 to R¹-92 |
| H-1 | R¹-2 to R¹-32 | bond, L¹-1 to L¹-4 | R¹-1 to R¹-92 |
| H-1 | R¹-2 to R¹-32 | L¹-41 to L¹-54 | R¹-1 to R¹-92 |
| H-1 | R¹-1 | bond, L¹-1 to L¹-4 | R¹-1 to R¹-92 |
| H-1 | R¹-1 | L¹-41 to L¹-54 | R¹-1 to R¹-92 |
| H-2 | R¹-2 to R¹-32 | bond, L¹-1 to L¹-4 | R¹-1 to R¹-92 |
| H-2 | R¹-2 to R¹-32 | L¹-41 to L¹-54 | R¹-1 to R¹-92 |
| H-2 | R¹-1 | bond, L¹-1 to L¹-4 | R¹-1 to R¹-92 |

| at least one $R^a$ comprises one of the groups | where $Ar^3$, $Ar^4$ | $Ar^2$ | $R^1$ (if present) |
|---|---|---|---|
| H-2 | $R^1$-1 | $L^1$-41 to $L^1$-54 | $R^1$-1 to $R^1$-92 |
| H-3 | $R^1$-2 to $R^1$-32 | bond, $L^1$-1 to $L^1$-4 | $R^1$-1 to $R^1$-92 |
| H-3 | $R^1$-2 to $R^1$-32 | $L^1$-41 to $L^1$-54 | $R^1$-1 to $R^1$-92 |
| H-3 | $R^1$-1 | bond, $L^1$-1 to $L^1$-4 | $R^1$-1 to $R^1$-92 |
| H-3 | $R^1$-1 | $L^1$-41 to $L^1$-54 | $R^1$-1 to $R^1$-92 |

In a particularly preferred embodiment, all $R^a$ radicals are the same.

Particular preference is further given to inventive compounds having structures of the formula (V) that have the following properties:

| at least one $R^a$ comprises one of the groups | $Ar^2$ | $Ar^2$ (preferred) | $Ar^1$ or $R^1$ (if present) |
|---|---|---|---|
| H-4 to H-26 | $L^1$-1 to $L^1$-108 | $L^1$-1 to $L^1$-54, $L^1$-92 to $L^1$-108 | $R^1$-1 to $R^1$-92 |
| H-4 to H-26 | bond or $L^1$-1 to $L^1$-54, $L^1$-92 to $L^1$-108 | bond | $R^1$-1 to $R^1$-92 |
| H-4 to H-26 | bond or $L^1$-1 to $L^1$-4, $L^1$-92 to $L^1$-103 | $L^1$-1 to $L^1$-4 | $R^1$-1 to $R^1$-92 |
| H-4 to H-26 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-4 | $L^1$-1 to $L^1$-108 | $L^1$-1 to $L^1$-54, $L^1$-92 to $L^1$-108 | $R^1$-1 to $R^1$-92 |
| H-4 | bond or $L^1$-1 to $L^1$-54, $L^1$-92 to $L^1$-108 | bond | $R^1$-1 to $R^1$-92 |
| H-4 | bond or $L^1$-1 to $L^1$-4, $L^1$-92 to $L^1$-103 | $L^1$-1 to $L^1$-4 | $R^1$-1 to $R^1$-92 |
| H-4 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-5 | $L^1$-1 to $L^1$-108 | $L^1$-1 to $L^1$-54, $L^1$-92 to $L^1$-108 | $R^1$-1 to $R^1$-92 |
| H-5 | bond or $L^1$-1 to $L^1$-54, $L^1$-92 to $L^1$-108 | bond | $R^1$-1 to $R^1$-92 |
| H-5 | bond or $L^1$-1 to $L^1$-4, $L^1$-92 to $L^1$-103 | $L^1$-1 to $L^1$-4 | $R^1$-1 to $R^1$-92 |
| H-5 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-6 | $L^1$-1 to $L^1$-108 | $L^1$-1 to $L^1$-54, $L^1$-92 to $L^1$-108 | $R^1$-1 to $R^1$-92 |
| H-6 | bond or $L^1$-1 to $L^1$-54, $L^1$-92 to $L^1$-108 | bond | $R^1$-1 to $R^1$-92 |
| H-6 | bond or $L^1$-1 to $L^1$-4, $L^1$-92 to $L^1$-103 | $L^1$-1 to $L^1$-4 | $R^1$-1 to $R^1$-92 |
| H-6 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-7 | $L^1$-1 to $L^1$-108 | $L^1$-1 to $L^1$-54, $L^1$-92 to $L^1$-108 | $R^1$-1 to $R^1$-92 |
| H-7 | bond or $L^1$-1 to $L^1$-54, $L^1$-92 to $L^1$-108 | bond | $R^1$-1 to $R^1$-92 |
| H-7 | bond or $L^1$-1 to $L^1$-4, $L^1$-92 to $L^1$-103 | $L^1$-1 to $L^1$-4 | $R^1$-1 to $R^1$-92 |
| H-7 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| H-8 | $L^1$-1 to $L^1$-108 | $L^1$-1 to $L^1$-54, $L^1$-92 to $L^1$-108 | $R^1$-1 to $R^1$-92 |
| H-8 | bond or $L^1$-1 to $L^1$-54, $L^1$-92 to $L^1$-108 | bond | $R^1$-1 to $R^1$-92 |
| H-8 | bond or $L^1$-1 to $L^1$-4, $L^1$-92 to $L^1$-103 | $L^1$-1 to $L^1$-4 | $R^1$-1 to $R^1$-92 |
| H-8 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |

In a particularly preferred embodiment, all $R^a$ radicals are the same.

Particular preference is further given to inventive compounds having structures of the formula (V) that have the following properties:

| at least one $R^a$ comprises one of the groups | $L^1$ | $L^1$ (preferred) | $Ar^1$ or $R^1$ (if present) |
|---|---|---|---|
| Q-1 to Q-44 | $L^1$-1 to $L^1$-108 | $L^1$-1 to $L^1$-54, $L^1$-92 to $L^1$-108 | $R^1$-1 to $R^1$-92 |
| Q-1 to Q-44 | bond or $L^1$-1 to $L^1$-54, $L^1$-92 to $L^1$-108 | bond | $R^1$-1 to $R^1$-92 |
| Q-1 to Q-44 | bond or $L^1$-1 to $L^1$-4, $L^1$-92 to $L^1$-103 | $L^1$-1 to $L^1$-4 | $R^1$-1 to $R^1$-92 |
| Q-1 to Q-44 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Q-11 to Q-25 | $L^1$-1 to $L^1$-108 | $L^1$-1 to $L^1$-54, $L^1$-92 to $L^1$-108 | $R^1$-1 to $R^1$-92 |
| Q-11 to Q-25 | bond or $L^1$-1 to $L^1$-54, $L^1$-92 to $L^1$-108 | bond | $R^1$-1 to $R^1$-92 |
| Q-11 to Q-25 | bond or $L^1$-1 to $L^1$-4, $L^1$-92 to $L^1$-103 | $L^1$-1 to $L^1$-4 | $R^1$-1 to $R^1$-92 |
| Q-11 to Q-25 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Q-26 to Q-44, preferably Q-26 to Q-42 | $L^1$-1 to $L^1$-108 | $L^1$-1 to $L^1$-54, $L^1$-92 to $L^1$-108 | $R^1$-1 to $R^1$-92 |
| Q-26 to Q-44, preferably Q-26 to Q-42 | bond or $L^1$-1 to $L^1$-54, $L^1$-92 to $L^1$-108 | bond | $R^1$-1 to $R^1$-92 |
| Q-26 to Q-44, preferably Q-26 to Q-42 | bond or $L^1$-1 to $L^1$-4, $L^1$-92 to $L^1$-103 | $L^1$-1 to $L^1$-4 | $R^1$-1 to $R^1$-92 |
| Q-26 to Q-44, preferably Q-26 to Q-42 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Q-23 to Q-25 | $L^1$-1 to $L^1$-108 | $L^1$-1 to $L^1$-54, $L^1$-92 to $L^1$-108 | $R^1$-1 to $R^1$-92 |
| Q-23 to Q-25 | bond or $L^1$-1 to $L^1$-54, $L^1$-92 to $L^1$-108 | bond | $R^1$-1 to $R^1$-92 |
| Q-23 to Q-25 | bond or $L^1$-1 to $L^1$-4, $L^1$-92 to $L^1$-103 | $L^1$-1 to $L^1$-4 | $R^1$-1 to $R^1$-92 |
| Q-23 to Q-25 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Q-23 | $L^1$-1 to $L^1$-108 | $L^1$-1 to $L^1$-54, $L^1$-92 to $L^1$-108 | $R^1$-1 to $R^1$-92 |
| Q-23 | bond or $L^1$-1 to $L^1$-54, $L^1$-92 to $L^1$-108 | bond | $R^1$-1 to $R^1$-92 |
| Q-23 | bond or $L^1$-1 to $L^1$-4, $L^1$-92 to $L^1$-103 | $L^1$-1 to $L^1$-4 | $R^1$-1 to $R^1$-92 |
| Q-23 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |

In a particularly preferred embodiment, all $R^a$ radicals are the same.

Particular preference is further given to inventive compounds having structures of the formula (V) that have the following properties:

| at least one $R^a$ comprises one of the groups | $L^1$ | $L^1$ (preferred) | $Ar^1$ or R (if present) |
|---|---|---|---|
| Ar-1 to Ar-11 | $L^1$-1 to $L^1$-108 | $L^1$-1 to $L^1$-54, $L^1$-92 to $L^1$-108 | $R^1$-1 to $R^1$-92 |
| Ar-1 to Ar-11 | bond or $L^1$-1 to $L^1$-54, $L^1$-92 to $L^1$-108 | bond | $R^1$-1 to $R^1$-92 |
| Ar-1 to Ar-11 | bond or $L^1$-1 to $L^1$-4, $L^1$-92 to $L^1$-103 | $L^1$-1 to $L^1$-4 | $R^1$-1 to $R^1$-92 |
| Ar-1 to Ar-11 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Ar-3 to Ar-11 | $L^1$-1 to $L^1$-108 | $L^1$-1 to $L^1$-54, $L^1$-92 to $L^1$-108 | $R^1$-1 to $R^1$-92 |
| Ar-3 to Ar-11 | bond or $L^1$-1 to $L^1$-54, $L^1$-92 to $L^1$-108 | bond | $R^1$-1 to $R^1$-92 |
| Ar-3 to Ar-11 | bond or $L^1$-1 to $L^1$-4, $L^1$-92 to $L^1$-103 | $L^1$-1 to $L^1$-4 | $R^1$-1 to $R^1$-92 |
| Ar-3 to Ar-11 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Ar-3 to Ar-5 | $L^1$-1 to $L^1$-108 | $L^1$-1 to $L^1$-54, $L^1$-92 to $L^1$-108 | $R^1$-1 to $R^1$-92 |
| Ar-3 to Ar-5 | bond or $L^1$-1 to $L^1$-54, $L^1$-92 to $L^1$-108 | bond | $R^1$-1 to $R^1$-92 |
| Ar-3 to Ar-5 | bond or $L^1$-1 to $L^1$-4, $L^1$-92 to $L^1$-103 | $L^1$-1 to $L^1$-4 | $R^1$-1 to $R^1$-92 |
| Ar-3 to Ar-5 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Ar-5 | $L^1$-1 to $L^1$-108 | $L^1$-1 to $L^1$-54, $L^1$-92 to $L^1$-108 | $R^1$-1 to $R^1$-92 |
| Ar-5 | bond or $L^1$-1 to $L^1$-54, $L^1$-92 to $L^1$-108 | bond | $R^1$-1 to $R^1$-92 |
| Ar-5 | bond or $L^1$-1 to $L^1$-4, $L^1$-92 to $L^1$-103 | $L^1$-1 to $L^1$-4 | $R^1$-1 to $R^1$-92 |
| Ar-5 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Ar'-1 to Ar'-11 | $L^1$-1 to $L^1$-108 | $L^1$-1 to $L^1$-54, $L^1$-92 to $L^1$-108 | $R^1$-1 to $R^1$-92 |
| Ar'-1 to Ar'-11 | bond or $L^1$-1 to $L^1$-54, $L^1$-92 to $L^1$-108 | bond | $R^1$-1 to $R^1$-92 |
| Ar'-1 to Ar'-11 | bond or $L^1$-1 to $L^1$-4, $L^1$-92 to $L^1$-103 | $L^1$-1 to $L^1$-4 | $R^1$-1 to $R^1$-92 |
| Ar'-1 to Ar'-11 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Ar'-3 to Ar'-11 | $L^1$-1 to $L^1$-108 | $L^1$-1 to $L^1$-54, $L^1$-92 to $L^1$-108 | $R^1$-1 to $R^1$-92 |
| Ar'-3 to Ar'-11 | bond or $L^1$-1 to $L^1$-54, $L^1$-92 to $L^1$-108 | bond | $R^1$-1 to $R^1$-92 |
| Ar'-3 to Ar'-11 | bond or $L^1$-1 to $L^1$-4, $L^1$-92 to $L^1$-103 | $L^1$-1 to $L^1$-4 | $R^1$-1 to $R^1$-92 |
| Ar'-3 to Ar'-11 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Ar'-3 to Ar'-5 | $L^1$-1 to $L^1$-108 | $L^1$-1 to $L^1$-54, $L^1$-92 to $L^1$-108 | $R^1$-1 to $R^1$-92 |
| Ar'-3 to Ar'-5 | bond or $L^1$-1 to $L^1$-54, $L^1$-92 to $L^1$-108 | bond | $R^1$-1 to $R^1$-92 |
| Ar'-3 to Ar'-5 | bond or $L^1$-1 to $L^1$-4, $L^1$-92 to $L^1$-103 | $L^1$-1 to $L^1$-4 | $R^1$-1 to $R^1$-92 |
| Ar'-3 to Ar'-5 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |
| Ar'-5 | $L^1$-1 to $L^1$-108 | $L^1$-1 to $L^1$-54, $L^1$-92 to $L^1$-108 | $R^1$-1 to $R^1$-92 |
| Ar'-5 | bond or $L^1$-1 to $L^1$-54, $L^1$-92 to $L^1$-108 | bond | $R^1$-1 to $R^1$-92 |
| Ar'-5 | bond or $L^1$-1 to $L^1$-4, $L^1$-92 to $L^1$-103 | $L^1$-1 to $L^1$-4 | $R^1$-1 to $R^1$-92 |
| Ar'-5 | $L^1$-30 to $L^1$-52 or $L^1$-104 to $L^1$-108 | $L^1$-37 to $L^1$-52 or $L^1$-106 to $L^1$-108 | $R^1$-1 to $R^1$-92 |

In a particularly preferred embodiment, all $R^a$ radicals are the same.

It may further be the case that the compound usable as active compound in an organic electronic device is not in direct contact with a metal atom, and is preferably not a ligand for a metal complex.

Examples of suitable compounds of the invention are the structures of the following formulae 1 to 23 shown below:

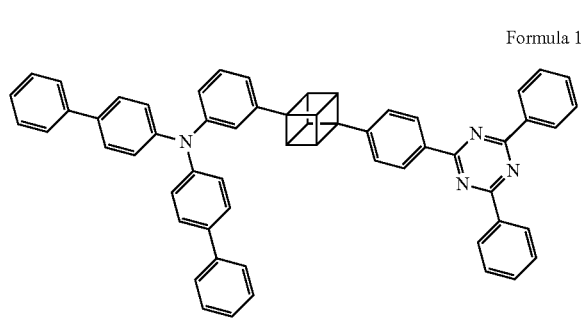

Formula 1

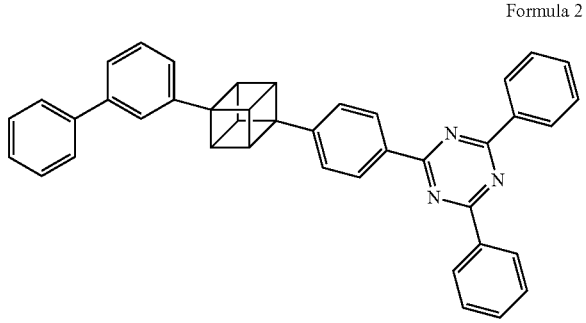

Formula 2

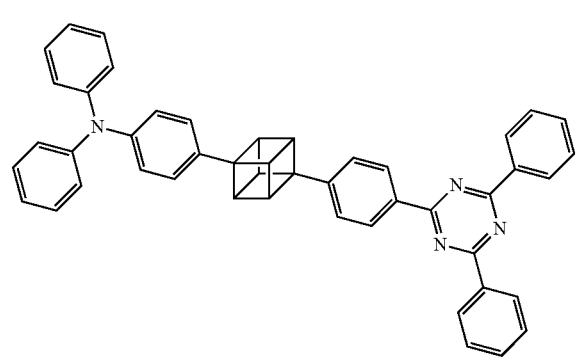

Formula 3

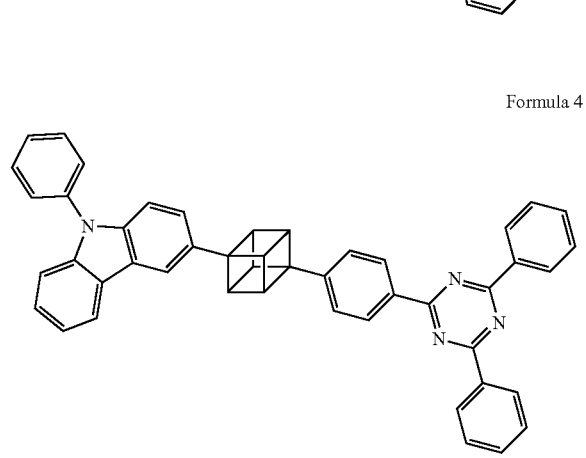

Formula 4

Formula 5
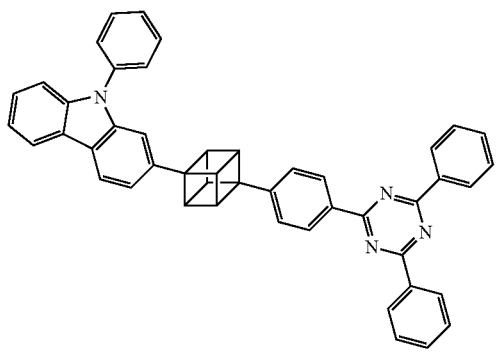
Formula 9
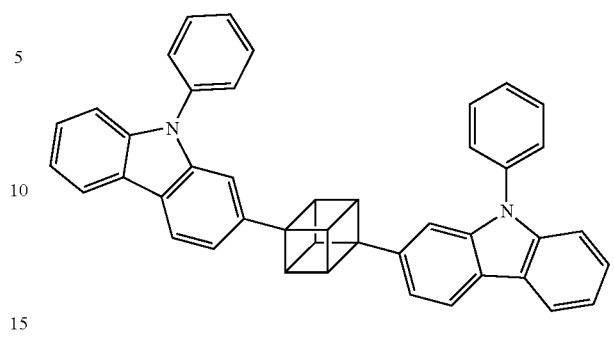
Formula 6
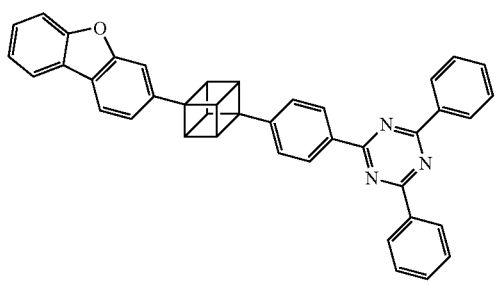
Formula 10
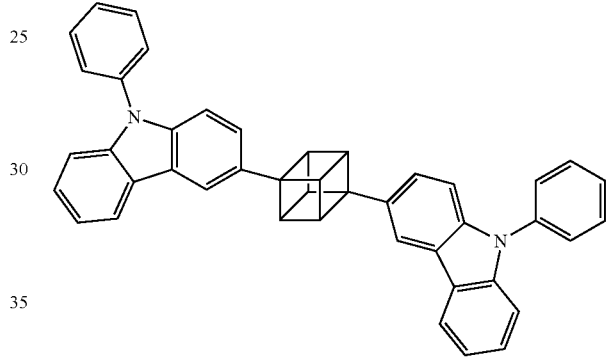
Formula 7
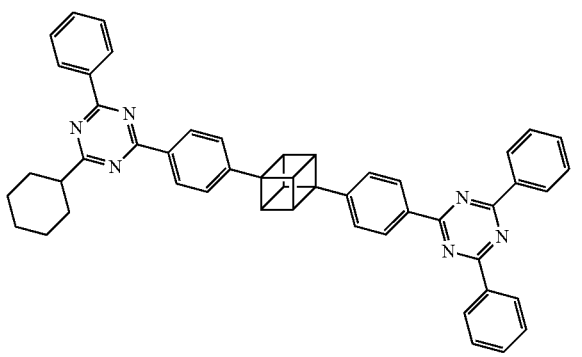
Formula 11
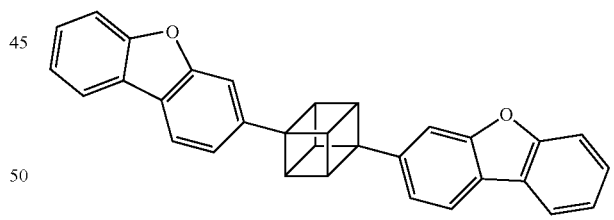
Formula 8
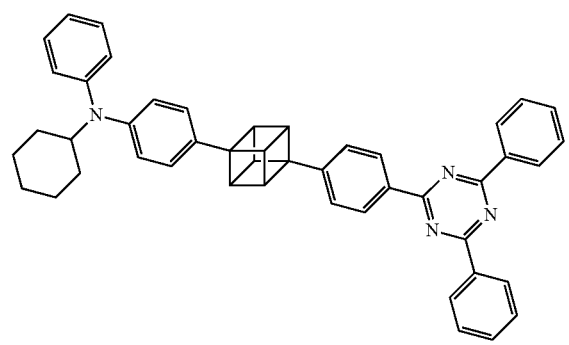
Formula 12
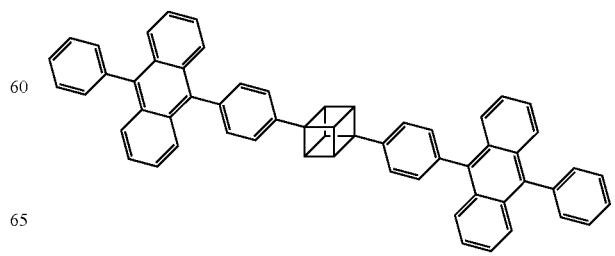

Formula 13
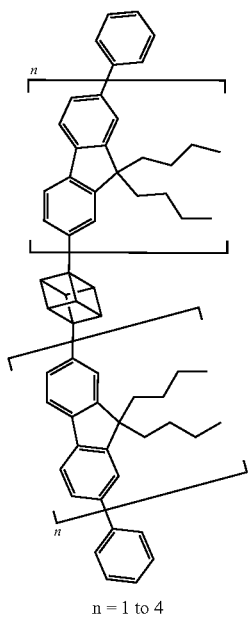
n = 1 to 4
Formula 14
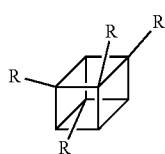
R =
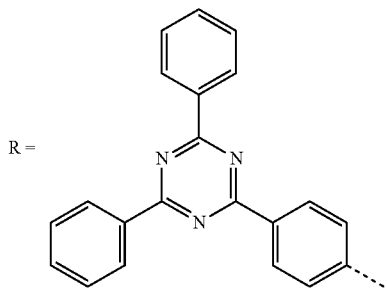
Formula 15
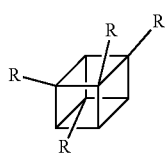
R =
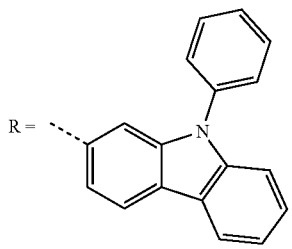
Formula 16
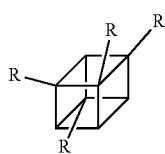
R =
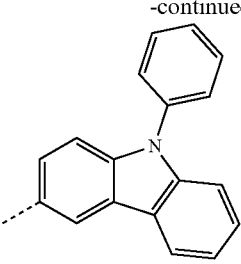
Formula 17
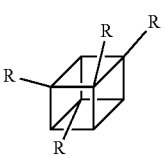
R =
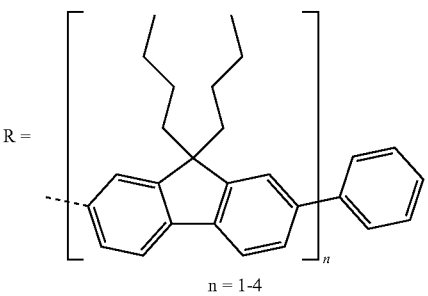
n = 1-4
Formula 18
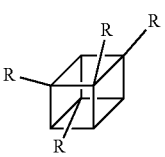
R =
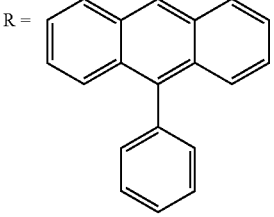
Formula 19
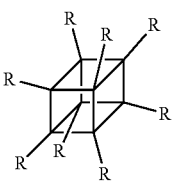

R = 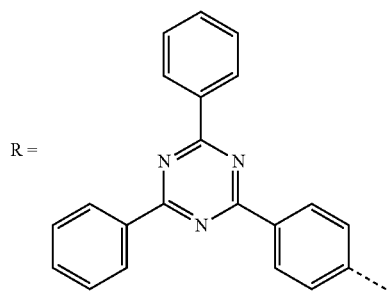
Formula 20
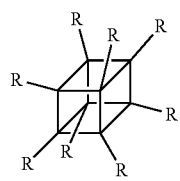
R = 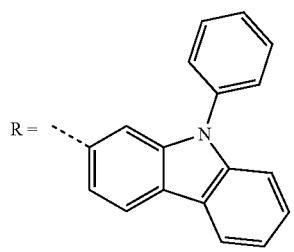
Formula 21
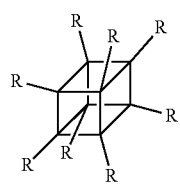
R = 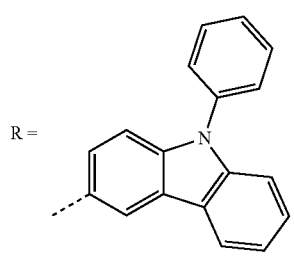
Formula 22
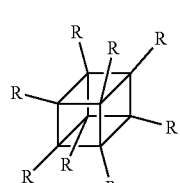
R = 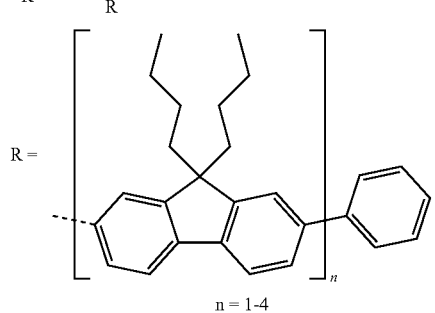
n = 1-4
Formula 23
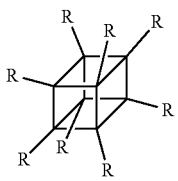
R = 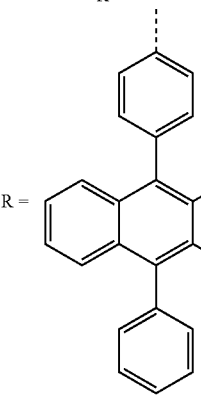
Formula 24
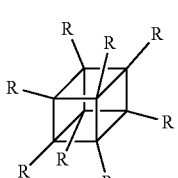
R = 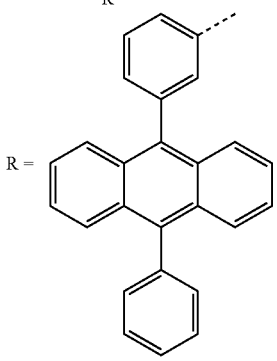
Formula 25
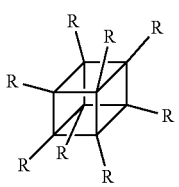
R = 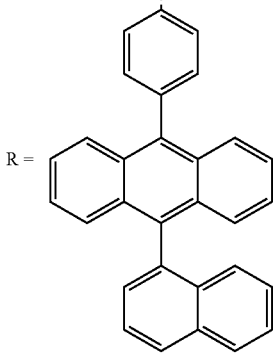

Formula 26
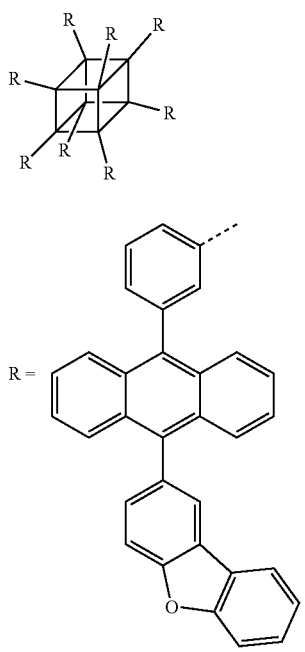
Formula 27
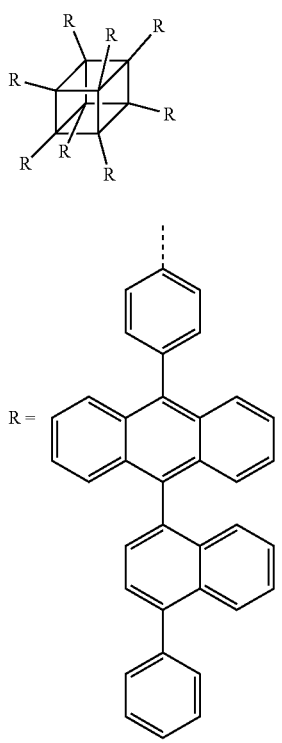
Formula 28
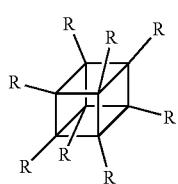
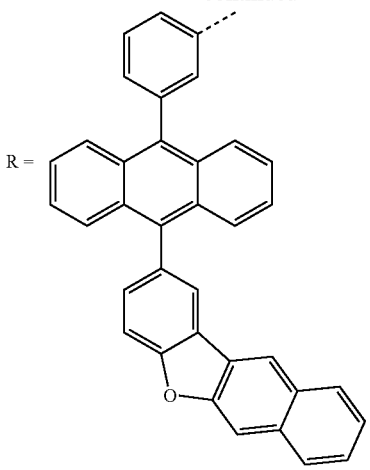
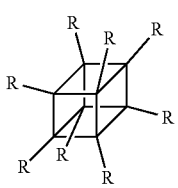
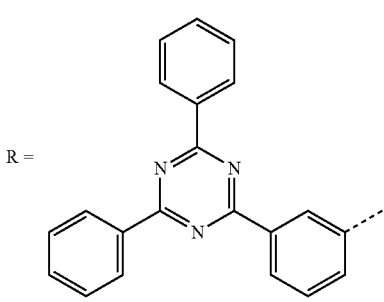
Formula 29
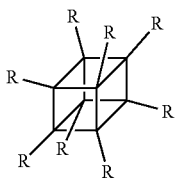
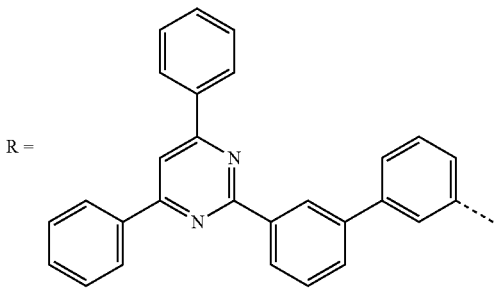
Formula 30
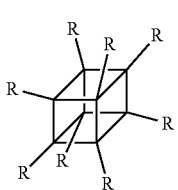
Formula 31

-continued
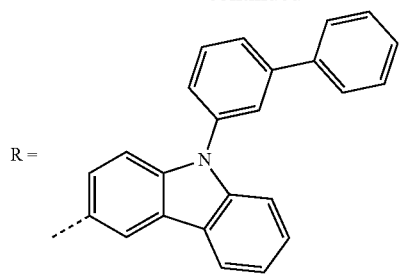
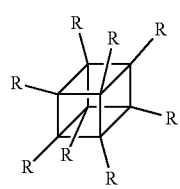
Formula 32
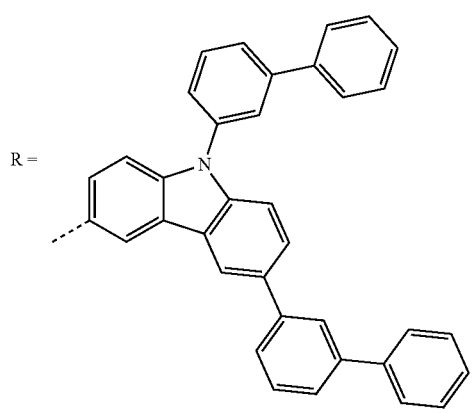
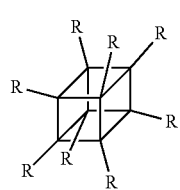
Formula 33
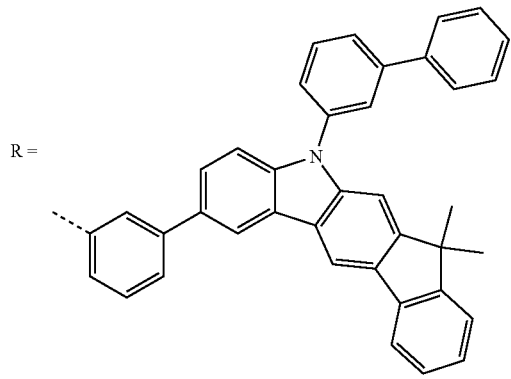
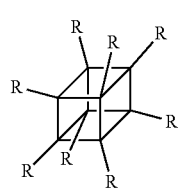
Formula 34
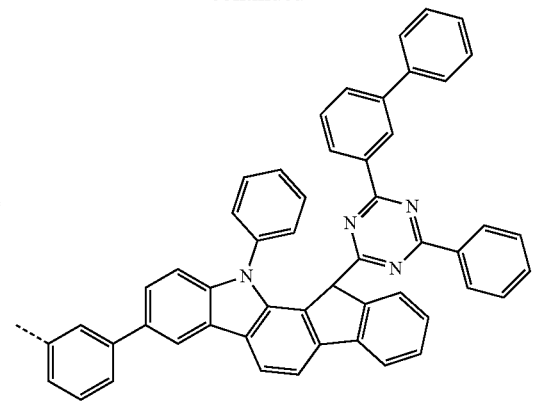
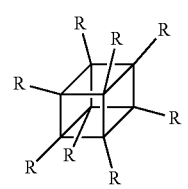
Formula 35
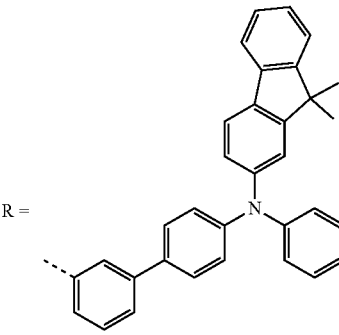
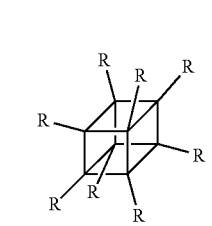
Formula 36
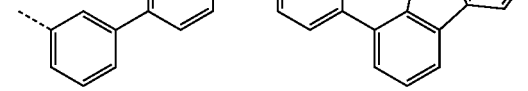
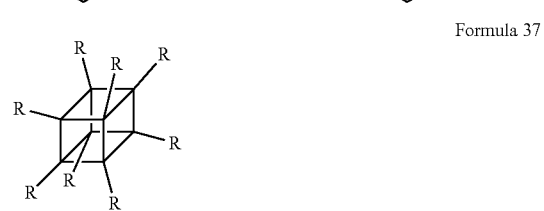
Formula 37

US 11,917,906 B2
R = 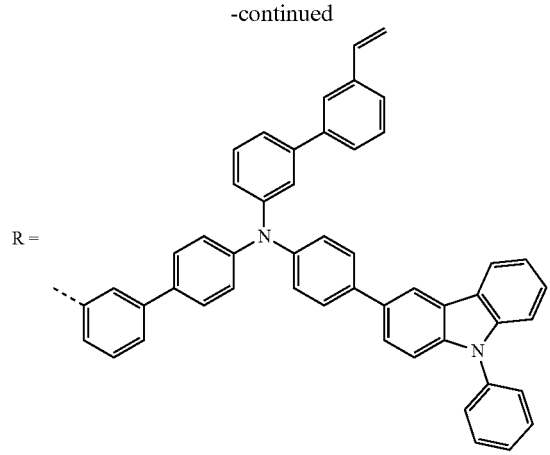
Formula 38
R = 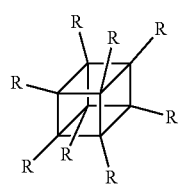
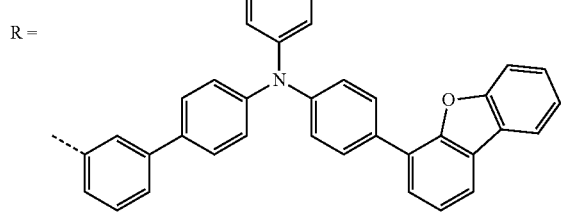
Formula 39
R = 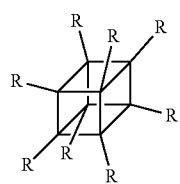
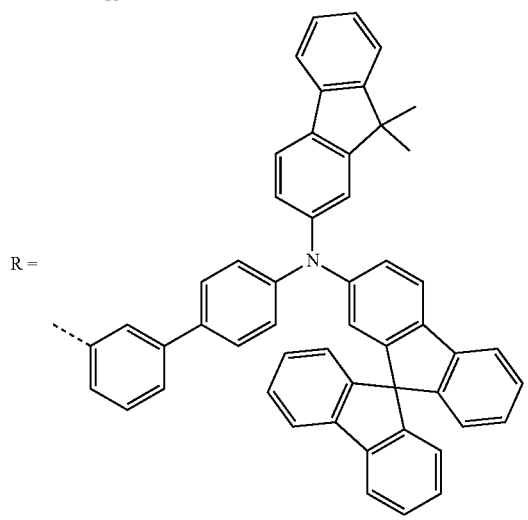
Formula 40
R = 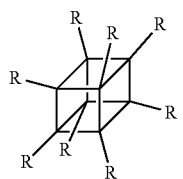
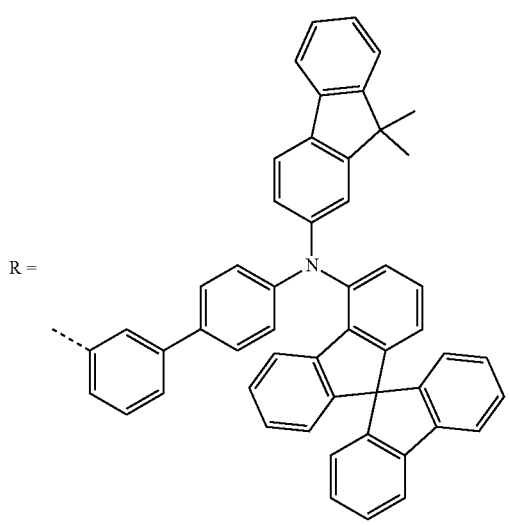
Formula 41
R = 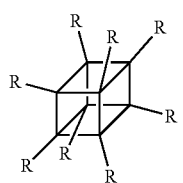
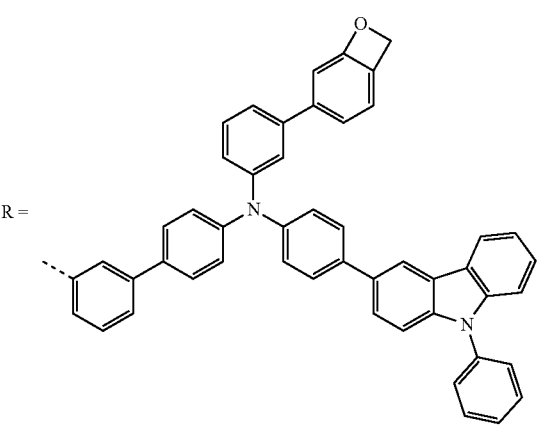
Formula 42
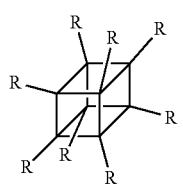

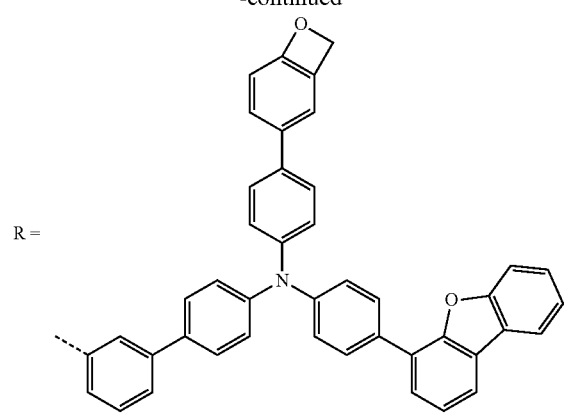
R =
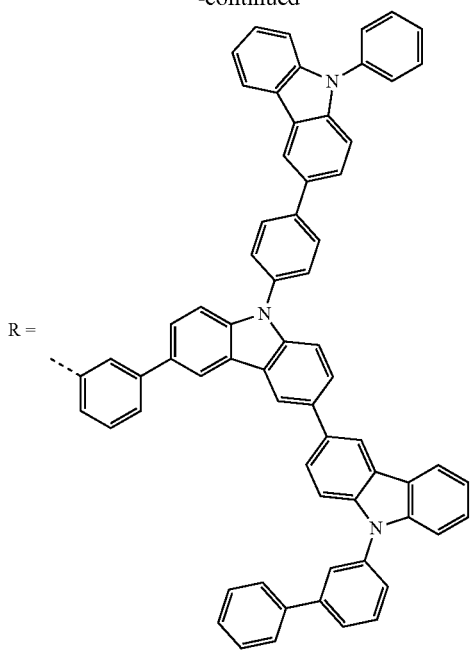
R =
Formula 43
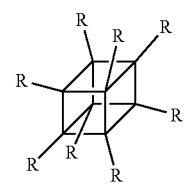
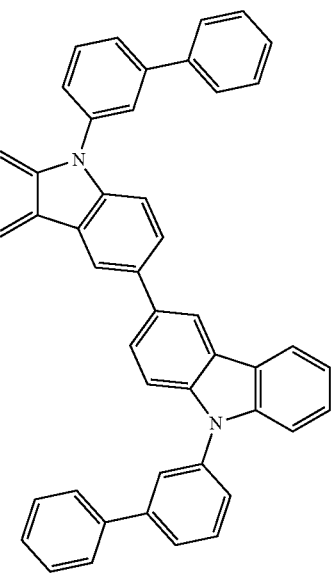
Formula 45
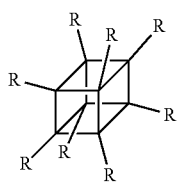
R =
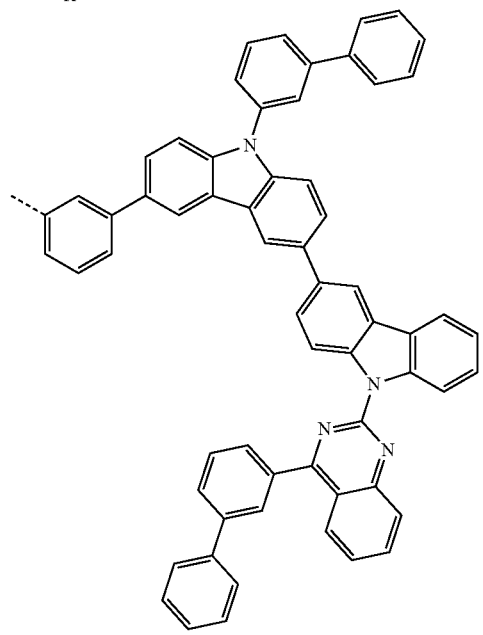
R =
Formula 44
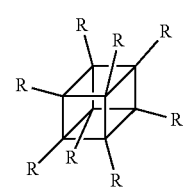
Formula 46

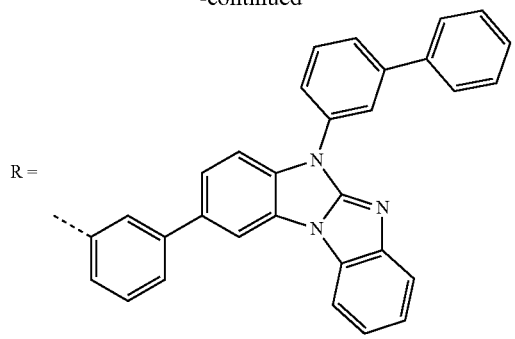
R =
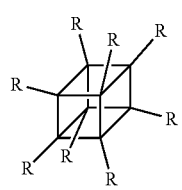
R =
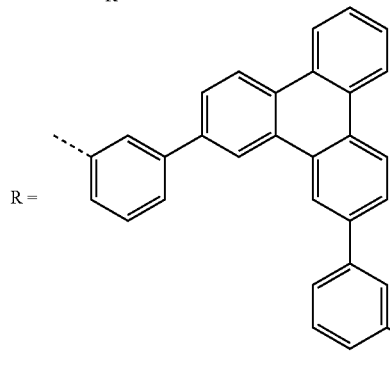
R =
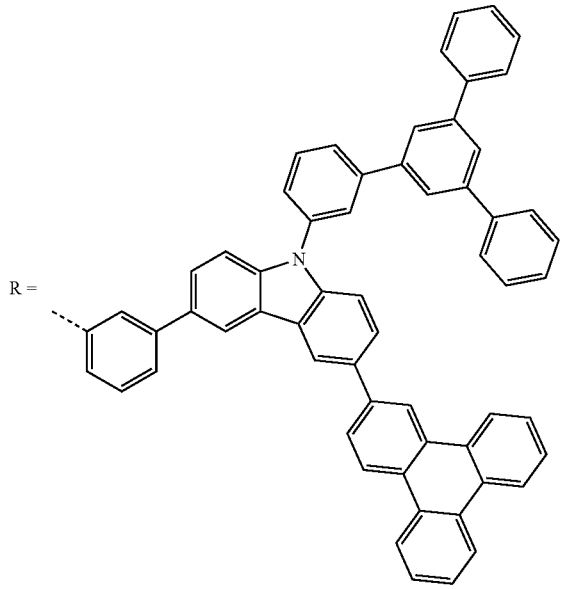
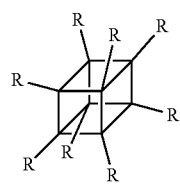
Formula 47
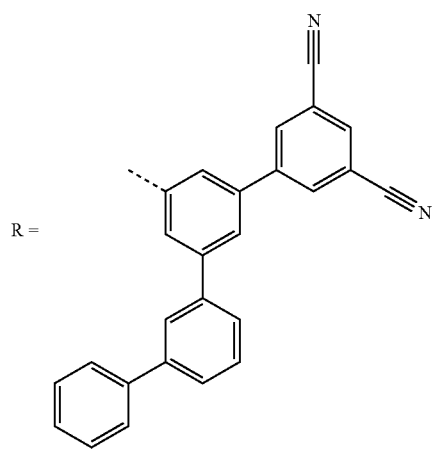
R =
Formula 48
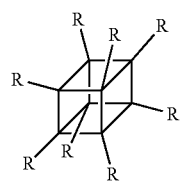
Formula 49
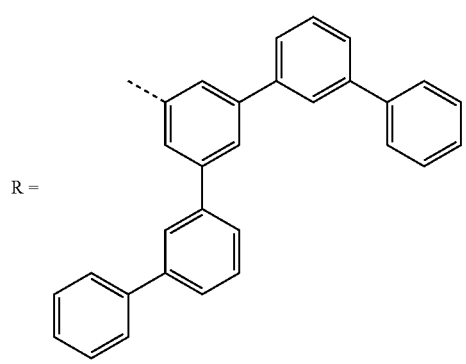
R =
Formula 50
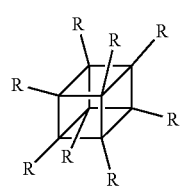
Formula 51

95
-continued
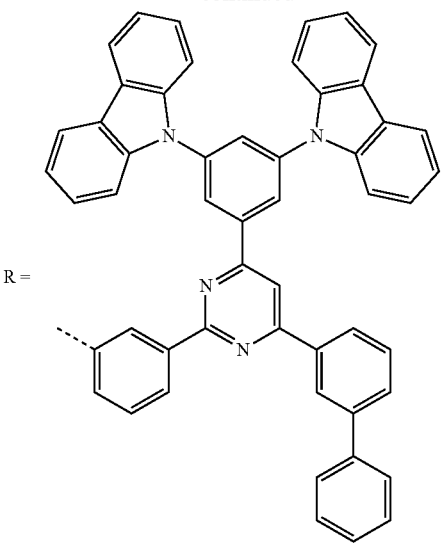
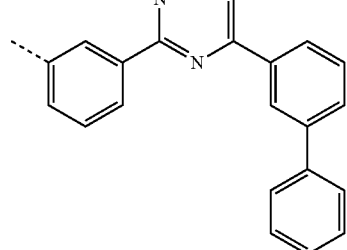
Formula 52
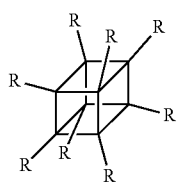
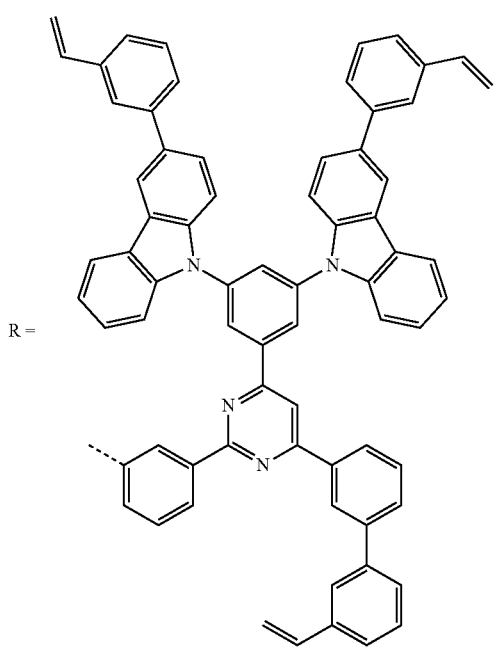
Formula 53
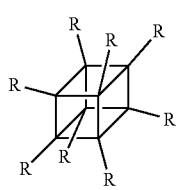
96
-continued
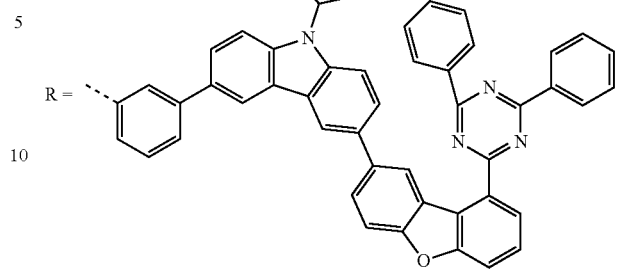
Formula 54
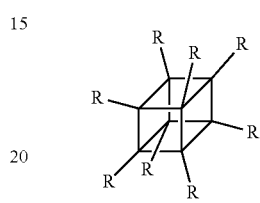
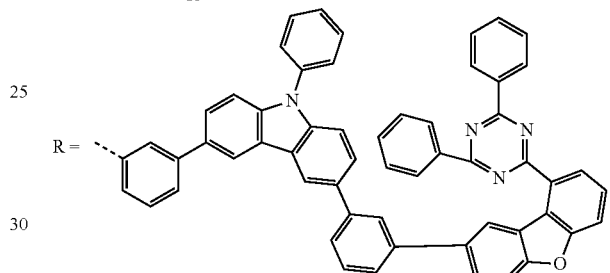
Formula 55
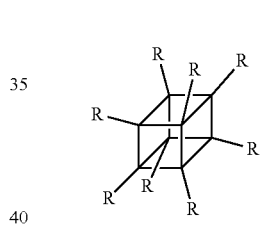
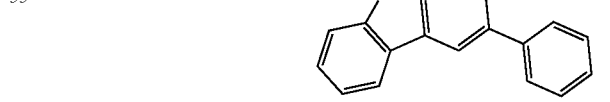
Formula 56
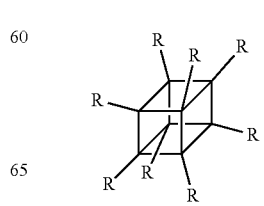

R = 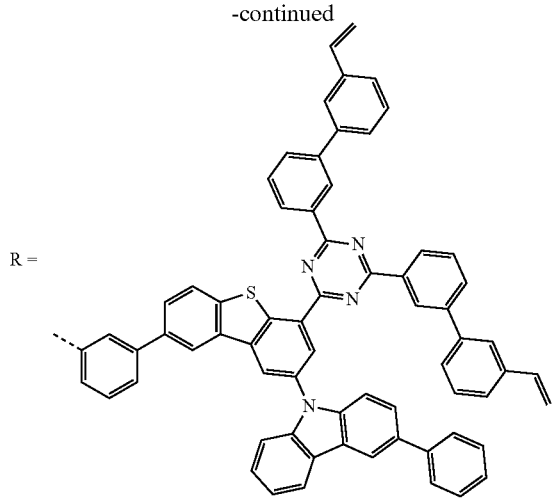

Preferred embodiments of compounds of the invention are recited specifically in the examples, these compounds being usable alone or in combination with further compounds for all purposes of the invention.

Provided that the conditions specified in claim 1 are met, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing the compounds of the invention, preferably compounds comprising structures of the formulae (I), (II), (IIIa), (IIIb), (IIIc), (IVa), (IVb), (IVc) and/or (V), in which, in a coupling reaction, a compound comprising at least one nonaromatic or nonheteroaromatic polycyclic ring system having a cubane structure is joined to a compound comprising at least one aromatic or heteroaromatic group.

Suitable compounds comprising at least one nonaromatic or nonheteroaromatic polycyclic ring system having a cubane structure are in many cases commercially available, with the starting compounds detailed in the examples being obtainable by known processes, and so reference is made thereto.

These compounds can be reacted with further compounds comprising at least one aromatic or heteroaromatic group by known coupling reactions, the necessary conditions for this purpose being known to the person skilled in the art, and detailed specifications in the examples assisting the person skilled in the art in conducting these reactions.

Particularly suitable and preferred coupling reactions which all lead to C—C bond formations and/or C—N bond formations are those according to BUCHWALD, SUZUKI, YAMAMOTO, STILLE, HECK, NEGISHI, SONOGASHIRA and HIYAMA. These reactions are widely known, and the examples will provide the person skilled in the art with further pointers.

In all the synthesis schemes which follow, the compounds are shown with a small number of substituents to simplify the structures. This does not rule out the presence of any desired further substituents in the processes.

The principles of the preparation processes detailed above are known in principle from the literature for similar compounds and can be adapted easily by the person skilled in the art for the preparation of the compounds of the invention. Further information can be found in the examples.

It is possible by these processes, if necessary followed by purification, for example recrystallization or sublimation, to obtain the compounds of the invention comprising structures of formula (I) in high purity, preferably more than 99% (determined by means of $^1$H NMR and/or HPLC).

The compounds of the invention may also have suitable substituents, for example by relatively long alkyl groups (about 4 to 20 carbon atoms), especially branched alkyl groups, or optionally substituted aryl groups, for example xylyl, mesityl or branched terphenyl or quaterphenyl groups, which bring about solubility in standard organic solvents, such that the compounds are soluble at room temperature in toluene or xylene, for example, in sufficient concentration to be able to process the compounds from solution. These soluble compounds are of particularly good suitability for processing from solution, for example by printing methods. In addition, it should be emphasized that the compounds of the invention comprising at least one structure of the formulae (I), (II), (IIIa), (IIIb), (IIIc), (IVa), (IVb), (IVc) and/or (V) already have enhanced solubility in these solvents.

In addition, the compounds of the present invention may contain one or more crosslinkable groups. "Crosslinkable group" means a functional group capable of reacting irreversibly. This forms a crosslinked material which is insoluble. The crosslinking can usually be promoted by means of heat or by means of UV radiation, microwave radiation, x-radiation or electron beams. In this case, there is little by-product formation in the crosslinking. In addition, the crosslinkable groups that may be present in the functional compounds crosslink very readily, such that relatively small amounts of energy are required for the crosslinking (for example <200° C. in the case of thermal crosslinking).

Examples of crosslinkable groups are units containing a double bond, a triple bond, a precursor capable of in situ formation of a double or triple bond, or a heterocyclic addition-polymerizable radical. Crosslinkable groups include vinyl, alkenyl, preferably ethenyl and propenyl, $C_{4-20}$-cycloalkenyl, azide, oxirane, oxetane, di(hydrocarbyl) amino, cyanate ester, hydroxyl, glycidyl ether, $C_{1-10}$-alkyl acrylate, $C_{1-10}$-alkyl methacrylate, alkenyloxy, preferably ethenyloxy, perfluoroalkenyloxy, preferably perfluoroethenyloxy, alkynyl, preferably ethynyl, maleimide, cyclobutylphenyl, tri($C_{1-4}$)-alkylsiloxy and tri($C_{1-4}$)-alkylsilyl. Particular preference is given to cyclobutylphenyl, vinyl and alkenyl.

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds and polymers of the invention may be used in the form of a crosslinked or uncrosslinked layer.

The invention therefore further provides oligomers, polymers or dendrimers containing one or more of the above-detailed structures of the formulae (I), (II), (IIIa), (IIIb), (IIIc), (IVa), (IVb), (IVc) and/or (V) or compounds of the invention, wherein one or more bonds in the compounds of the invention or in the structures of the formulae (I), (II), (IIIa), (IIIb), (IIIc), (IVa), (IVb), (IVc) and/or (V) to the polymer, oligomer or dendrimer are present. According to the linkage of the structures of the formulae (I), (II), (IIIa), (IIIb), (IIIc), (IVa), (IVb), (IVc) and/or (V) or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formulae (I), (II), (IIIa), (IIIb), (IIIc), (IVa), (IVb), (IVc) and/or (V) or the preferred embodiments recited above and hereinafter are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

In a particular configuration of the present invention, the cubane structure shown in formula (I) may be the core of an oligomer, polymer and/or dendrimer. According to the configuration, the R and/or $R^a$ radical may be part of an oligomeric, polymeric or dendrimeric structure. In the case of structures of the formulae (IIIa), (IIIb) and/or (IIIc), linear structural elements may be formed. Structures of the formulae (IVa), (IVb), (IVc) and/or (V) can give rise to branches which, depending on the configuration, can bring about crosslinking.

In a preferred configuration, the cubane structures have 8 substituents (preferably structures of the formula (V)), where the R and/or $R^a$ radicals may be the same or different and each R and/or $R^a$ radical itself may be an oligomeric/polymeric radical. By virtue of the cubane structure, up to 8 radicals are joined via the cubane core in close proximity, which can achieve unexpected improvements.

Additionally of particular interest are compounds of the invention which feature a high glass transition temperature. In this connection, in particular, compounds of the invention that are usable as active compound in an organic electronic device, preferably compounds comprising structures of the formulae (I), (II), (IIIa), (IIIb), (IIIc), (IVa), (IVb), (IVc) and/or (V), or the preferred embodiments recited above and hereinafter that have a glass transition temperature of at least 70° C., more preferably of at least 110° C., even more preferably of at least 125° C. and especially preferably of at least 150° C., determined to DIN 51005 (2005-08 version), are preferred.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound, for example a fluorescent dopant, a phosphorescent dopant or a compound that exhibits TADF (thermally activated delayed fluorescence), especially a phosphorescent dopant, and/or a further matrix material. This further compound may also be polymeric.

The present invention therefore still further provides a composition comprising a compound of the invention and at least one further organically functional material. Functional materials are generally the organic or inorganic materials introduced between the anode and cathode. Preferably, the organically functional material is selected from the group consisting of fluorescent emitters, phosphorescent emitters, emitters that exhibit TADF (thermally activated delayed fluorescence), host materials, electron transport materials, electron injection materials, hole conductor materials, hole injection materials, electron blocker materials, hole blocker materials, wide bandgap materials and n-dopants.

The present invention therefore also relates to a composition comprising at least one compound of the invention, preferably a compound comprising structures of formulae (I), (II), (IIIa), (IIIb), (IIIc), (IVa), (IVb), (IVc) and/or (V) or the preferred embodiments recited above and hereinafter, and at least one further matrix material. According to a particular aspect of the present invention, the further matrix material has hole-transporting properties.

The present further provides a composition comprising at least one compound of the invention, preferably a compound comprising at least one structure of formulae (I), (II), (IIIa), (IIIb), (IIIc), (IVa), (IVb), (IVc) and/or (V) or the preferred embodiments recited above and hereinafter, and at least one wide bandgap material, a wide bandgap material being understood to mean a material in the sense of the disclosure of U.S. Pat. No. 7,294,849. These systems exhibit exceptional advantageous performance data in electroluminescent devices.

Preferably, the additional compound may have a band gap of 2.5 eV or more, preferably 3.0 eV or more, very preferably of 3.5 eV or more. One way of calculating the band gap is via the energy levels of the highest occupied molecular orbital (HOMO) and the lowest unoccupied molecular orbital (LUMO).

Molecular orbitals, especially also the highest occupied molecular orbital (HOMO) and the lowest unoccupied molecular orbital (LUMO), the energy levels thereof and the energy of the lowest triplet state $T_1$ and that of the lowest excited singlet state $S_1$ of the materials are determined via quantum-chemical calculations. For calculation of organic substances without metals, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SCF/DFT/Default Spin/B3PW91" method with the "6-31 G(d)" basis set (charge 0, spin singlet). For metal-containing compounds, the geometry is optimized via the "Ground State/Hartree-Fock/Default Spin/LanL2 MB/Charge 0/Spin Singlet" method. The energy calculation is effected analogously to the above-described method for the organic substances, except that the "LanL2DZ" basis set is used for the metal atom and the "6-31G(d)" basis set for the ligands. The HOMO energy level HEh or LUMO energy level LEh is obtained from the energy calculation in Hartree units. This is used to determine the HOMO and LUMO energy levels in electron volts, calibrated by cyclic voltammetry measurements, as follows:

HOMO(eV)=((HEh*27.212)−0.9899)/1.1206

LUMO(eV)=((LEh*27.212)−2.0041)/1.385

These values are to be regarded as HOMO and LUMO energy levels of the materials in the context of this application.

The lowest triplet state $T_1$ is defined as the energy of the triplet state having the lowest energy, which is apparent from the quantum-chemical calculation described.

The lowest excited singlet state $S_1$ is defined as the energy of the excited singlet state having the lowest energy, which is apparent from the quantum-chemical calculation described.

The method described herein is independent of the software package used and always gives the same results. Examples of frequently utilized programs for this purpose are "Gaussian09W" (Gaussian Inc.) and Q-Chem 4.1 (Q-Chem, Inc.).

The present invention also relates to a composition comprising at least one compound comprising structures of formulae (I), (II), (IIIa), (IIIb), (IIIc), (IVa), (IVb), (IVc) and/or (V) or the preferred embodiments recited above and hereinafter and at least one phosphorescent emitter, the term "phosphorescent emitter" also being understood to mean phosphorescent dopants.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

Preferred phosphorescent dopants for use in matrix systems, preferably mixed matrix systems, are the preferred phosphorescent dopants specified hereinafter.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum. In the context of the present invention, all luminescent compounds containing the abovementioned metals are regarded as phosphorescent compounds.

Examples of the emitters described above can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2016124304, WO 2017032439, WO 2018019687, WO 2018019688, WO 2018041769, WO 2018054798, WO 2018069196, WO 2018069197, WO 2018069273. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Explicit examples of phosphorescent dopants are adduced in the following table:

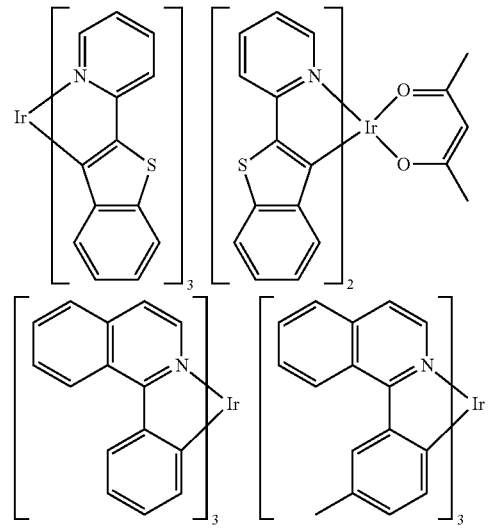

-continued
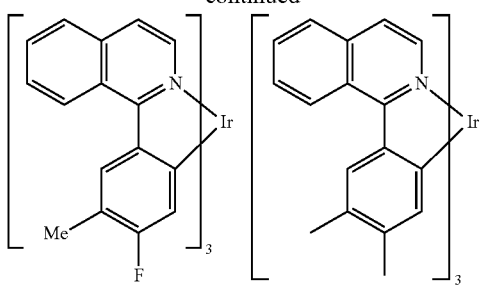
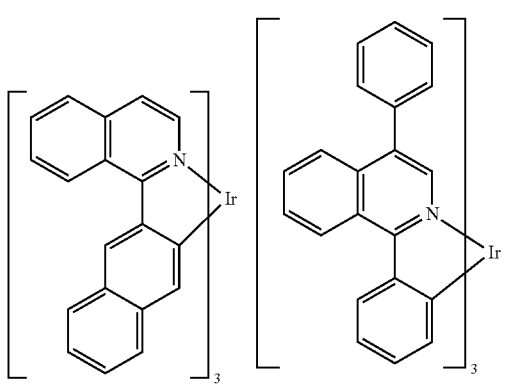
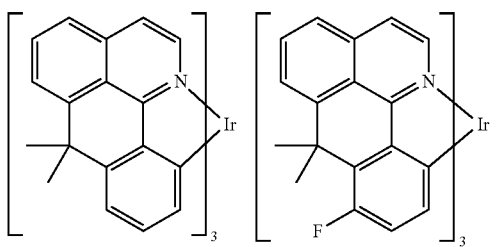
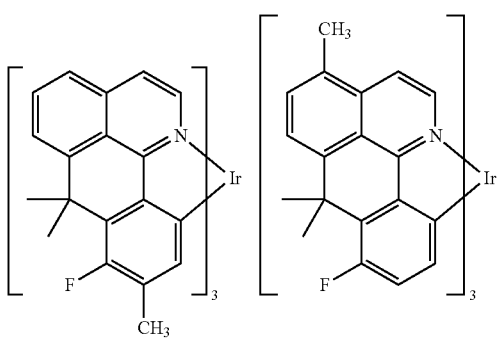
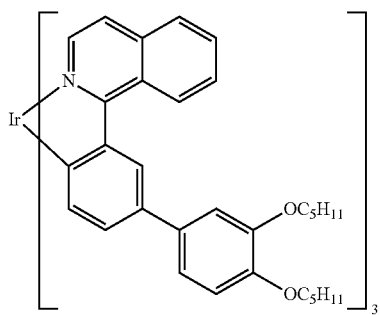
-continued
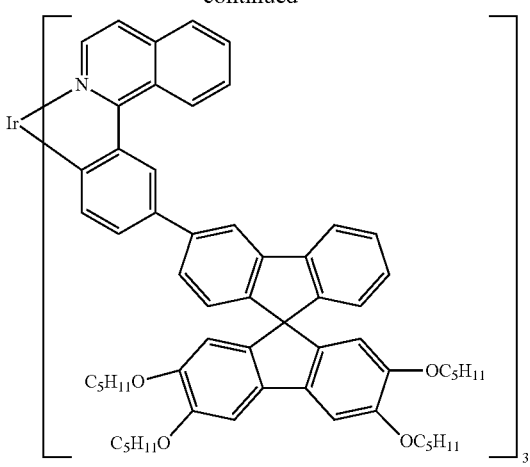
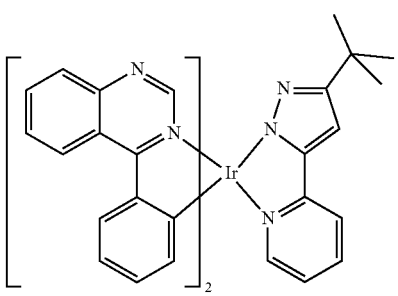
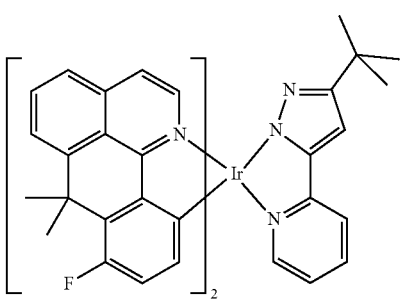
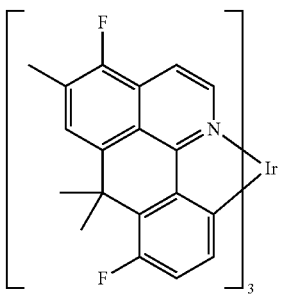
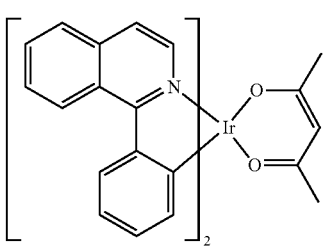

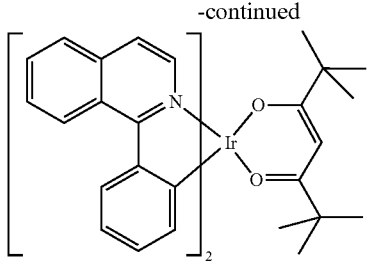
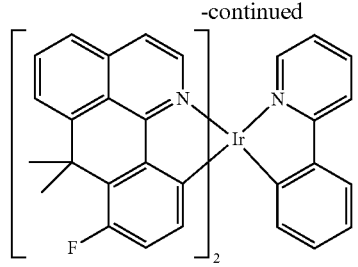
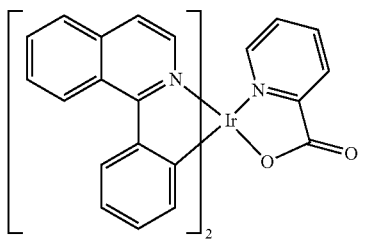
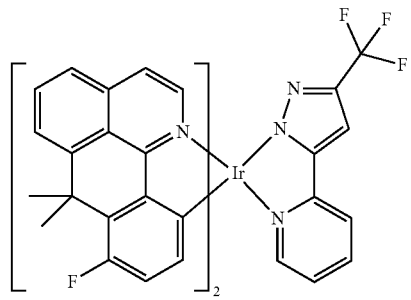
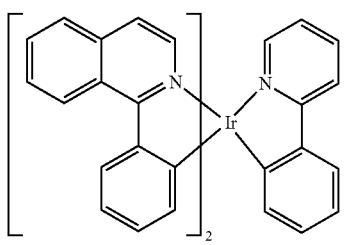
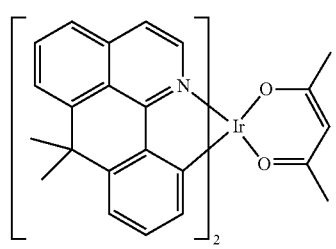
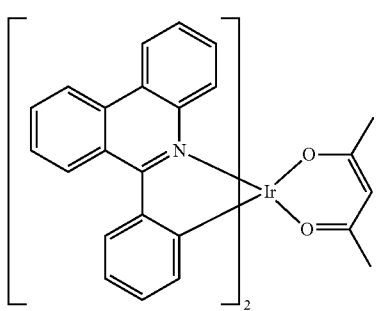
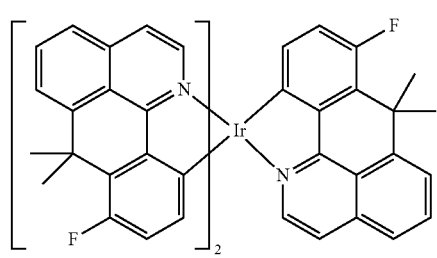
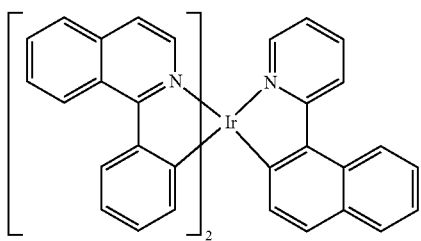
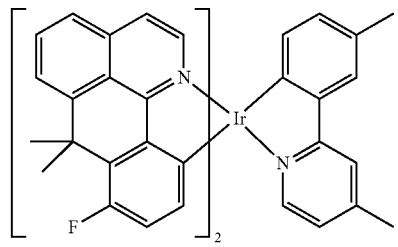
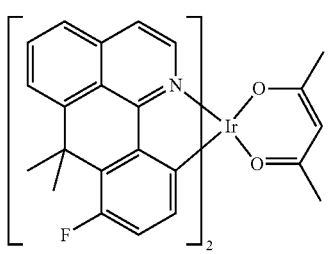
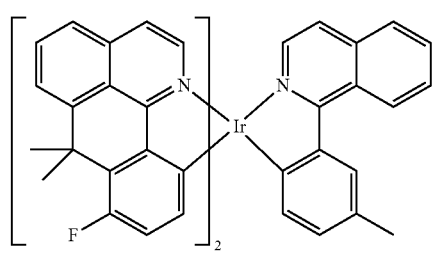

107
-continued
108
-continued
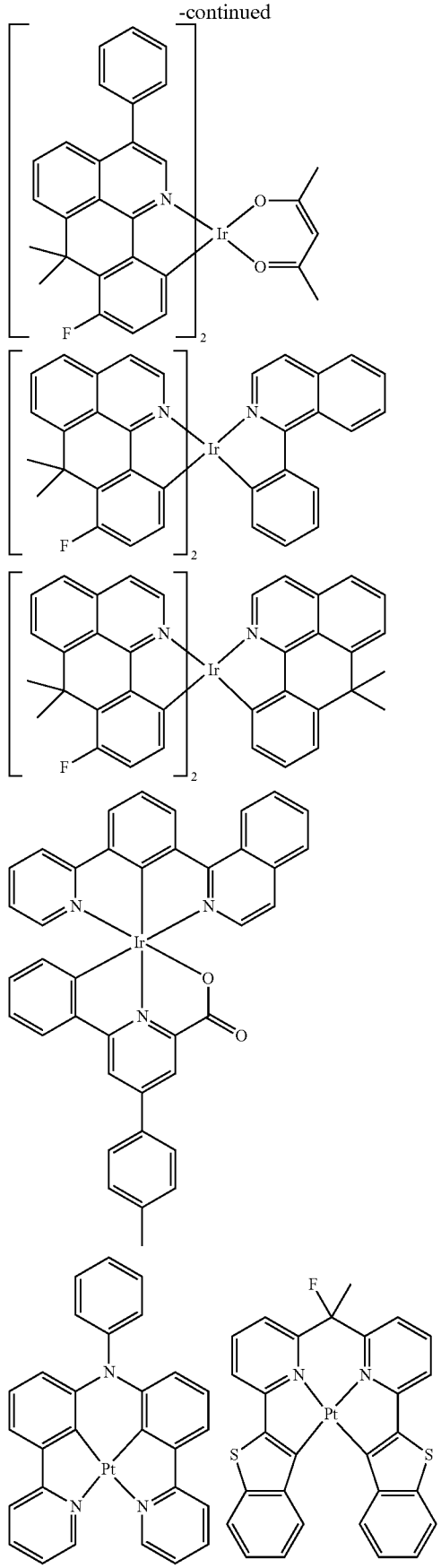
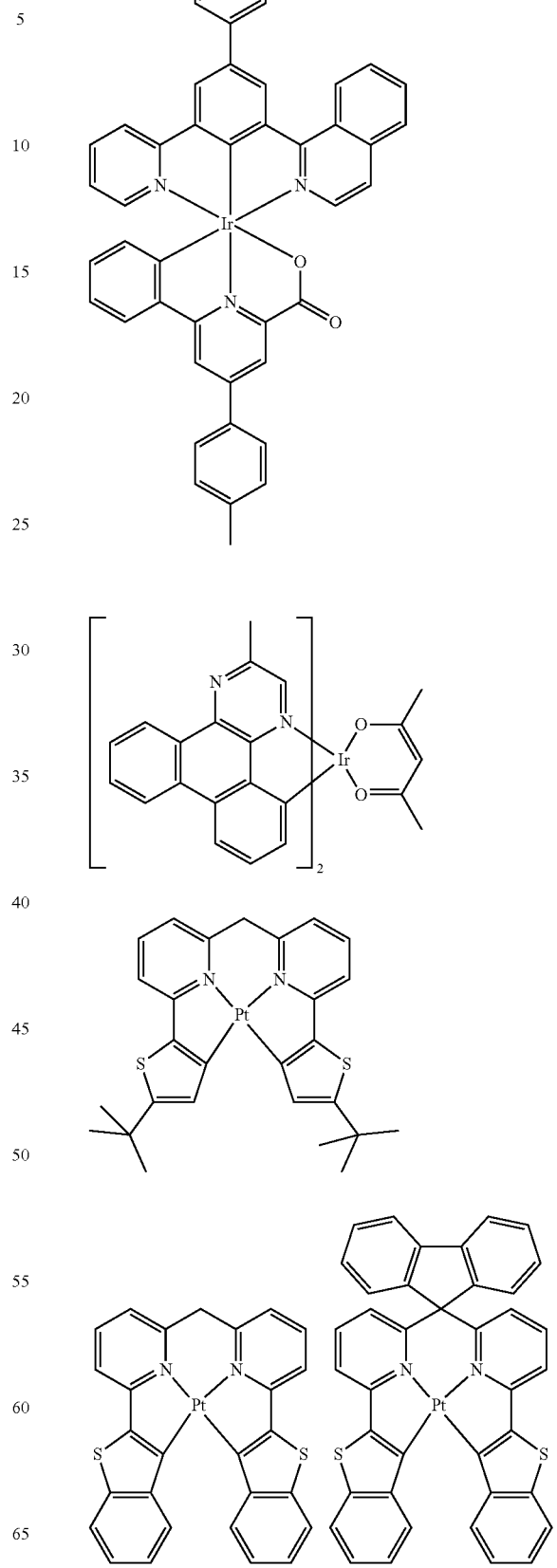

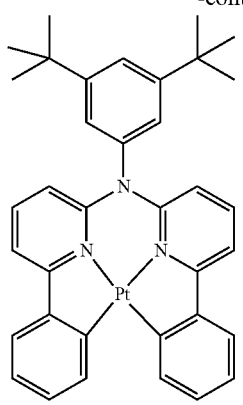
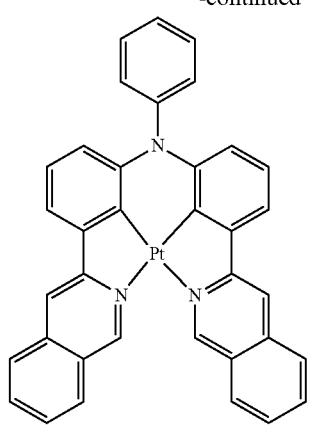
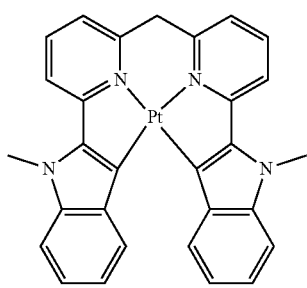
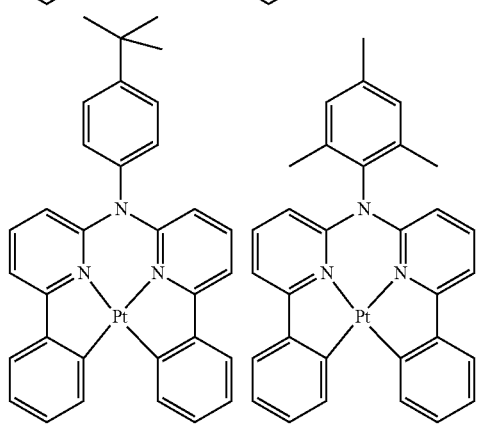
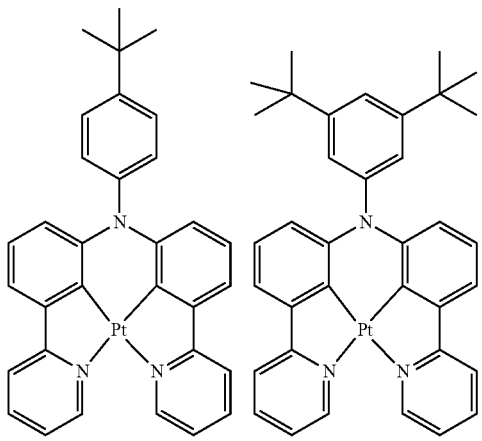
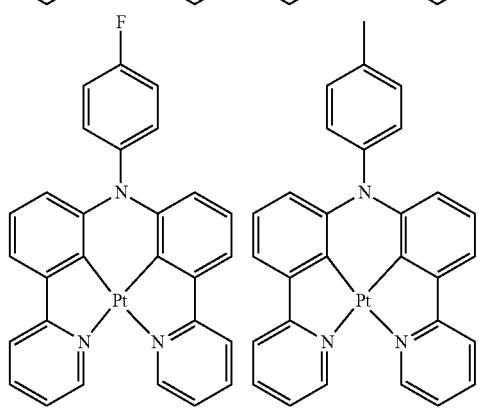
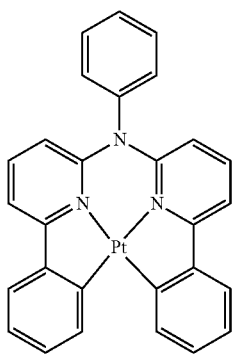
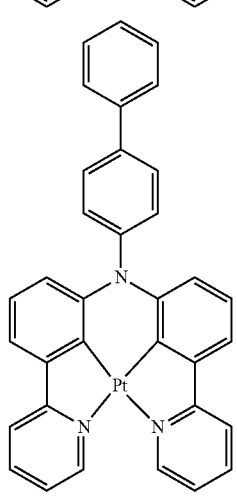

111
-continued
112
-continued
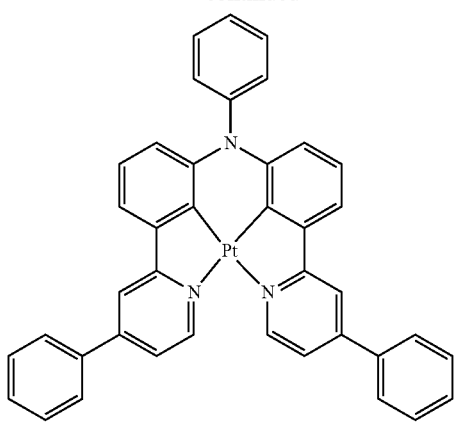
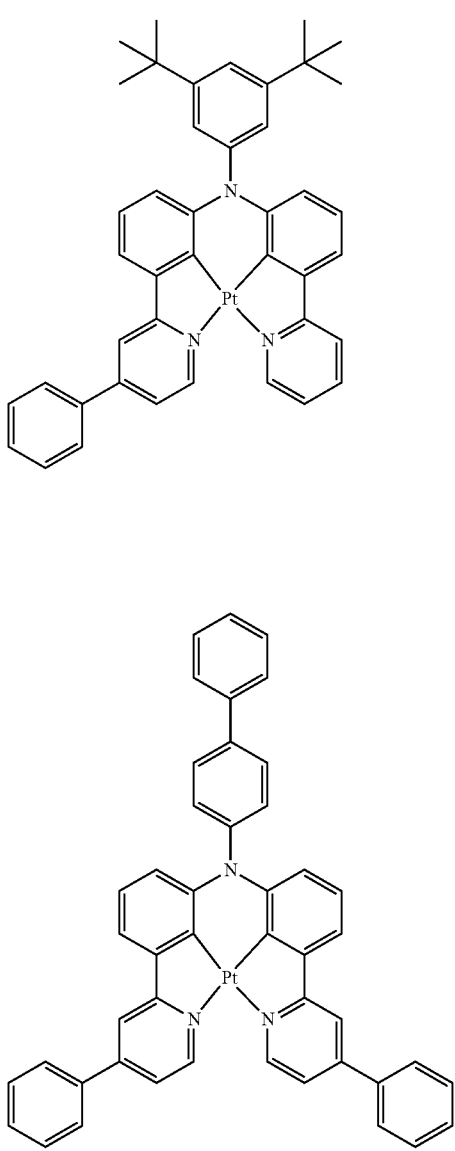

-continued
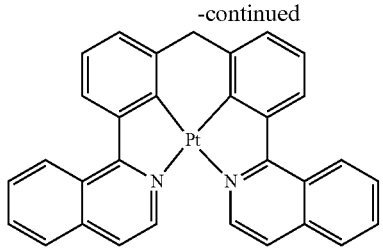
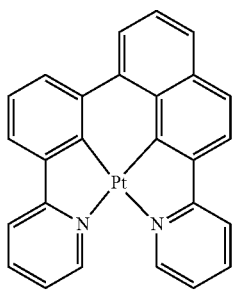
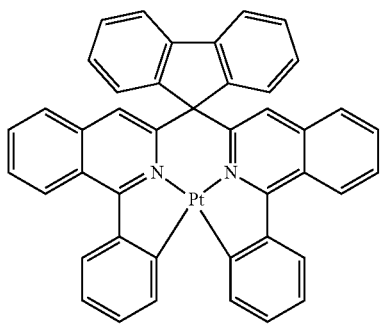
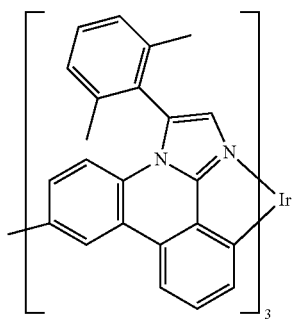
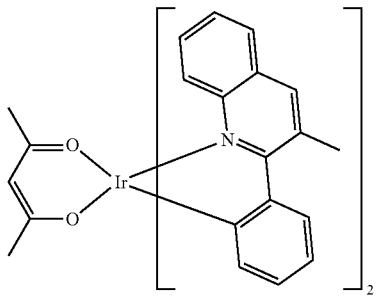
-continued
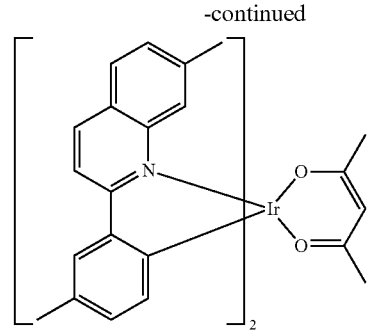
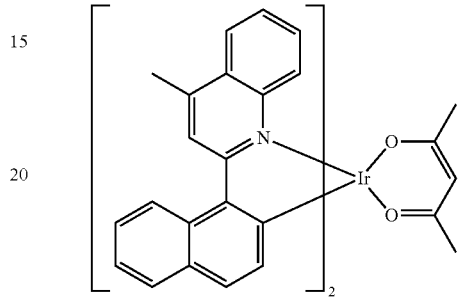
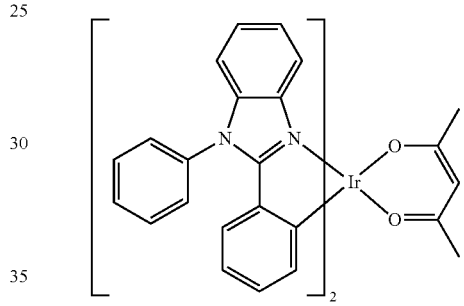
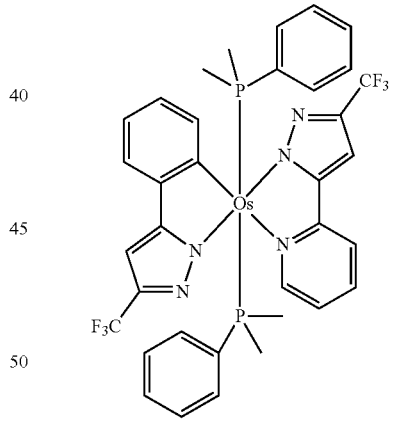
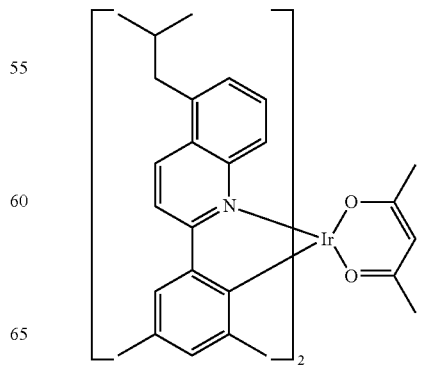

115
-continued
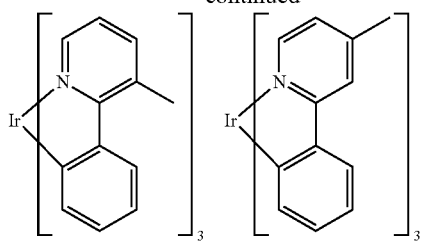
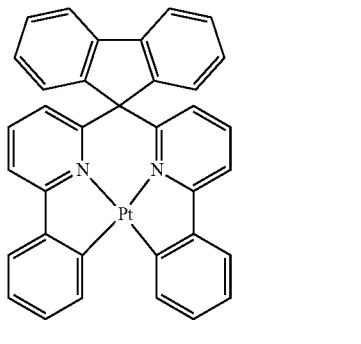
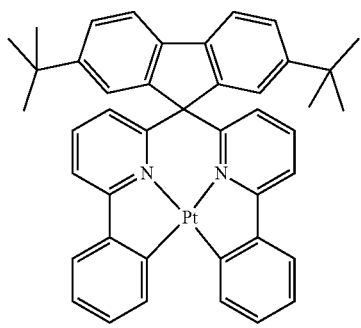
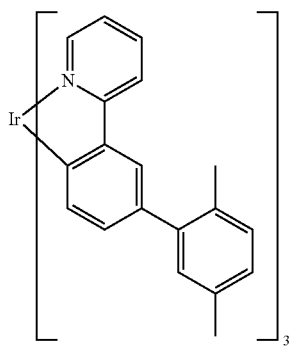
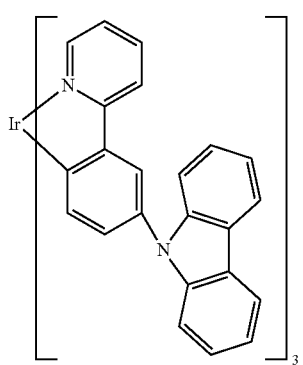
116
-continued
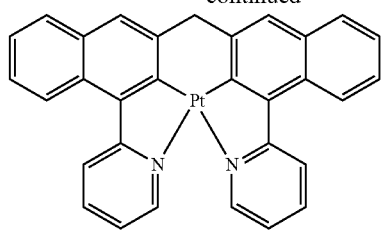
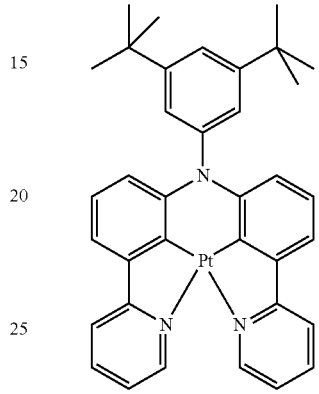
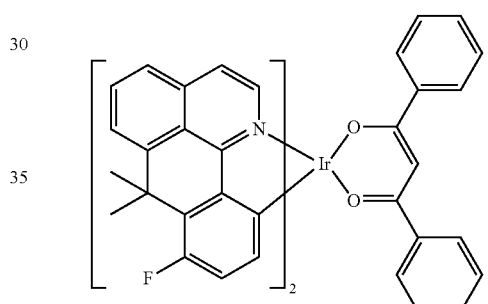
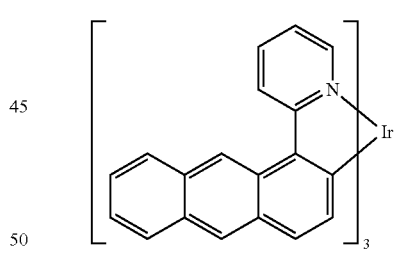
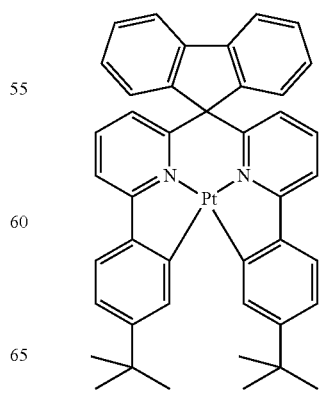

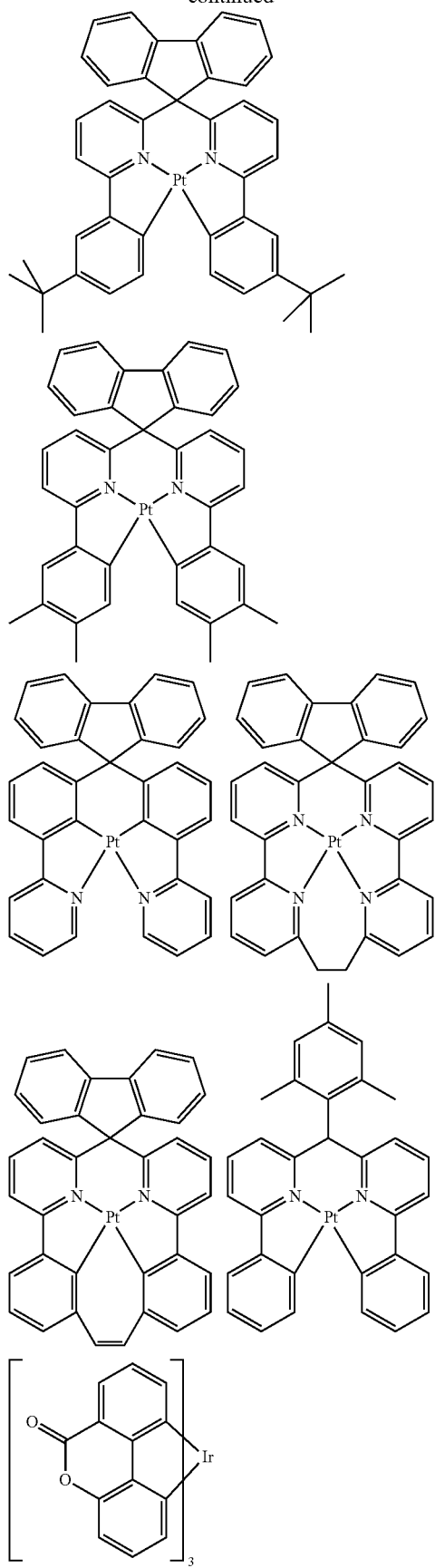
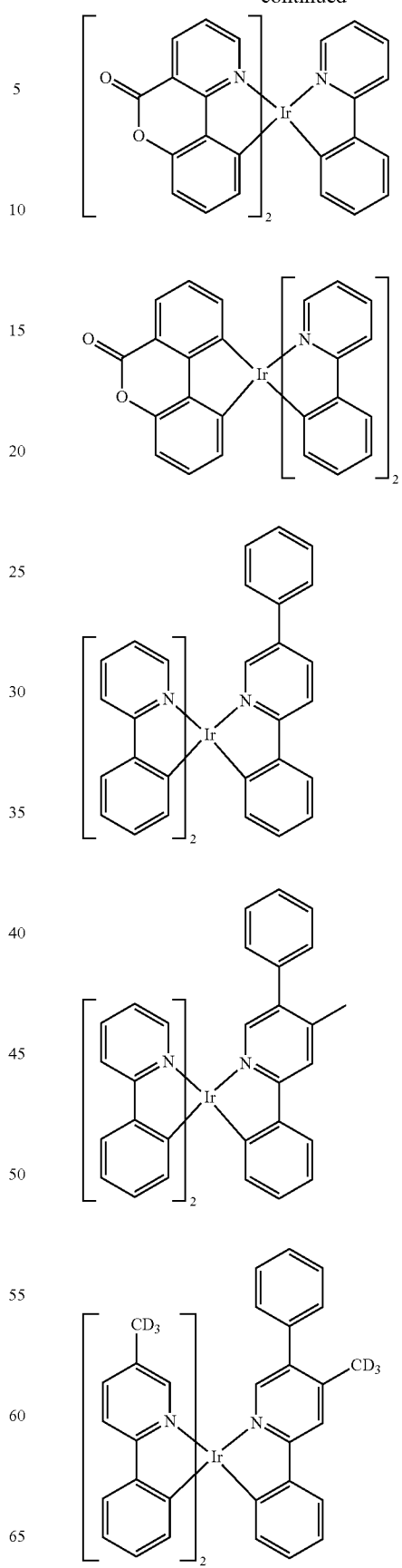

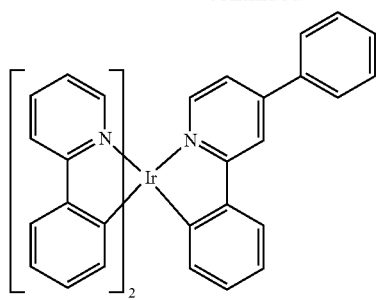
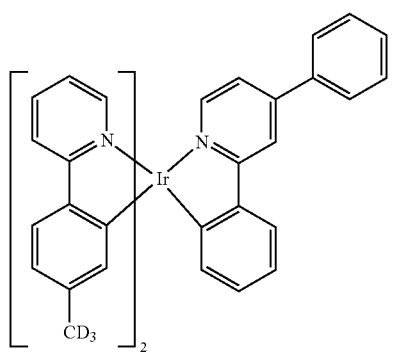
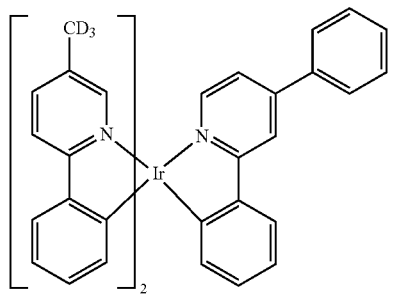
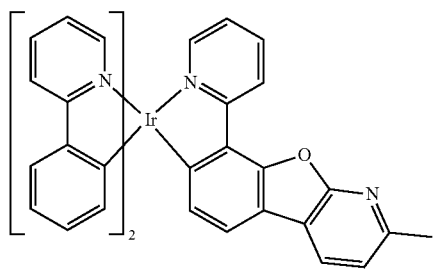
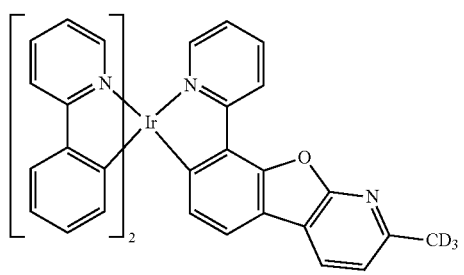
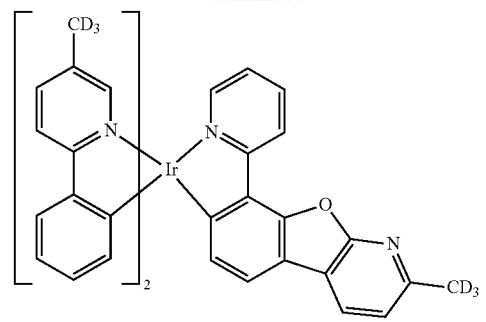
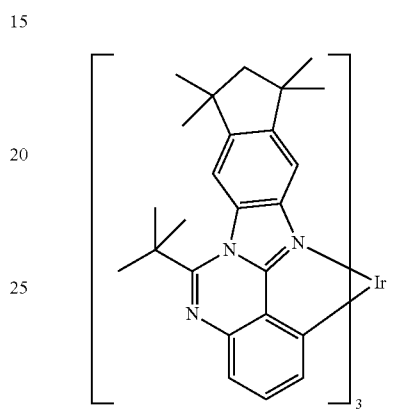
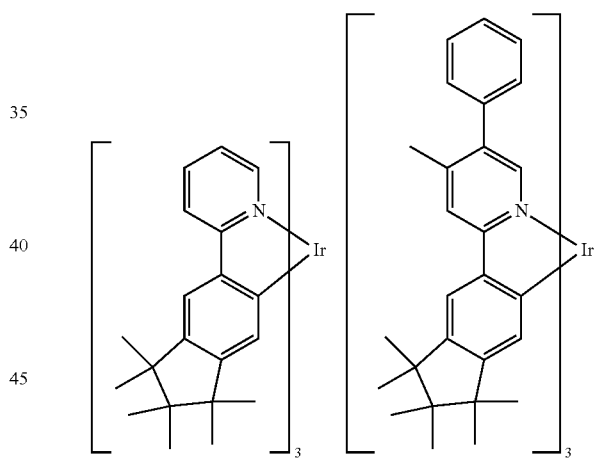
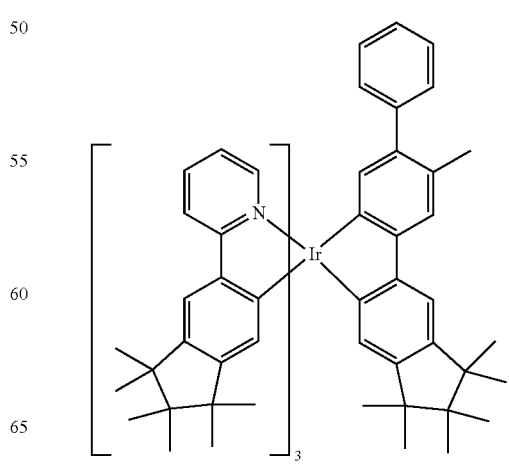

121
-continued
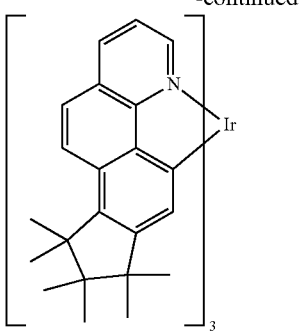
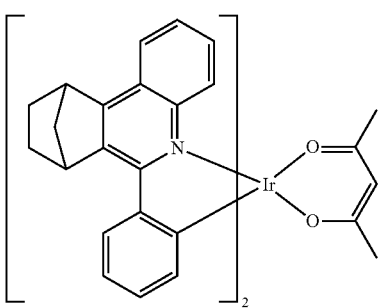
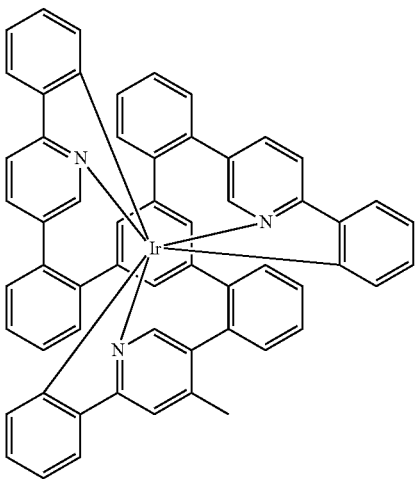
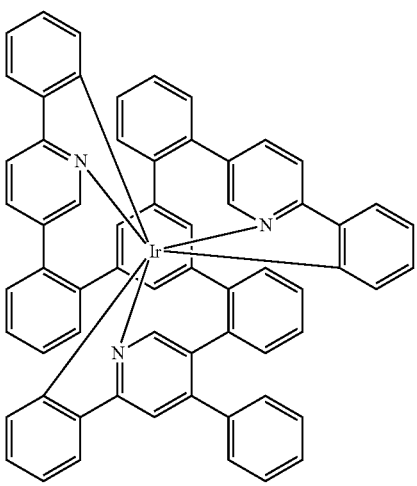
122
-continued
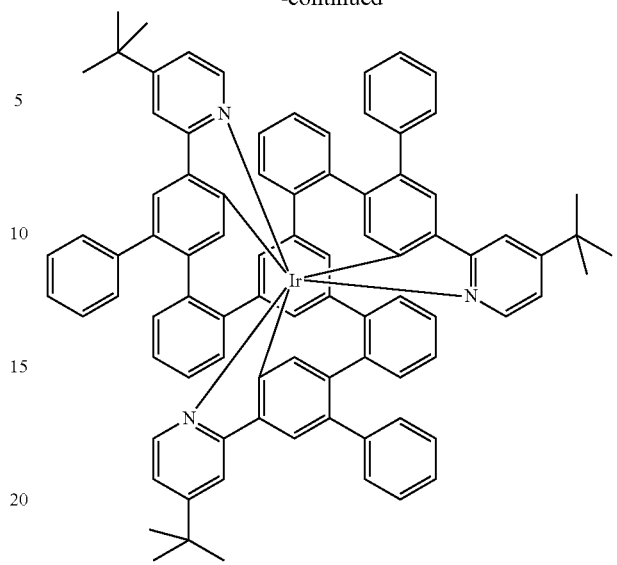
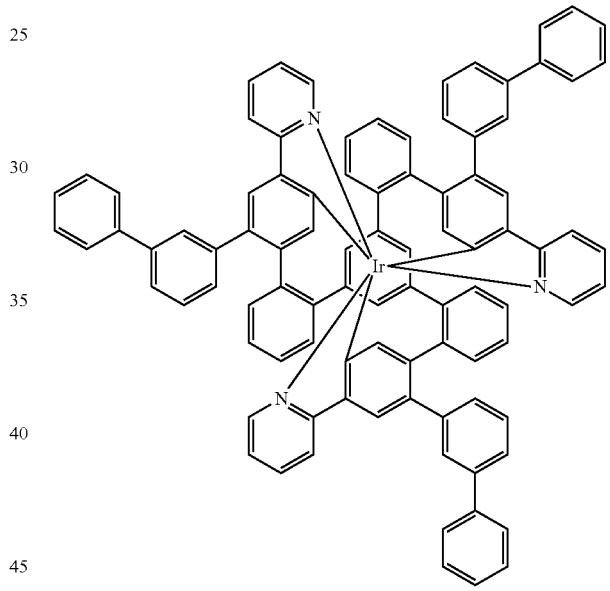
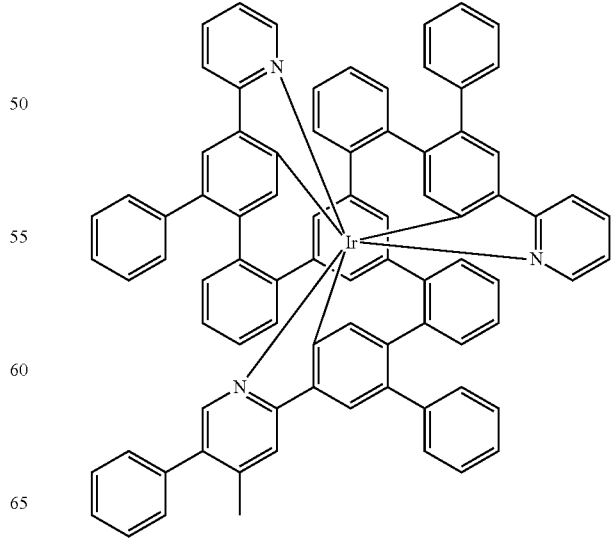

-continued

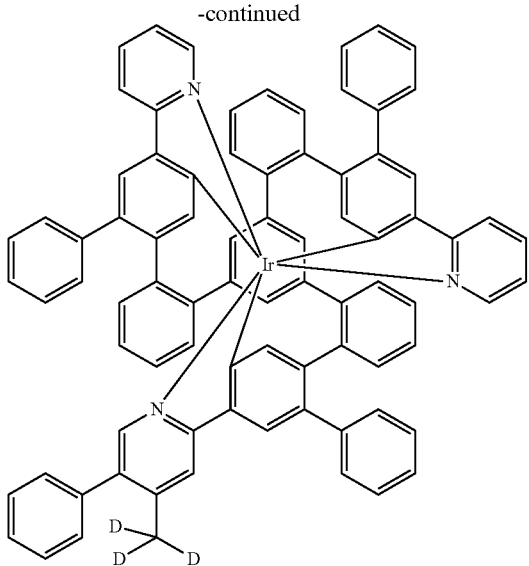

The above-described compounds comprising structures of the formulae (I), (II), (IIIa), (IIIb), (IIIc), (IVa), (IVb), (IVc) and/or (V) or the above-detailed preferred embodiments can preferably be used as active component in an electronic device. An electronic device is understood to mean any device comprising anode, cathode and at least one layer between anode and cathode, said layer comprising at least one organic or organometallic compound. The electronic device of the invention thus comprises anode, cathode and at least one intervening layer containing at least one compound comprising structures of the formula (I). Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), organic laser diodes (O-lasers) and organic plasmon emitting devices (D. M. Koller et al., Nature Photonics 2008, 1-4), preferably organic electroluminescent devices (OLEDs, PLEDs), especially phosphorescent OLEDs, containing at least one compound comprising structures of the formula (I) in at least one layer. Particular preference is given to organic electroluminescent devices. Active components are generally the organic or inorganic materials introduced between the anode and cathode, for example charge injection, charge transport or charge blocker materials, but especially emission materials and matrix materials.

A preferred embodiment of the invention is organic electroluminescent devices. The organic electroluminescent device comprises cathode, anode and at least one emitting layer. Apart from these layers, it may comprise still further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as $MoO_3$ or $WO_3$ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. Preference is further given to tandem OLEDs as well. The system may also be a hybrid system wherein one or more layers fluoresce and one or more other layers phosphoresce.

In a preferred embodiment of the invention, the organic electroluminescent device contains the compound of the invention, preferably a compound comprising structures of formulae (I), (II), (IIIa), (IIIb), (IIIc), (IVa), (IVb), (IVc) and/or (V) or the above-detailed preferred embodiments as matrix material, preferably as electron-conducting matrix material, in one or more emitting layers, preferably in combination with a further matrix material, preferably a hole-conducting matrix material. In a further preferred embodiment of the invention, the further matrix material is an electron-transporting compound. In yet a further preferred embodiment, the further matrix material is a compound having a large band gap which is not involved to a significant degree, if at all, in the hole and electron transport in the layer. An emitting layer comprises at least one emitting compound.

In a further particularly preferred embodiment of the present invention, an organic electroluminescent device of the invention comprises the compound of the invention, preferably a compound comprising structures of formulae (I), (II), (IIIa), (IIIb), (IIIc), (IVa), (IVb), (IVc) and/or (V) or the above-detailed preferred embodiments in a hole conductor layer or an electron conductor layer.

Suitable matrix materials which can be used in combination with the compounds of formulae (I), (II), (IIIa), (IIIb), (IIIc), (IVa), (IVb), (IVc) and/or (V) or according to the preferred embodiments are aromatic ketones, aromatic phosphine oxides or aromatic sulfoxides or sulfones, for example according to WO 2004/013080, WO 2004/093207, WO 2006/005627 or WO 2010/006680, triarylamines, especially monoamines, for example according to WO 2014/015935, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109 and WO 2011/000455, azacarbazole derivatives, for example according to EP 1617710, EP 1617711, EP 1731584, JP 2005/347160, bipolar matrix materials, for example according to WO 2007/137725, silanes, for example according to WO 005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, lactams, for example according to WO 2011/116865, WO 2011/137951 or WO 2013/064206, 4-spirocarbazole derivatives, for example according to WO 2014/094963 or WO 2015/192939, or dibenzofuran derivatives, for example according to WO 2015/169412, WO 2016/015810, WO 2016/023608 or the as yet unpublished applications EP16158460.2 and EP16159829.7. It is likewise possible for a further phosphorescent emitter which emits at a shorter wavelength than the actual emitter to be present as co-host in the mixture.

Preferred co-host materials are triarylamine derivatives, especially monoamines, indenocarbazole derivatives, 4-spirocarbazole derivatives, lactams and carbazole derivatives.

It may also be preferable to use a plurality of different matrix materials as a mixture, especially at least one electron-conducting matrix material and at least one hole-conducting matrix material. Preference is likewise given to the use of a mixture of a charge-transporting matrix material and an electrically inert matrix material having no significant involvement, if any, in the charge transport, as described, for example, in WO 2010/108579.

It is further preferable to use a mixture of two or more triplet emitters together with a matrix. In this case, the triplet emitter having the shorter-wave emission spectrum serves as co-matrix for the triplet emitter having the longer-wave emission spectrum.

More preferably, a compound of the invention comprising structures of formulae (I), (II), (IIIa), (IIIb), (IIIc), (IVa), (IVb), (IVc) and/or (V), in a preferred embodiment, can be used as matrix material in an emission layer of an organic electronic device, especially in an organic electroluminescent device, for example in an OLED or OLEC. In this case, the matrix material containing compound comprising structures of formulae (I), (II), (IIIa), (IIIb), (IIIc), (IVa), (IVb), (IVc) and/or (V) or the preferred embodiments recited above and hereinafter is present in the electronic device in combination with one or more dopants, preferably phosphorescent dopants.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compounds comprising structures of formulae (I), (II), (IIIa), (IIIb), (IIIc), (IVa), (IVb), (IVc) and/or (V) or the preferred embodiments recited above and hereinafter are used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfil(s) other functions. The two different matrix materials may be present here in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The present invention further provides an electronic device, preferably an organic electroluminescent device, comprising one or more compounds of the invention and/or at least one oligomer, polymer or dendrimer of the invention in one or more electron-conducting layers, as electron-conducting compound.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (O-SC) or the emission of light (OLED/PLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled.

Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an electronic device, especially an organic electroluminescent device, which is characterized in that one or more layers are coated by a sublimation process. In this case, the materials are applied by vapor deposition in vacuum sublimation systems at an initial pressure of typically less than $10^{-5}$ mbar, preferably less than $10^{-6}$ mbar. It is also possible that the initial pressure is even lower or even higher, for example less than $10^{-7}$ mbar.

Preference is likewise given to an electronic device, especially an organic electroluminescent device, which is characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example M. S. Arnold et al., *Appl. Phys. Lett.* 2008, 92, 053301).

Preference is additionally given to an electronic device, especially an organic electroluminescent device, which is characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The electronic device, especially the organic electroluminescent device, can also be produced as a hybrid system by applying one or more layers from solution and applying one or more other layers by vapor deposition. For example, it is possible to apply an emitting layer comprising a compound of the invention comprising structures of formulae (I), (II), (IIIa), (IIIb), (IIIc), (IVa), (IVb), (IVc) and/or (V) and a matrix material from solution, and to apply a hole blocker layer and/or an electron transport layer thereto by vapor deposition under reduced pressure.

These methods are known in general terms to those skilled in the art and can be applied by those skilled in the art without difficulty to electronic devices, especially organic electroluminescent devices comprising compounds of the invention comprising structures of formulae (I), (II), (IIIa), (IIIb), (IIIc), (IVa), (IVb), (IVc) and/or (V) or the above-detailed preferred embodiments.

The electronic devices of the invention, especially organic electroluminescent devices, are notable for one or more of the following surprising advantages over the prior art:

1. Electronic devices, especially organic electroluminescent devices, comprising compounds, oligomers, polymers or dendrimers of the invention usable as active compound in an organic electronic device or the preferred embodiments recited above and hereinafter, especially as electron-conducting materials and/or hole conductor materials or as matrix materials, have a very good lifetime.
2. Electronic devices, especially organic electroluminescent devices, comprising compounds, oligomers, polymers or dendrimers of the invention that are usable as active compound in an organic electronic device, or the preferred embodiments recited above and hereinafter, especially as electron transport materials, hole conductor materials and/or as host materials, have excellent efficiency. More particularly, efficiency is much higher compared to analogous compounds containing no cubane structure. The effect of the compounds, oligomers, polymers or dendrimers of the invention that are usable as active compound in an organic electronic device, or the preferred embodiments recited above and hereinafter, is a low operating voltage when used in electronic devices. In this context, these compounds especially bring about low roll-off, i.e. a small drop in power efficiency of the device at high luminances.
3. Electronic devices, especially organic electroluminescent devices, comprising compounds, oligomers, polymers or dendrimers usable as active compound in an organic electronic device, or the preferred embodiments recited above and hereinafter, as electron transport materials, hole conductor materials and/or as host materials, have excellent color purity.
4. The compounds, oligomers, polymers or dendrimers of the invention that are usable as active compound in an organic electronic device, or the preferred embodiments recited above and hereinafter, exhibit very high thermal and photochemical stability and lead to compounds having a very long lifetime.
5. With compounds, oligomers, polymers or dendrimers that are usable as active compound in an organic electronic device, or the preferred embodiments recited above and hereinafter, it is possible to avoid the formation of optical loss channels in electronic devices, especially organic electroluminescent devices. As a result, these devices feature a high PL efficiency and hence high EL efficiency of emitters, and excellent energy transmission of the matrices to dopants.
6. Compounds, oligomers, polymers or dendrimers that are usable as active compound in an organic electronic device, or the preferred embodiments recited above and hereinafter, have excellent glass film formation.
7. Compounds, oligomers, polymers or dendrimers that are usable as active compound in an organic electronic device, or the preferred embodiments recited above and hereinafter, form very good films from solutions.

These abovementioned advantages are not accompanied by a deterioration in the further electronic properties.

The compounds and mixtures of the invention are suitable for use in an electronic device. An electronic device is understood here to mean a device containing at least one layer containing at least one organic compound. The component may, however, also comprise inorganic materials or else layers formed entirely from inorganic materials.

The present invention therefore further provides for the use of the compounds or mixtures of the invention in an electronic device, especially in an organic electroluminescent device.

The present invention still further provides for the use of a compound of the invention and/or of an oligomer, polymer or dendrimer of the invention in an electronic device as fluorescent emitter, emitter that exhibits TADF (thermally activated delayed fluorescence), host material, electron transport material, electron injection material, hole conductor material, hole injection material, electron blocker material, hole blocker material and/or wide bandgap material, preferably as fluorescent emitter (singlet emitter), host material, hole conductor material and/or electron transport material.

The present invention still further provides an electronic device comprising at least one of the above-detailed compounds or mixtures of the invention. In this case, the preferences detailed above for the compound also apply to the electronic devices. More preferably, the electronic device is selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), organic laser diodes (O-lasers) and organic plasmon emitting devices (D. M. Koller et al., *Nature Photonics* 2008, 1-4), preferably organic electroluminescent devices (OLEDs, PLEDs), especially phosphorescent OLEDs.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In the further layers of the organic electroluminescent device of the invention, it is possible to use any materials as typically used according to the prior art. The person skilled in the art is therefore able, without exercising inventive skill, to use any of the materials known for organic electroluminescent devices in combination with the compounds of the invention that are usable as active compound in an organic electronic device, preferably compounds comprising structures of the formulae (I), (II), (IIIa), (IIIb), (IIIc), (IVa), (IVb), (IVc) and/or (V) or according to the preferred embodiments.

The compounds of the invention generally have very good properties on use in organic electroluminescent devices. Especially in the case of use of the compounds of the invention in organic electroluminescent devices, the lifetime is significantly better compared to similar compounds according to the prior art. At the same time, the further properties of the organic electroluminescent device, especially the efficiency and voltage, are likewise better or at least comparable.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, should themselves be regarded as inventive and not merely as some of the embodiments of the present invention. For these features, independent protection may be sought in addition to or as an alternative to any currently claimed invention.

The technical teaching disclosed with the present invention may be abstracted and combined with other examples.

The invention is illustrated in more detail by the examples which follow, without any intention of restricting it thereby.

The person skilled in the art will be able to use the details given, without exercising inventive skill, to produce further electronic devices of the invention and hence to execute the invention over the entire scope claimed.

EXAMPLES

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDR¹CH or ABCR. The respective figures in square brackets or the numbers quoted for individual compounds relate to the CAS numbers of the compounds known from the literature. In the case of compounds that can display multiple tautomeric forms, one tautomeric form is shown representatively.

Example M1

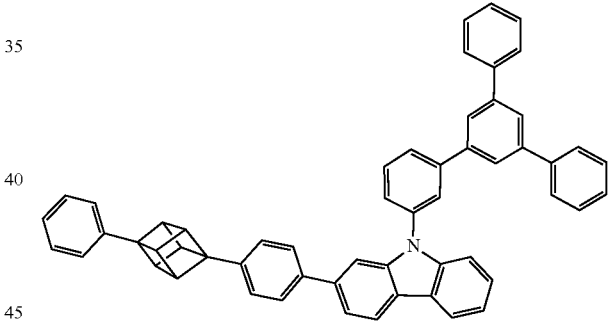

A well-stirred mixture of 3.8 g (10.0 mmol) of 1-[phenyl]-4-(phen-4-ylboronic acid pinacol ester)pentacyclo[4.2.0. $0^{2,5}.0^{3,8}.0^{4,7}$]octane [2179263-81-9], 6.1 g (11.0 mmol) of 3-bromo-9-(5'-phenyl[1,1':3,1''-terphenyl]-3-yl)-9H-carbazole [1846559-13-4], 4.2 g (30.0 mmol) of potassium carbonate, 231 mg (0.2 mmol) of tetrakis(triphenylphosphino)palladium(0), 60 ml of toluene, 30 ml of dioxane and 30 ml of water is heated under reflux for 16 h. After cooling, the organic phase is separated off and concentrated under reduced pressure. The remaining solids are dissolved in 100 ml of dichloromethane (DCM), and the solution is filtered through a silica gel bed in the form of a DCM slurry. 50 ml of ethanol is added to the filtrate and the filtrate is concentrated to about 30 ml, with crystallization of the product. The crystals are filtered off with suction, washed once with 30 ml of ethanol and then dried under reduced pressure. Purification is effected by five continuous hot extractions with toluene (cellulose extraction thimbles from Whatman), followed by heat treatment under high vacuum (p about $10^{-6}$ mbar, T<20000). Yield: 1.7 g (2.3 mmol), 23%; purity: >99.7%. ¹H NMR.

The following compounds can be prepared analogously:
| Ex. | Boronic ester Aryl/heteroaryl halide | Product | Yield |
|---|---|---|---|
| M2 | 2179263-81-9<br />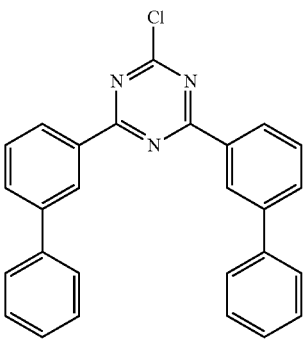<br />1205748-61-3 | 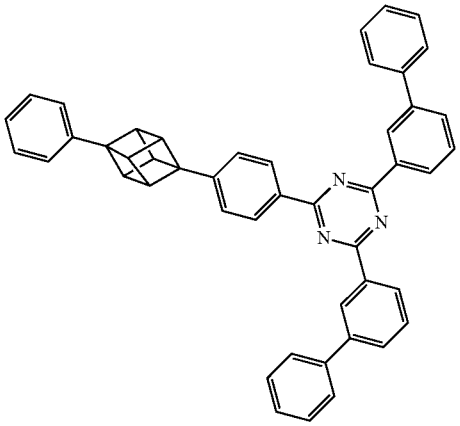 [SMILES: c1ccc(-c2cccc(-c3nc(-c4ccc(C56C7C8C5C5C6C7C85c5ccccc5)cc4)nc(-c4cccc(-c5ccccc5)c4)n3)c2)cc1] | 26% |
| M3 | 2179263-81-9<br />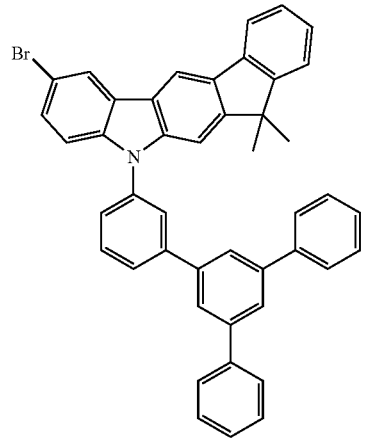 | 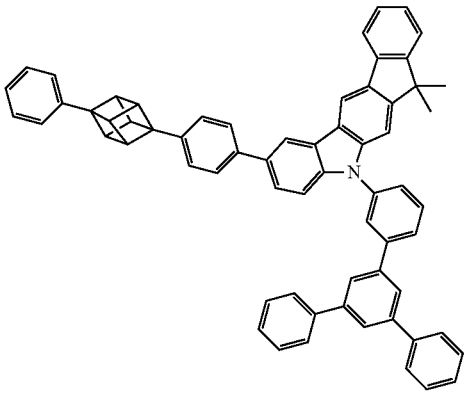 [SMILES: CC1(C)c2ccccc2-c2cc3c4cc(-c5ccc(C67C8C9C6C6C7C8C96c6ccccc6)cc5)ccc4n(-c4cccc(-c5cc(-c6ccccc6)cc(-c6ccccc6)c5)c4)c3cc21] | 19% |
| M4 | 2179263-81-9<br />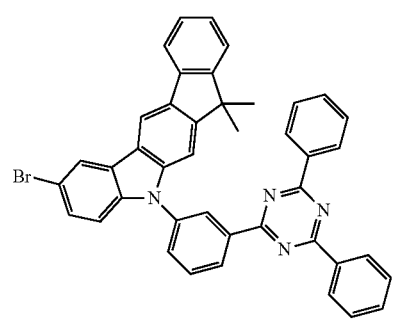<br />1613576-58-1 | 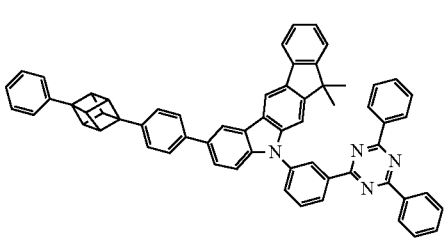 [SMILES: CC1(C)c2ccccc2-c2cc3c4cc(-c5ccc(C67C8C9C6C6C7C8C96c6ccccc6)cc5)ccc4n(-c4cccc(-c5nc(-c6ccccc6)nc(-c6ccccc6)n5)c4)c3cc21] | 21% |

Example D1

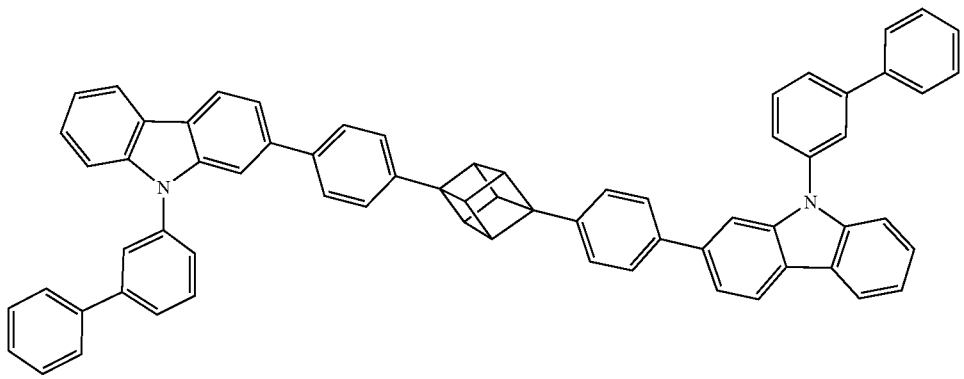 [SMILES: c1ccc(-c2cccc(-n3c4ccccc4c4ccc(-c5ccc(C67C8C9C6C6C7C8C96c6ccc(-c7ccc8c9ccccc9n(-c9cccc(-c%10ccccc%10)c9)c8c7)cc6)cc5)cc43)c2)cc1]

Procedure analogous to example M1, except that, 2.5 g (5.0 mmol) of 1,4-bis(phen-4-ylboronic acid pinacol ester)pentacyclo[4.2.0.0$^{2,5}$.0$^{3,8}$.0$^{4,7}$]octane [2179263-82-0] is used rather than 1-[phenyl]-4-(phen-4-ylboronic acid pinacol ester)pentacyclo[4.2.0.0$^{2,5}$.0$^{3,8}$.0$^{4,7}$]octane, and 4.4 g (11.0 mmol) of 9-[1,1'-biphenyl]-3-yl-3-bromo-9H-carbazole rather than 3-bromo-9-(5'-phenyl[1,1':3',1''-terphenyl]-3-yl)-9H-carbazole. Yield: 1.2 g (1.3 mmol), 26%; purity: >99.7%. $^1$H NMR.

The following compounds can be prepared analogously:

| Ex. | Reactants | Product | Yield |
|---|---|---|---|
| D2 | 2179263-82-0 <br> 1205748-61-3 |  | 24% |

Example: octa(4-chlorophenyl)cubane=O-4-ClPh-C

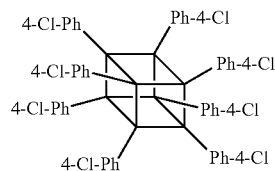

—Ph-4-Cl is: —⌬—Cl

Procedure analogous to P. M. Maitlis et al., Proceedings of the Chemical Society, 1962, 330.

To a well-degassed, stirred suspension, heated to 80° C., of 6.7 g (10.0 mmol) of dichloro[1,1',1'',1'''-(η$^4$-1,3-cyclobutadiene-1,2,3,4-tetrayl)tetrakis[4-chlorobenzene]]palladium(II) [12132-23-9] (calculated as monomer) in 200 ml of toluene is added dropwise a solution of 5.4 g (20.5 mmol) of triphenylphosphine over the course of 20 min. The mixture is stirred at 80° C. for a further 8 h, then allowed to cool, and the precipitated solids are filtered off. The solids are suspended in 100 ml of DCM and stirred at 30° C. for 1 h. The solids are filtered off again, and washed twice with 20 ml each time of DCM. The crude product thus obtained is recrystallized twice from 3-phenoxytoluene. Yield: 6.3 g (6.4 mmol), 64%; purity: about 97% by HPLC.

The filtrate is admixed with 50 ml of ethanol and concentrated gradually under reduced pressure until the bis(triphenylphosphino)palladium(II) chloride present therein crystallizes. It can be obtained by filtration and used subsequently as palladium source.

The following compound can be prepared analogously:

| Ex. | Reactant | Product | Yield |
|---|---|---|---|
| O-3-ClPh—C | dichloro[1,1',1'',1'''-(η⁴-1,3-cyclobutadiene-1,2,3,4-tetrayl)tetrakis[3-chlorobenzene]]palladium(II), prepared analogously to O-4-ClPh—C as per R. C. Cookson et al., J. Chem. Soc., 1881, 1965. | 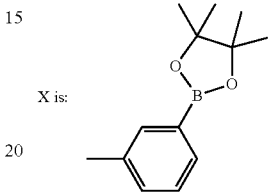 | 56% |

—Ph-3-Cl is: 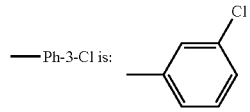

Example: octa(phen-4-ylboronic acid pinacol ester)cubane=O-4-BRSE-Ph-C

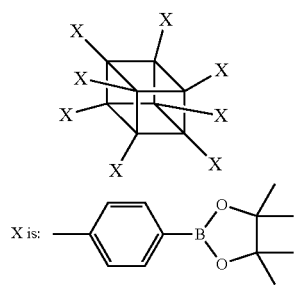

To a well-stirred suspension, heated to 60° C., of 4.9 g (5.0 mmol) of O-4-ClPh-C, 15.2 g (60 mmol) of bis(pinacolato)diborane [73183-34-3], 11.8 g (120 mmol) of anhydrous potassium acetate and 50 g of glass beads (diameter 3 mm) in 200 ml of THF is added a solution of 1232 mg (3 mmol) of S-Phos and 449 mg (2 mmol) palladium(II) acetate in 30 ml THF that has been heated to 60° C. while stirring for 10 min. The reaction mixture is stirred at 60° C. for 24 h. Then a further 5.1 g (20 mmol) of bis(pinacolato)diborane and ⅓ of the catalyst solution used above are added, and the mixture is heated for a further 16 h. After cooling, the THF is largely removed under reduced pressure, and the residue is taken up in 300 ml of hot methanol while stirring. After cooling, the crude product is filtered off with suction and washed three times with 50 ml each time of methanol. Further purification is effected by continuous hot extraction (cellulose extraction thimbles from Whatman), twice with DCM/methanol 2:1 and twice with DCM/acetonitrile 2:1. Yield: 5.0 g (2.9 mmol), 58%; purity: about 98% by HPLC.

The following compound can be prepared analogously:

| Ex. | Reactant | Product | Yield |
|---|---|---|---|
| O-3-BRSE-Ph—C | O-3-ClPh—C | 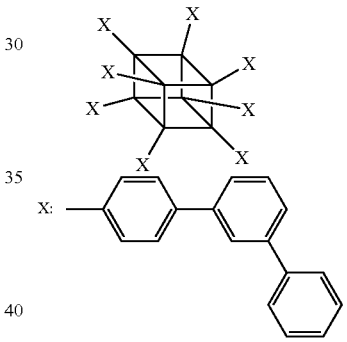 | 47% |

X is: (3-methylphenyl boronic acid pinacol ester structure)

Example O1

X is the functional radical shown in each case

A well-stirred mixture of 8.6 g (5 mmol) of O-4-BRSE-Ph-C, 14.0 g (60 mmol) of 3-bromo-1,1'-biphenyl [2113-57-7], 27.6 g (120 mmol) of tripotassium phosphate monohydrate, 1.15 g (1 mmol) of tetrakis(triphenylphosphino)palladium(0), 50 g of glass beads (diameter 3 mm) and 150 ml DMSO is heated to 120° C. for 24 h. After cooling to 60° C., the reaction mixture is poured into 300 ml of a water-methanol mixture (1:1, vv) and stirred for a further 30 min, and the crude product is filtered off with suction and washed three times with 30 ml each time of methanol. The crude product is dissolved in 200 ml of DCM, and the solution is filtered through a silica gel bed in the form of a DCM slurry. 50 ml of ethanol is added to the filtrate and the filtrate is concentrated to about 30 ml, with crystallization of the product. The crystals are filtered off with suction, washed once with 30 ml of ethanol and then dried under reduced pressure. Purification is effected by five continuous hot extractions with o-xylene (cellulose extraction thimbles from Whatman), followed by heat treatment under high vacuum (p about $10^{-6}$ mbar, T<300° C.). Yield: 3.5 g (1.8 mmol), 36%; purity: >99.7%. $^1$H NMR.

The following compounds can be prepared analogously:
| Ex. | Reactants | Product | Yield |
|---|---|---|---|
| O2 | O-3-BRSE-Ph—C 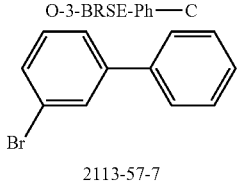 2113-57-7 | X: 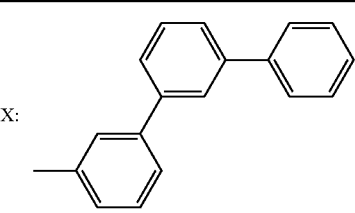 | 44% |
| O3 | O-4-BRSE-Ph—C 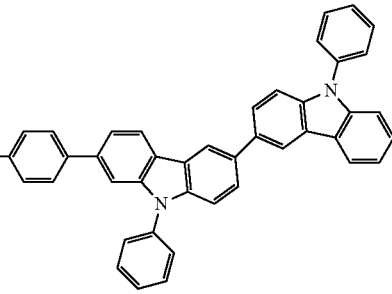 1702361-07-6 | X: 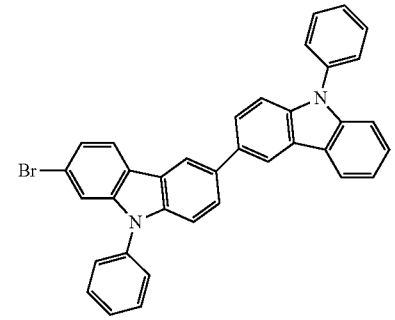 | 35% |
| O4 | O-3-BRSE-Ph—C 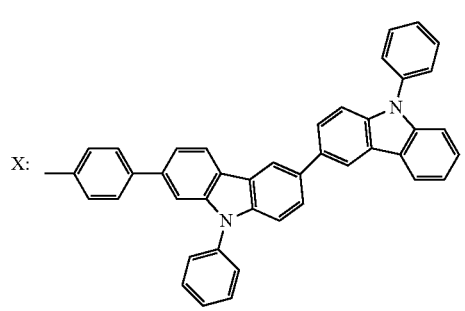 1613576-58-1 | X: 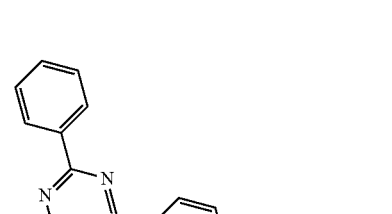 | 37% |
| O5 | O-4-BRSE-Ph—C 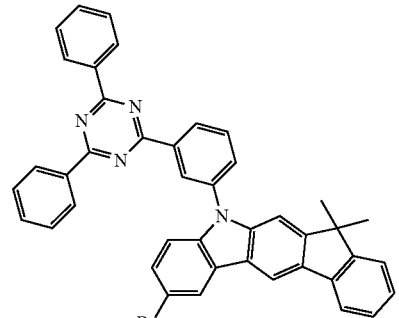 2138491-00-4 | X: 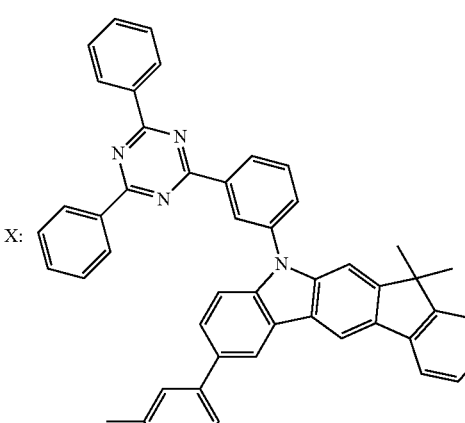 | 35% |

-continued

| Ex. | Reactants | Product | Yield |
|---|---|---|---|
| O6 | O-4-BRSE-Ph—C, 1448787-86-7 | X: | 41% |
| O7 | O-3-BRSE-Ph—C, 1909242-48-3 | X: | 26% |
| O8 | O-4-BRSE-Ph—C, 185626-73-7 | X: | 29% |

It is analogously possible to react O-3-BRSE-Ph-C and O-4-BRSE-Ph-C with mono-bromo-functionalized oligophenylenes, fluorene, carbazole, dibenzofuran or mixtures thereof. Purification is effected by reprecipitation of the crude product from DCM in methanol or by chromatography, flash chromatography or gel permeation chromatography. Some examples of suitable bromides are listed in the table which follows in the form of the CAS numbers:

| Ex. | CAS |
|---|---|
| O9 | 180802-93-1 |
| O10 | 180802-96-4 |
| O11 | 797789-75-4 |
| O12 | 1382210-35-6 |
| O13 | 1310675-72-9 |
| O14 | 5121-77-7 |
| O15 | 1184456-33-4 |
| O16 | 863111-73-3 |
| O17 | 1134375-86-2 |
| O18 | 446879-01-2 |
| O19 | 1609238-90-5 |
| O20 | 1356465-30-9 |

Solution-Processed Devices:

A: From Soluble Functional Materials of Low Molecular Weight

The materials of the invention can be processed from solution. The production of such components is based on the production of polymeric light-emitting diodes (PLEDs), which has already been described many times in the literature (for example in WO 2004/037887). The structure is composed of substrate/ITO/hole injection layer (60 nm)/interlayer (20 nm)/emission layer (60 nm)/hole blocker layer (10 nm)/electron transport layer (40 nm)/cathode. For this purpose, substrates from Technoprint (soda-lime glass) are used, to which the ITO structure (indium tin oxide, a transparent conductive anode) is applied. The substrates are cleaned in a cleanroom with DI water and a detergent (Deconex 15 PF) and then activated by a UV/ozone plasma treatment. Thereafter, likewise in a cleanroom, a 20 nm hole injection layer is applied by spin-coating (PEDOT:PSS from Clevios™). The required spin rate depends on the degree of dilution and the specific spin-coater geometry. In order to remove residual water from the layer, the substrates are baked on a hotplate at 200° C. for 30 minutes. The interlayer used serves for hole transport, in this case, HL-X from Merck is used. The interlayer may alternatively also be replaced by one or more layers which merely have to fulfill the condition of not being leached off again by the subsequent processing step of EML deposition from solution. For production of the emission layer, the triplet emitters of the invention are dissolved together with the matrix materials in toluene or chlorobenzene. The typical solids content of such solutions is between 16 and 25 g/l when, as here, the layer thickness of 60 nm which is typical of a device is to be achieved by means of spin-coating. The solution-processed devices contain an emission layer composed of Material1: Material2:Material3:Emitter (for percentages by weight see table 1). The emission layer is spun on in an inert gas atmosphere, argon in the present case, and baked at 160° C. for 30 min. Vapor-deposited atop the latter are the hole blocker layer (10 nm ETM1) and the electron transport layer (40 nm ETM1 (50%)/ETM2 (50%)) (vapor deposition systems from Lesker or the like, typical vapor deposition pressure $5\times10^{-6}$ mbar). Finally, a cathode of aluminum (100 nm) (high-purity metal from Aldrich) is applied by vapor deposition. In order to protect the device from air and air humidity, the device is finally encapsulated and then characterized. The OLED examples cited are yet to be optimized; table 1 summarizes the data obtained. The lifetime LT50 is defined as the time after which the luminance in operation drops to 50% of the starting luminance with a starting brightness of 1000 cd/m².

TABLE 1

Results for the devices

| Ex. | Material1 Material2 Material3 Emitter | EQE (%) 1000 cd/m² | Voltage (V) 1000 cd/m² | CIE x/y | LT50 (h) 1000 cd/m² |
|---|---|---|---|---|---|
| Sol-D1 | M4 (20%) TMM2 (58%) — IrL (22%) | 20.1 | 4.6 | 0.33/0.62 | 300000 |
| Sol-D2 | O4 (10%) TMM2 (66%) — IrL (24%) | 21.8 | 4.4 | 0.33/0.62 | 330000 |
| Sol-D3 | M1 (10%) TMM2 (58%) M2 (10%) IrL (22%) | 20.6 | 4.2 | 0.33/0.63 | 320000 |
| Sol-D4 | M3 (10%) TMM2 (58%) M2 (10%) IrL (22%) | 20.2 | 4.3 | 0.32/0.63 | 300000 |
| Sol-D5 | D1 (12%) TMM2 (58%) D2 (8%) IrL (22%) | 22.0 | 4.5 | 0.33/0.63 | 290000 |
| Sol-D6 | TMM1 (40%) O1 (40%) — IrL (20%) | 20.3 | 4.2 | 0.32/0.62 | 320000 |
| Sol-D7 | TMM1 (40%) O2 (40%) — IrL (20%) | 20.5 | 4.4 | 0.32/0.62 | 360000 |
| Sol-D7 | O4 (40%) O8 (40%) — IrL (20%) | 22.0 | 4.3 | 0.32/0.63 | 340000 |
| Sol-D8 | O3 (10%) TMM2 (60%) O5 (10%) IrL (20%) | 21.7 | 4.3 | 0.33/0.63 | 320000 |
| Sol-D9 | | 3.0 | 5.4 | 0.14/0.12 | — |
| Sol-D10 | O9 (10%) TMM2 (60%) — IrL (30%) | 19.7 | 4.4 | 0.33/0.62 | 260000 |
| Sol-D11 | O12 (10%) TMM2 (60%) — IrL (30%) | 14.9 | 4.2 | 0.33/0.64 | 330000 |

B: Use of the Compounds of the Invention in Crosslinkable Hole Conductor Layers

The production of solution-processed OLEDs with a crosslinkable hole conductor unit has already been described in WO 2004/037887 and WO 2010/097155. The basic production method is adapted to the materials and layer thicknesses described below. The compounds of the invention are used in the following structure:

substrate,
indium tin oxide ITO (50 nm),
PEDOT (80 nm),
hole transport layer (HTL) (20 nm),
emission layer (EML) (60 nm),
hole blocker layer (HBL) (10 nm),
electron transport layer (ETL) (40 nm),
cathode.

For this purpose, substrates from Technoprint (soda-lime glass) are used, to which the ITO structure (indium tin oxide, a transparent conductive anode) is applied. The substrates are cleaned in a cleanroom with DI water and a detergent (Deconex 15 PF) and then activated by a UV/ozone plasma treatment. Thereafter, likewise in a cleanroom, an 80 nm hole injection layer of PEDOT-PSS (commercially available from Heraeus GmbH & Co. KG, Germany) is applied by spin-coating. The required spin rate depends on the degree of dilution and the specific spin-coater geometry. In order to remove residual water from the layer, the substrates are baked on a hotplate at 180° C. for 20 minutes. The compounds of the invention serve as hole transport layer, optionally in combination with other hole conductor materials. They are applied from toluenic solution, solids content typically about 7 g/l, at a layer thickness of about 20 nm, by spin-coating under inert atmosphere (argon), and baked at 220° C. for 60 min.

For production of the emission layer, the triplet emitters are dissolved together with the matrix materials in toluene or chlorobenzene. The typical solids content of such solutions is between 16 and 25 g/l when, as here, the layer thickness of 60 nm which is typical of a device is to be achieved by means of spin-coating. The solution-processed triplet devices contain an emission layer composed of Material1:Material2:Material3:Emitter (for percentages by weight see table 1). The emission layer is spun on in an inert gas atmosphere, argon in the present case, and baked at 160° C. for 20 min. Vapor-deposited atop the latter are the hole blocker layer (10 nm ETM1) and the electron transport layer (40 nm ETM1 (50%)/ETM2 (50%)) (vapor deposition systems from Lesker or the like, typical vapor deposition pressure $5 \times 10^{-6}$ mbar). Finally, a cathode of aluminum (100 nm) (high-purity metal from Aldrich) is applied by vapor deposition. In order to protect the device from air and air humidity, the device is finally encapsulated and then characterized. The OLED examples cited are yet to be optimized; table 2 summarizes the data obtained. The lifetime LT50 is defined as the time after which the luminance in operation drops to 50% of the starting luminance with a starting brightness of 1000 cd/m².

TABLE 2

Results for the triplet devices

| Ex. | HLT Material1 Material2 | EML Material1 Material2 Material3 Emitter | EQE (%) 1000 cd/m² | Voltage (V) 1000 cd/m² | CIE x/y | LT50 (h) 1000 cd/m² |
|---|---|---|---|---|---|---|
| Sol-C1 | O7 (100 %) — | TMM1 (20%) TMM2 (58%) IrL (22%) | 19.8 | 4.6 | 0.33/0.62 | 280000 |
| Sol-C2 | O7 (70 %) HTM1 (30 %) | TMM1 (20%) TMM2 (60%) IrL (20%) | 20.2 | 4.4 | 0.32/0.62 | 310000 |

TABLE 4

Structural formulae of the materials used

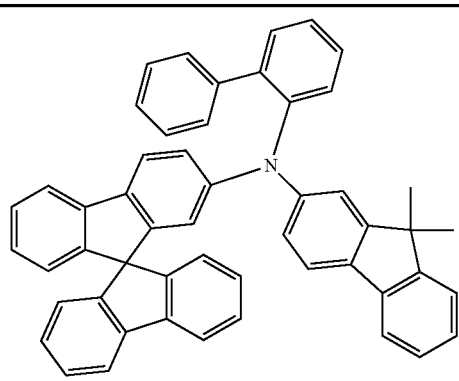

HTM1
136463-07-5

TABLE 4-continued

Structural formulae of the materials used

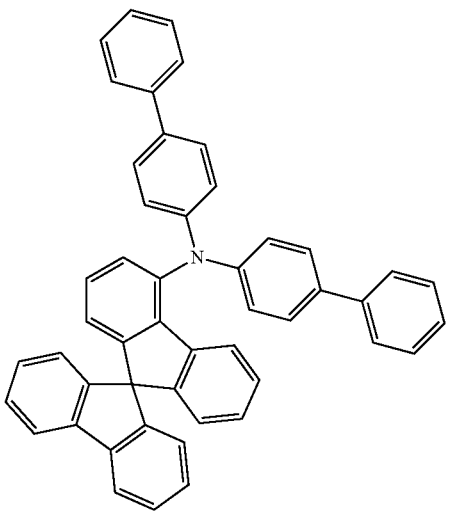

HTM2
1450933-43-3

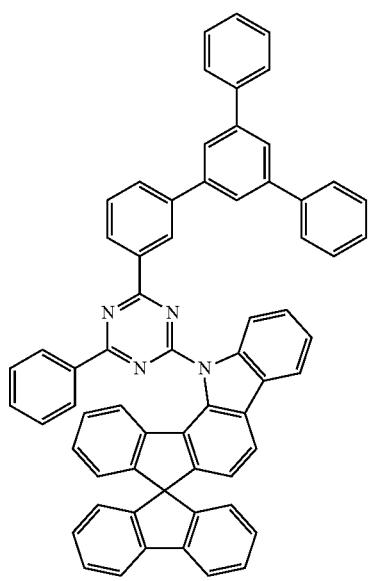

TMM1
1616231-60-7

TABLE 4-continued

Structural formulae of the materials used

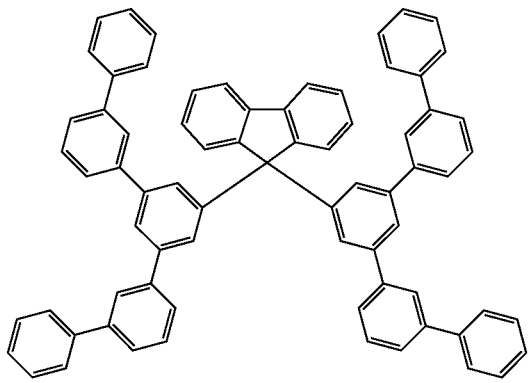

TMM2
1246496-85-4

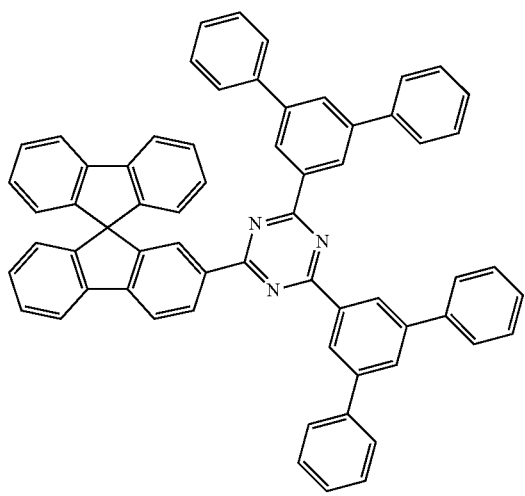

1233200-52-6

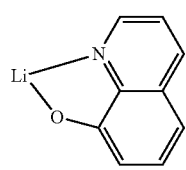

ETM2
25387-93-3

TABLE 4-continued

Structural formulae of the materials used

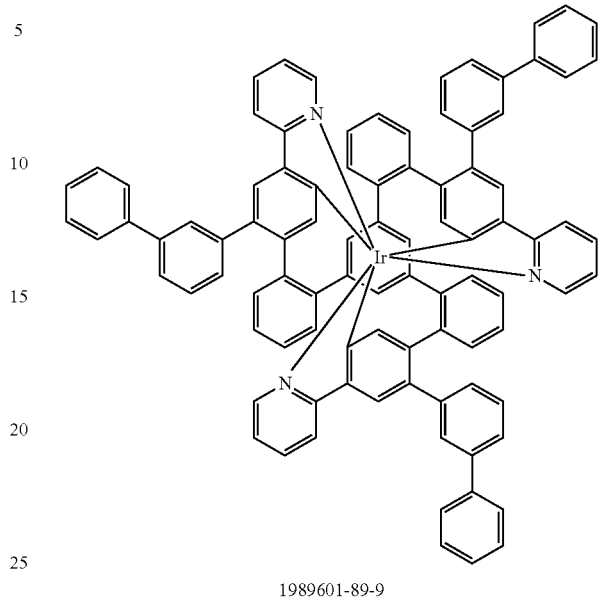

1989601-89-9

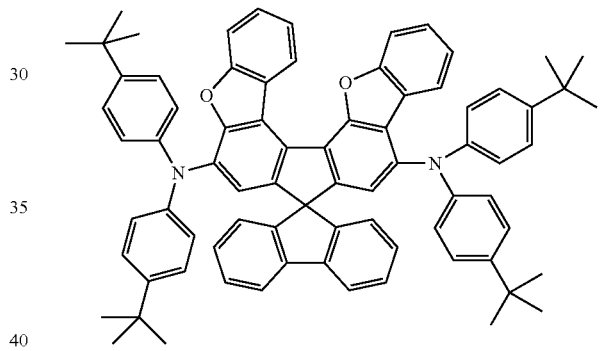

1827604-67-0
B1

The invention claimed is:

1. A compound usable as active compound in an organic electronic device, characterized in that the compound comprises at least one structure of the formula (I)

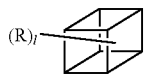

Formula (I)

where:

l is an integer in the range from 1 to 8;

R is the same or different at each instance and is H, D, OH, F, Cl, Br, I, CN, NO$_2$, N(Ar)$_2$, N(R$^1$)$_2$, C(=O)N(Ar)$_2$, C(=O)N(R$^1$)$_2$, Si(Ar)$_3$, Si(R$^1$)$_3$, B(Ar)$_2$, B(R$^1$)$_2$, C(=O)Ar, C(=O)R$^1$, P(=O)(Ar)$_2$, P(=O)(R$^1$)$_2$, P(Ar)$_2$, P(R$^1$)$_2$, S(=O)Ar, S(=O)R$^1$, S(=O)$_2$Ar, S(=O)$_2$R$^1$, OSO$_2$Ar, OSO$_2$R$^1$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may in each case be substituted by one or more $R^1$ radicals, where one or more nonadjacent $CH_2$ groups may be replaced by $R^1C=CR^1$, $C\equiv C$, $Si(R^1)_2$, $Ge(R^1)_2$, $Sn(R^1)_2$, $C=O$, $C=S$, $C=Se$, $C=NR^1$, $-C(=O)O-$, $-C(=O)NR^1-$, $NR^1$, $P(=O)(R^1)$, $-O-$, $-S-$, $SO$ or $SO_2$, or an aromatic or heteroaromatic ring system which has 5 to 60 aromatic ring atoms and may be substituted in each case by one or more $R^1$ radicals, or an aryloxy or heteroaryloxy group which has 5 to 60 aromatic ring atoms and may be substituted by one or more R radicals; at the same time, two R radicals together may also form a ring system;

Ar is the same or different at each instance and is an aromatic or heteroaromatic ring system which has 5 to 60 aromatic ring atoms and may be substituted by one or more R radicals; at the same time, it is possible for two Ar radicals bonded to the same silicon atom, nitrogen atom, phosphorus atom or boron atom also to be joined together via a bridge by a single bond or a bridge selected from $B(R^1)$, $C(R^1)_2$, $Si(R^1)_2$, $C=O$, $C=NR^1$, $C=C(R^1)_2$, O, S, $S=O$, $SO_2$, $N(R^1)$, $P(R^1)$ and $P(=O)R^1$;

$R^1$ is the same or different at each instance and is H, D, F, Cl, Br, I, CN, $NO_2$, $N(Ar^1)_2$, $N(R^2)_2$, $C(=O)Ar^1$, $C(=O)R^2$, $P(=O)(Ar^1)_2$, $P(Ar^1)_2$, $B(Ar^1)_2$, $B(R^2)_2$, $Si(Ar^1)_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $-C(=O)O-$, $-C(=O)NR^2-$, $NR^2$, $P(=O)(R^2)$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a combination of these systems; at the same time, two or more $R^1$ radicals together may form a ring system; at the same time, one or more $R^1$ radicals with a further part of the compound may form a ring system;

$Ar^1$ is the same or different at each instance and is an aromatic or heteroaromatic ring system which has 5 to 30 aromatic ring atoms and may be substituted by one or more $R^2$ radicals; at the same time, two $Ar^1$ radicals bonded to the same silicon atom, nitrogen atom, phosphorus atom or boron atom may also be joined together via a bridge by a single bond or a bridge selected from $B(R^2)$, $C(R^2)_2$, $Si(R^2)_2$, $C=O$, $C=NR^2$, $C=C(R^2)_2$, O, S, $S=O$, $SO_2$, $N(R^2)$, $P(R^2)$ and $P(=O)R^2$;

$R^2$ is the same or different at each instance and is H, D, F, Cl, Br, I, CN, $B(OR^3)_2$, $NO_2$, $C(=O)R^3$, $CR^3=C(R^3)_2$, $C(=O)OR^3$, $C(=O)N(R^3)_2$, $Si(R^3)_3$, $P(R^3)_2$, $B(R^3)_2$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by $-R^3C=CR^3-$, $-C\equiv C-$, $Si(R^3)_2$, $Ge(R^3)_2$, $Sn(R^3)_2$, $C=O$, $C=S$, $C=NR^3$, $-C(=O)O-$, $-C(=O)NR^3-$, $NR^3$, $P(=O)(R^3)$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^3$ radicals, or an aryloxy or heteroaryloxy group which has 5 to 40 aromatic ring atoms and may be substituted by one or more $R^3$ radicals, or a combination of these systems; at the same time, two or more substituents $R^2$ together may also form a ring system;

$R^3$ is the same or different at each instance and is selected from the group consisting of H, D, F, CN, an aliphatic hydrocarbyl radical having 1 to 20 carbon atoms or an aromatic or heteroaromatic ring system which has 5 to 30 aromatic ring atoms and in which one or more hydrogen atoms may be replaced by D, F, Cl, Br, I or CN and which may be substituted by one or more alkyl groups each having 1 to 4 carbon atoms; at the same time, two or more substituents $R^3$ together may form a ring system.

2. The compound as claimed in claim 1, characterized in that the compound usable as active compound in an organic electronic device is selected from the group consisting of fluorescent emitters, phosphorescent emitters, emitters that exhibit TADF (thermally activated delayed fluorescence), host materials, electron transport materials, exciton blocker materials, electron injection materials, hole conductor materials, hole injection materials, n-dopants, p-dopants, wide bandgap materials, electron blocker materials and/or hole blocker materials.

3. The compound as claimed in claim 1, characterized in that the compound comprises at least one structure of the formula (II)

Formula (II)

where the R radical has the definition given in claim 1 in addition:

l is an integer in the range from 1 to 8;
m is an integer in the range from 0 to 7;
m+l is not more than 8;
$R^a$ is the same or different at each instance and is OH, F, Cl, Br, I, CN, $NO_2$, $N(Ar)_2$, $N(R^1)_2$, $C(=O)N(Ar)_2$, $C(=O)N(R^1)_2$, $Si(Ar)_3$, $Si(R^1)_3$, $B(Ar)_2$, $B(R^1)_2$, $C(=O)Ar$, $C(=O)R^1$, $P(=O)(Ar)_2$, $P(=O)(R^1)_2$, $P(Ar)_2$, $P(R^1)_2$, $S(=O)Ar$, $S(=O)R^1$, $S(=O)_2Ar$, $S(=O)_2R^1$, $OSO_2Ar$, $OSO_2R^1$, a straight-chain alkyl, alkoxy or thioalkoxy group having 1 to 20 carbon atoms or an alkenyl or alkynyl group having 2 to 40 carbon atoms or a branched or cyclic alkyl, alkoxy or thioalkoxy group having 3 to 40 carbon atoms, where the alkyl, alkoxy, thioalkoxy, alkenyl or alkynyl group may in each case be substituted by one or more $R^1$ radicals, where one or more nonadjacent $CH_2$ groups may be replaced by $R^1C=CR^1$, $C\equiv C$, $Si(R^1)_2$, $Ge(R^1)_2$, $Sn(R^1)_2$, $C=O$, $C=S$, $C=Se$, $C=NR^1$, $-C(=O)O-$, $-C(=O)NR^1-$, $NR^1$, $P(=O)(R^1)$, $-O-$, $-S-$, SO or $SO_2$, or an aromatic or heteroaromatic ring system which has 5 to 60 aromatic ring atoms and may be substituted in each case by one or more R¹ radicals, or an aryloxy or heteroaryloxy group which has 5 to 60 aromatic ring atoms and may be substituted by one or more R radicals; at the same time, $R^a$ radicals together with an R radical may also form a ring system, where the Ar and R¹ radicals have the definition given in claim 1.

4. The compound as claimed in claim 3, characterized in that the compound has at least one structure of the formulae (IIIa), (IIIb) and (IIIc)

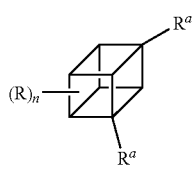

Formula (IIIa)

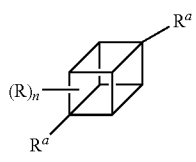

Formula (IIIb)

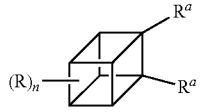

Formula (IIIc)

where the R radical has the definition given in claim 1, the $R^a$ radicals have the definition given in claim 3, and n is an integer in the range from 0 to 6.

5. The compound as claimed in claim 3, characterized in that the compound has at least one structure of the formulae (IVa), (IVb) and (IVc)

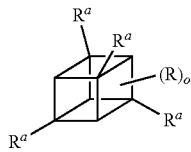

Formula (IVa)

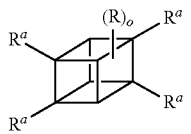

Formula (IVb)

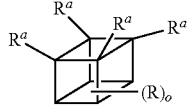

Formula (IVc)

where the $R^a$ radicals have the definition given in claim 3, and o is an integer in the range from 0, 1, 2 or 3.

6. The compound as claimed in claim 3, characterized in that the compound has at least one structure of the formula (V)

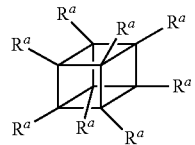

Formula (V)

the $R^a$ radicals have the definition given in claim 3.

7. The compound as claimed in claim 1, characterized in that the compound has point symmetry and/or axial symmetry.

8. The compound as claimed in claim 1, characterized in that the compound comprises a hole transport group, where one of the R and/or $R^a$ groups comprises and is a hole transport group.

9. The compound as claimed in claim 1, characterized in that the compound comprises an electron transport group, where one of the R and/or $R^a$ groups comprises and is an electron transport group.

10. The compound as claimed claim 1, characterized in that at least one of the R and/or $R^a$ radicals comprises at least one group that leads to with wide bandgap materials.

11. The compound as claimed in claim 1, characterized in that at least one of the R and/or $R^a$ radicals comprises at least one aromatic or heteroaromatic ring system having two or three, fused aromatic or heteroaromatic rings.

12. The compound as claimed in claim 1, characterized in that at least one of the R and/or $R^a$ radicals is selected from the group of the fluorenes, indenofluorenes, spirobifluorenes, carbazoles, indenocarbazoles, indolocarbazoles, spirocarbazoles, pyrimidines, triazines, lactams, triarylamines, dibenzofurans, dibenzothienes, imidazoles, benzimidazoles, benzoxazoles, benzothiazoles, 5-arylphenanthridin-6-ones, 9,10-dehydrophenanthrenes, fluoranthenes, anthracenes, benzanthracenes and fluoradenes.

13. The compound as claimed in claim 1, characterized in that at least one of the R and/or $R^a$ radicals is selected from the group consisting of phenyl, ortho-, meta- or para-biphenyl, terphenyl, quaterphenyl, 1-, 2-, 3- or 4-fluorenyl, 9,9'-diarylfluorenyl 1-, 2-, 3- or 4-spirobifluorenyl, pyridyl, pyrimidinyl, 1-, 2-, 3- or 4-dibenzofuranyl, 1-, 2-, 3- or 4-dibenzothienyl, pyrenyl, triazinyl, imidazolyl, benzimidazolyl, benzoxazolyl, benzothiazolyl, 1-, 2-, 3- or 4-carbazolyl, 1- or 2-naphthyl, anthracenyl, trans- and cis-indenofluorenyl, indenocarbazolyl, indolocarbazolyl, spirocarbazolyl, 5-aryl-phenanthridin-6-on-yl, 9,10-dehydrophenanthrenyl, fluoranthenyl, tolyl, mesityl, phenoxytolyl, anisolyl, triarylaminyl, bis(triarylaminyl), tris(triarylaminyl), hexamethylindanyl, tetralinyl, monocycloalkyl, biscycloalkyl, tricycloalkyl, alkyl, for example tert-butyl, methyl, propyl, alkoxyl, alkylsulfanyl, alkylaryl, triarylsilyl, trialkylsilyl, xanthenyl, 10-arylphenoxazinyl, phenanthrenyl and/or triphenylenyl, each of which may be substituted by one or more radicals.

14. The compound as claimed claim 1, wherein the compound is defined by the formulae (I), (II), (IIIa), (IIIb), (IIIc), (IVa), (IVb), (IVc) and (V)

Formula (II)

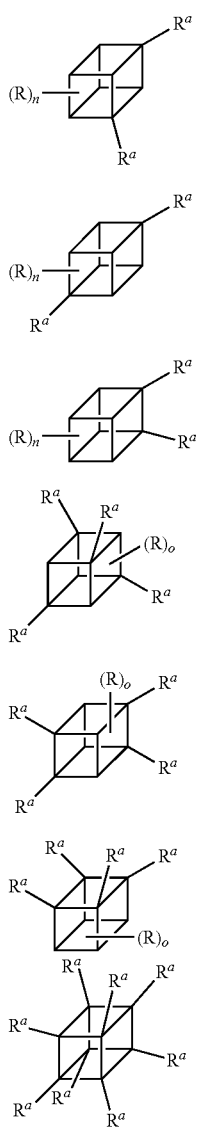

Formula (IIIa)

Formula (IIIb)

Formula (IIIc)

Formula (IVa)

Formula (IVb)

Formula (IVc)

where the R radical has the definition given in claim 1 and in addition:
l is an integer in the range from 1 to 8;
m is an integer in the range from 0 to 7;
m+l is not more than 8;
n is an integer in the range from 0 to 6;
o is an integer in the range from 0, 1, 2 or 3;
$R^a$ is the same or different at each instance and is OH, F, Cl, Br, I, CN, $NO_2$, $N(Ar)_2$, $N(R^1)_2$, $C(=O)N(Ar)_2$, $C(=O)N(R^1)_2$, $Si(Ar)_3$, $Si(R^1)_3$, $B(Ar)_2$, $B(R^1)_2$, $C(=O)Ar$, $C(=O)R^1$, $P(=O)(Ar)_2$, $P(=O)(R^1)_2$, $P(Ar)_2$, $P(R^1)_2$, $S(=O)Ar$, $S(=O)R^1$, $S(=O)_2Ar$, $S(=O)_2R^1$, $OSO_2Ar$, $OSO_2R^1$, a straight-chain alkyl, alkoxy or thioalkoxy group having 1 to 20 carbon atoms or an alkenyl or alkynyl group having 2 to 40 carbon atoms or a branched or cyclic alkyl, alkoxy or thioalkoxy group having 3 to 40 carbon atoms, where the alkyl, alkoxy, thioalkoxy, alkenyl or alkynyl group may in each case be substituted by one or more $R^1$ radicals, where one or more nonadjacent $CH_2$ groups may be replaced by $R^1C=CR^1$, $C\equiv C$, $Si(R^1)_2$, $Ge(R^1)_2$, $Sn(R^1)_2$, $C=O$, $C=S$, $C=Se$, $C=NR^1$, $—C(=O)O—$, $—C(=O)NR^1—$, $NR^1$, $P(=O)(R^1)$, $—O—$, $—S—$, SO or $SO_2$, or an aromatic or heteroaromatic ring system which has 5 to 60 aromatic ring atoms and may be substituted in each case by one or more $R^1$ radicals, or an aryloxy or heteroaryloxy group which has 5 to 60 aromatic ring atoms and may be substituted by one or more $R^1$ radicals; at the same time, $R^a$ radicals together with an R radical may also form a ring system.

15. An oligomer, polymer or dendrimer containing one or more compounds as claimed in claim 1, wherein, rather than a hydrogen atom or a substituent, there are one or more bonds of the compounds to the polymer, oligomer or dendrimer.

16. A composition comprising at least one compound as claimed in claim 1 or an oligomer, polymer or dendrimer as claimed in claim 15 and at least one further compound selected from the group consisting of fluorescent emitters, phosphorescent emitters, emitters that exhibit TADF (thermally activated delayed fluorescence), host materials, electron transport materials, electron injection materials, hole conductor materials, hole injection materials, electron blocker materials and hole blocker materials.

17. A formulation comprising at least one compound as claimed in claim 1 at least one solvent.

18. A process for preparing the compound as claimed in claim 1 which comprises in a coupling reaction, a compound comprising at least one nonaromatic or nonheteroaromatic polycyclic ring system having a cubane structure is joined to a compound comprising at least one aromatic or heteroaromatic group.

19. An electronic device comprising at least one compound as claimed in claim 1.

20. The electronic device as claimed in claim 19, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field-quench devices, light-emitting electrochemical cells and organic laser diodes.

* * * * *